(12) United States Patent
Palacios et al.

(10) Patent No.: US 11,607,413 B2
(45) Date of Patent: Mar. 21, 2023

(54) DOSAGE REGIME AND METHOD FOR TREATING PULMONARY ARTERIAL HYPERTENSION

(71) Applicant: Altavant Sciences GmbH, Basel (CH)

(72) Inventors: Michelle Palacios, Raleigh, NC (US); Eric J. Gaukel, Raleigh, NC (US); Stephen A. Wring, South Boston, VA (US); Magdalena Alonso-Galicia, Durham, NC (US)

(73) Assignee: Altavant Sciences GmbH, Basel (CH)

( * ) Notice: Subject to any disclaimer, the term of this patent is extended or adjusted under 35 U.S.C. 154(b) by 87 days.

(21) Appl. No.: 16/777,458

(22) Filed: Jan. 30, 2020

(65) Prior Publication Data

US 2020/0237759 A1 Jul. 30, 2020

Related U.S. Application Data

(60) Provisional application No. 62/798,827, filed on Jan. 30, 2019.

(51) Int. Cl.
*A61K 31/506* (2006.01)
*A61K 9/00* (2006.01)

(52) U.S. Cl.
CPC .......... *A61K 31/506* (2013.01); *A61K 9/0053* (2013.01)

(58) Field of Classification Search
CPC ................................ A61K 31/506; A61K 9/00
See application file for complete search history.

(56) References Cited

U.S. PATENT DOCUMENTS

| | | | |
|---|---|---|---|
| 9,199,994 | B2 | 12/2015 | De Lombaert et al. |
| 9,512,122 | B2 | 12/2016 | De Lombaert et al. |
| 9,750,740 | B2 | 9/2017 | De Lombaert et al. |
| 10,045,988 | B2 | 8/2018 | De Lombaert et al. |
| 10,350,208 | B2 | 7/2019 | De Lombaert et al. |
| 10,660,893 | B2 | 5/2020 | De Lombaert et al. |
| 10,946,018 | B2 | 3/2021 | De Lombaert et al. |
| 2020/0148681 | A1 | 5/2020 | Patterson |
| 2020/0155552 | A1 | 5/2020 | Wring et al. |
| 2020/0188398 | A1 | 6/2020 | Pack et al. |
| 2020/0188399 | A1 | 6/2020 | Pack et al. |
| 2020/0237759 | A1 | 7/2020 | Palacios et al. |
| 2020/0289510 | A1* | 9/2020 | Alonso-Galicia .... A61K 31/506 |

FOREIGN PATENT DOCUMENTS

| | | | |
|---|---|---|---|
| WO | 2009009561 | A1 | 1/2009 |
| WO | 2015035113 | A1 | 3/2015 |
| WO | 2020099926 | A1 | 5/2020 |
| WO | 2020099929 | A1 | 5/2020 |
| WO | 2020128608 | A1 | 6/2020 |
| WO | 2020157577 | A1 | 8/2020 |

OTHER PUBLICATIONS

Aiello et al, J'nal of Pharm & Exp Ther. vol. 360(2) 2017.*
Paralkar et al., Amer J'nal of Resp & Critical Care Med., Amer. Thoracic Society. vol 195 (2017).*
International Preliminary Report on Patentability for corresponding international application PCT/IB2020/000074, 8 pages, dated Jul. 27, 2021.
Aiello et al: "Tryptophan hydroxylase 1 Inhibition Impacts Pulmonary Vascular Remodeling in Two Rat Models of Pulmonary Hypertension" Journal of Pharmacology and Experimental Therapeutics, vol. 360, No. 2, pp. 267-279, Jan. 6, 2017.
Paralkar et al: "KAR5585, a first-in-class oral tryptophan hydroxylase 1 (TPH1) inhibitor as a novel candidate for the treatment of pulmonary arterial hypertension" American Journal of Respiratory and Critical Care Medicine, American Thoracic Society, United States, vol. 195, Jan. 1, 2017.
Bader et al. "Inhibition of serotonin synthesis: A novel therapeutic paradigm" Pharmacology & Therapeutics, vol. 205, Oct. 17, 2019.
Wring et al: "Safety, tolerability, pharmacokinetics and pharmacodynamics after repeated once or twice daily RUT-1201, a TPH inhibitor for treatment of PAH",European Respiratory Journal Sep. 1, 2019 European Respiratory Society NLD, vol. 54, No. Supplement 63, Sep. 1, 2019.
International Search Report for corresponding international application PCT/IB2020/000074, 6 pages, dated Jun. 26, 2020.
Written Opinion of the International Search Authority for corresponding international application PCT/IB2020/000074, 9 pages, dated Jun. 26, 2020.

(Continued)

*Primary Examiner* — Paul V Ward
(74) *Attorney, Agent, or Firm* — Fox Rothschild LLP

(57) ABSTRACT

There is provided a daily dosage regimen for treating pulmonary arterial hypertension. The regimen takes the form of two discrete dosage forms. Each dosage form includes an amount of about 600 mg to about 800 mg of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate. There is also another method for providing a daily dosage regimen. There is also provided several methods for treating pulmonary arterial hypertension. There is provided a method for reducing the level of serotonin biosynthesis by at least 50%. There is also provided a method for achieving an $AUC_{0\text{-}tau}$ of $\geq 2530$ ng·hr/mL of (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid. There is provided a method of achieving a >50% reduction in urinary 5-HIAA.

28 Claims, 20 Drawing Sheets

(56) References Cited

OTHER PUBLICATIONS

Mawe et al, "Serotonin signaling in the gut—functions, dysfunctions and therapeutic targets," Nature-Gastroenterology & Hepatology, Aug. 2013, 10:473-486.
Gershon, M. D. "5-hydroxytryptamine (serotonin) In The Gastrointestinal Tract". Current Opinion in Endocrinology, Diabetes, and Obesity 20, 14-21 (2013).
Lesurtel et al., "Role of Serotonin In The Hepato-gastrointestinal Tract: An Old Molecule For New Perspectives," Cell. Mol. Life Sci., 2008 65:940-952.
Kode et al., "FOXO1 orchestrates the bone-suppressing function of gut-derived serotonin," J. Clinical Investigation, Jul. 2012.
Yadav et al., "Pharamacological inhibition of gut-derived serotonin synthesis is a potential bone anabolic treatment for osteoporosis," Nature Medicine, Feb. 2010, 1-14.
Yadav et al., "Lrp5 Controls Bone Formation by Inhibiting Serotonin Synthesis in the Duodenum," Cell, Nov. 2008, 135:825-837.
Liang et al., "Serotonin Promotes The Proliferation Of Serum-deprived Hepatocellular Carcinoma Cells via Upregulation Of FOXO3a," Molecular Cancer, 2013, 12:14.
Soil et al., "Serotonin Promotes Tumor Growth in Human Hepatocellular Cancer," Hepatology 2010, 51 (4):1244-1254.
Pai et al., "Altered serotonin physiology in human breast cancers favors paradoxical growth and cell survival," Breast Cancer Research, Nov. 2009, 11(6):1-17.
Engelman et al., "Inhibition Of Serotonin Synthesis By Parachlorophenylalanine In Patients With The Carcinoid Syndrome," The New England Journal of Medicine, Nov. 1967, 277:1103-1108.
Sumara et al., "Gut-derived Serotonin is a Multifunctional Determinant to Fasting Adaptation," Cell Metabolism, Nov. 2012, 16:1-13.
Ban et al., "Impact Of Increased Plasma Serotonin Levels and Carotid Atherosclerosis On Vascular Dementia," Atherosclerosis, 2007, 195, 153-159.
Manocha et al.,"Serotonin and GI Disorders: An Update on Clinical and Experimental Studies," Clinical and Translational Gastroenterology, 2012, 3:e13, 6 pages.
Ghia et al., "Serotonin has a key role in pathogenesis of experimental colitis," Gastroenterology, 2009, 137(5): 1649-1660.
Sikander et al., "Role of serotonin in gastrointestinal motility and irritable bowel syndrome," Clinica Chimica Acta, 2009,403:47-55.
Galligan et al. "Recent advances in understanding the role of serotonin in gastrointestinal motility and functional bowel disorders," Neurogastroenterol Motil., 2007, 19(Suppl.2):1-4.
Costedio et al., "Serotonin And Its Role In Colonic Function And In Gastrointestinal Disorders," Diseases of the Colon and Rectum, Mar. 2007, 50(3): 376-88.
Gershon and Tack, "The Serotonin Signaling System: From Basic Understanding To Drug Development For Functional GI Disorders," Gastroenterology, 2007, 132:397-414.
Mawe et al., "Review article: intestinal serotonin signaling in irritable bowel syndrome," Aliment Pharmacol Ther, 2006, 23:1067-1076.
Crowell, "Role Of Serotonin In The Pathophysiology Of The Irritable Bowel Syndrome," British Journal of Pharmacology, 2004, 141:1285-93.
Lau et al., "The Role Of Circulating Serotonin In The Development Of Chronic Obstructive Pulmonary Disease," PloS One, Feb. 2012, 7(2):e31617, 7 pages.
Egermayer et al., "Role Of Serotonin In The Pathogenesis Of Acute And Chronic Pulmonary Hypertension," Thorax, 1999, 54:161-168.
Duerschmied et al., "Platelet Serotonin Promotes The Recruitment Of Neutrophils To Sites Of Acute Inflammation In Mice," Blood, Feb. 2013, 121(6):1008-1015.
Li et al., "Serotonin Activates Dendritic Cell Function In The Context Of Gut Inflammation," The American Journal of Pathology, Feb. 2011, 178(2):662-671.
Ebrahimkhani et al., "Stimulating Healthy Tissue Regeneration By Targeting The 5-HT2B Receptor In Chronic Liver Disease," Nature Medicine, 2011 17, 1668-1673.
Wacker et al., "Structural Features for Functional Selectivity at Serotonin Receptors," Science, May 2013, 340(6132):615-619.
Stokes et al., "p-Ethynylphenylalanine: A Potent Inhibitor of Tryptophan Hydroxylase," J Neurochemistry, 2000, 74(5):2067-2073.
Zhong et al., "Molecular Dynamics Simulation of Tryptophan Hydroxylase-1: Binding Modes and Free Energy Analysis to Phenylalanine Derivative Inhibitors," Int. J Molecular Sci, May 2013, 14:9947-9962.
Camilleri, "LX-1031, A Tryptophan 5-hydroxylase Inhibitor, And Its Potential In Chronic Diarrhea Associated With Increased Serotonin," Neurogastroenterol Motil., Mar. 2011, 23(3):193-200.
Cianchetta et al., "Mechanism of Inhibition of Novel Tryptophan Hydroxylase Inhibitors Revealed by Co-crystal Structures and Kinetic Analysis," Current Chemical Genomics, 2010, 4:19-26.
Jin et al., "Substituted 3-(4-(1,3,5-triazin-2-yl)-phenyl)-2-aminopropanoic Acids As Novel Tryptophan Hydroxylase Inhibitors," Bioorganic & Medicinal Chemistry Letters, 2009, 19:5229-5232.
Shi et al., "Modulation of Peripheral Serotonin Levels by Novel Tryptophan Hydroxylase Inhibitors for the Potential Treatment of Functional Gastrointestinal Disorders," J Med Chem, 2008, 51:3684-3687.
Liu et al., "Discovery And Characterization of Novel Tryptophan Hydroxylase Inhibitors That Selectively Inhibit Serotonin Synthesis In The Gastrointestinal Tract," J. Pharmacol. Exp. Ther, 2008, 325(1):47-55.
Margolis et al., "Pharmacological Reduction of Mucosal but Not Neuronal Serotonin Opposes Inflammation In Mouse Intestine," Gut, Jun. 2013, 1-10 (with Supplemental Information).
Ouyang et al., "Combined Structure-Based Pharmacophore and 3D-QSAR Studies on Phenylalanine Series Compounds as TPH1 Inhibitors," Int J Molecular Sci, 2012, 13:5348-5363.
Robiolio et al., "Carcinoid Heart Disease: Correlation of High Serotonin Levels with Valvular Abnormalities Detected by Cardiac Catheterization and Echocardiography," Circulation, 1995, 92:790-795.
Diaz-Guzman et al., "Pulmonary Hypertension Caused by Sarcoidosis", Clin. Chest Med., 29(3), pp. 549-563 (2008).
International Preliminary Report on Patentability issued in international application No. PCT/IB2019/001224, dated May 18, 2021 (8 pages).
U S: "Guidance for Industry Estimating the Maximum Safe Starting Dose in Initial Clinical Trials for Therapeutics in Adult Healthy Volunteers Department of Health and Human Services Food and Drug Administration Center for Drug Evaluation and Research (CDER)", FDA Guidelines, Jul. 1, 2005, table 1, p. 26, Jul. 1, 2005.
International Search Report and Written Opinion issued in international application No. PCT/IB2019/001224, dated Apr. 23, 2020 (15 pages).
International Preliminary Report on Patentability issued in international application No. PCT/IB2020/000177, dated Sep. 16, 2021 (10 pages).
International Search Report and Written Opinion issued in international application No. PCT/IB2020/000177, dated Sep. 1, 2020 (17 pages).

* cited by examiner

→△— 400 mg_fasted
→▲— 400 mg_fed

→△— 400 mg fasted
→▲— 400 mg fed

DOSAGE REGIME AND METHOD FOR TREATING PULMONARY ARTERIAL HYPERTENSION

CROSS-REFERENCE TO A RELATED APPLICATION

The present application claims priority based on U.S. Provisional Application No. 62/798,827, filed Jan. 30, 2019, which is incorporated herein by reference in its entirety.

BACKGROUND OF THE DISCLOSURE

1. Field of the Disclosure

The present disclosure relates to a daily dosage regimen for treating pulmonary arterial hypertension. The present disclosure also relates to methods for treating pulmonary arterial hypertension. The present disclosure further relates to a method for reducing the level of serotonin biosynthesis within a period of time. The present disclosure still further relates to a method for achieving an enhanced level of $AUC_{0\text{-}tau}$ within a period of time. The present disclosure further relates to a method for achieving a reduction in urinary 5-HIAA within a period of time.

2. Description of the Prior Art

Serotonin (5-hydroxytryptamine, 5-HT) is a neurotransmitter that modulates central and peripheral functions by acting on neurons, smooth muscle, and other cell types. 5-HT is involved in the control and modulation of multiple physiological and psychological processes. In the central nervous system (CNS), 5-HT regulates mood, appetite, and other behavioral functions. In the GI system, 5-HT has a general prokinetic role and is an important mediator of sensation (e.g., nausea and satiety) between the GI tract and the brain. Dysregulation of the peripheral 5-HT signaling system has been reported to be involved in the etiology of several conditions (see for example: Mawe, G. M. & Hoffman, J., Serotonin Signalling in the Gut-functions, Dysfunctions and Therapeutic Targets. *Nature Reviews. Gastroenterology & Hepatology* 10, 473-486 (2013); Gershon, M. D. 5-hydroxytryptamine (serotonin) in the Gastrointestinal Tract. *Current Opinion in Endocrinology, Diabetes, and Obesity* 20, 14-21 (2013); Lesurtel, M., Soil, C, Graf, R. & Ciavien, P.-A. Role of Serotonin in the Hepato-gastrointestinal Tract: An Old Molecule for New Perspectives. *Cellular and Molecular Life Sciences: CMLS* 65, 940-52 (2008)). These include osteoporosis (e.g. Kode, A, et al., FOXO1 Orchestrates the Bone-suppressing Function of Gut-derived Serotonin, *The Journal of Clinical Investigation* 122, 3490-503 (2012); Yadav, V, K. et al., Pharmacological Inhibition of Gut-derived Serotonin Synthesis is a Potential Bone Anabolic Treatment for Osteoporosis. *Nature Medicine* 16, 308-12 (2010); Yadav, V. K, et al., Lrp5 Controls Bone Formation by Inhibiting Serotonin Synthesis in the Duodenum, Cell 135, 825-37 (2008), cancer (e.g. Liang, C, et al., Serotonin Promotes the Proliferation of Serum-deprived Hepatocellular Carcinoma Cells Via Upregulation of FOX03a. *Molecular Cancer* 12, 14 (2013); Soll, C. et al., Serotonin Promotes Tumor Growth in Human Hepatocellular Cancer. *Hepatology* 51, 1244-1254 (2010); Pai, V. P et al., Altered Serotonin Physiology in Human Breast Cancers Favors Paradoxical Growth and Cell Survival. *Breast Cancer Research: BCR* 11, R81 (2009); Engelman, K., Lovenberg, W. & Sjoerdsma, A. Inhibition of Serotonin Synthesis by Para-chlorophenylalanine in Patients with The Carcinoid Syndrome. *The New England Journal of Medicine* 277, 1103-8 (1967)), cardiovascular (e.g. Robiolio, P. A, et al., Carcinoid Heart Disease: Correlation of High Serotonin Levels with Valvular Abnormalities Detected by Cardiac Catheterization and Echocardiography. *Circulation* 92, 790-795 (1995), diabetes (e.g. Sumara, G., Sumara, O., Kim, J. K. & Karsenty, G. Gut-derived Serotonin is a Multifunctional Determinant to Fasting Adaptation. *Cell Metabolism* 16, 588-600 (2012), atherosclerosis (e.g. Ban, Y. et al., Impact of Increased Plasma Serotonin Levels and Carotid Atherosclerosis on Vascular Dementia. *Atherosclerosis* 195, 153-9 (2007), as well as gastrointestinal (e.g. Manocha, M. & Khan, W. I. Serotonin and GI Disorders: An Update on Clinical and Experimental Studies. *Clinical and Translational Gastroenterology* 3, el 3 (2012); Ghia, J.-E. et al., Serotonin has a Key Role in Pathogenesis of Experimental Colitis. *Gastroenterology* 137, 1649-60 (2009); Sikander, A., Rana, S. V. & Prasad, K. K., Role of Serotonin in Gastrointestinal Motility and Irritable Bowel Syndrome. *Clinica Chimica Acta; International Journal of Clinical Chemistry* 403, 47-55 (2009); Spiller, R, Recent Advances in Understanding the Role of Serotonin in Gastrointestinal Motility in Functional Bowel Disorders: Alterations In 5-HT Signalling and Metabolism in Human Disease. *Neurogastroenterology and Motility: The Official Journal of The European Gastrointestinal Motility Society* 19 Suppl 2, 25-31 (2007); Costedio, M. M., Hyman, N. & Mawe, G, M, Serotonin and its Role in Colonic Function and In Gastrointestinal Disorders. *Diseases of the Colon and Rectum* 50, 376-88 (2007); Gershon, M. D. & Tack, J., The Serotonin Signalling System: From Basic Understanding to Drug Development for Functional GI Disorders. *Gastroenterology* 132, 397-14 (2007); Mawe, G. M., Coates, M. D. & Moses, P. L. Review Article: Intestinal Serotonin Signalling In Irritable Bowel Syndrome. *Alimentary Pharmacology & Therapeutics* 23, 1067-76 (2006); Crowell, M. D. Role of Serotonin in the Pathophysiology of The Irritable Bowel Syndrome. *British Journal of Pharmacology* 141, 1285-93 (2004)), pulmonary (e.g. Lau, W. K. W. et al., The Role of Circulating Serotonin in the Development of Chronic Obstructive Pulmonary Disease. *PloS One* 7, e31617 (2012); Egermayer, P., Town, G. I. & Peacock, A. J. Role of Serotonin in the Pathogenesis of Acute and Chronic Pulmonary Hypertension. *Thorax* 54, 161-168 (1999), inflammatory (e.g. Margolis, K. G. et al., Pharmacological Reduction of Mucosal but Not Neuronal Serotonin Opposes Inflammation in Mouse Intestine. Gut doi: 10.1 136/gutjnl-2013-304901 (2013); Duerschmied, D. et al., Platelet Serotonin Promotes the Recruitment of Neutrophils to Sites of Acute Inflammation in Mice. *Blood* 121, 1008-15 (2013); Li, N. et al., Serotonin Activates Dendritic Cell Function in the Context of Gut Inflammation. *The American Journal of Pathology* 178, 662-71 (2011), or liver diseases or disorders (e.g. Ebrahimkhani, M. R. et al., Stimulating Healthy Tissue Regeneration by Targeting The 5-HT2B Receptor in Chronic Liver Disease. *Nature Medicine* 17, 1668-73 (2011). The large number of pharmaceutical agents that block or stimulate the various 5-HT receptors is also indicative of the wide range of medical disorders that have been associated with 5-HT dysregulation (see for example: Wacker, D. et al., Structural Features for Functional Selectivity at Serotonin Receptors, Science (New York N.Y.) 340, 615-9 (2013).

The rate-limiting step in 5-HT biosynthesis is the hydroxylation of tryptophan by dioxygen, which is catalyzed by tryptophan hydroxylase (TPH; EC 1.14.16.4) in the presence of the cofactor (6R)-L-erythro-5,6,7,8-tetrahydrobiopterin (BH4). The resulting oxidized product, 5-hydroxy tryptophan (5-HTT) is subsequently decarboxylated by an aromatic amino acid decarboxylase (AAAD; EC 4.1.1.28) to produce 5-HT. Together with phenylalanine hydroxylase (PheOH) and tyrosine hydroxylase (TH), TPH belongs to the pterin-dependent aromatic amino acid hydroxylase family.

Two vertebrate isoforms of TPH, namely TPH1 and TPH2, have been identified. TPH1 is primarily expressed in the pineal gland and non-neuronal tissues, such as entero chromaffin (EC) cells located in the gastrointestinal (GI) tract. TPH2 (the dominant form in the brain) is expressed exclusively in neuronal cells, such as dorsal raphe or myenteric plexus cells. The peripheral and central systems involved in 5-HT biosynthesis are isolated, with 5-HT being unable to cross the blood-brain barrier. Therefore, the peripheral pharmacological effects of 5-HT can be modulated by agents affecting TPH in the periphery, mainly TPH1 in the gut.

A small number of phenylalanine-derived TPH1 inhibitors are known. One example, p-chlorophenylalanine (pCPA), a very weak and unselective irreversible inhibitor of TPH, has proven effective in treating chemotherapy-induced emesis, as well as diarrhea, in carcinoid tumor patients. However, pCPA is distributed centrally and, as a result, its administration has been linked to the onset of depression and other alterations of CNS functions in patients and animals. p-Ethynyl phenylalanine is a more selective and more potent TPH inhibitor than pCPA (Stokes, A, H., et al. p-Ethynylphenylalanine: A Potent Inhibitor of Tryptophan Hydroxylase. *Journal of Neurochemistry* 74, 2067-73 (2000), but also affects central 5-HT production and, like pCPA, is believed to irreversibly interfere with the synthetic behavior of TPH (and possibly interact with other proteins).

More recently, bulkier phenylalanine-derived TPH inhibitors have been reported to reduce intestinal 5-HT concentration without affecting brain 5-HT levels (Zhong, H. et al., Molecular dynamics simulation of tryptophan hydroxylase-1: binding modes and free energy analysis to phenylalanine derivative inhibitors. *International Journal of Molecular Sciences* 14, 9947-62 (2013); Ouyang, L., et al., Combined Structure-Based Pharmacophore and 3D-QSA Studies on Phenylalanine Series Compounds as TPH1 Inhibitors. *International Journal of Molecular Sciences* 13, 5348-63 (2012); Camilleri, M. LX-1031, A Tryptophan 5-hydroxylase Inhibitor, and its Potential in Chronic Diarrhea Associated with Increased Serotonin. *Neurogastroenterology and Motility: The Official Journal of the European Gastrointestinal Motility Society* 23, 193-200 (2011); Cianchetta, G., et al., Mechanism of Inhibition of Novel Tryptophan Hydroxylase Inhibitors Revealed by Co-crystal Structures and Kinetic Analysis. *Current Chemical Genomics* 4, 19-26 (2010); Jin, H., et al., Substituted 3-(4-(1,3,5-triazin-2-yl)-phenyl)-2-aminopropanoic Acids as Novel Tryptophan Hydroxylase Inhibitors. *Bioorganic & Medicinal Chemistry Letters* 19, 5229-32 (2009); Shi, Z. C., et al., Modulation of Peripheral Serotonin Levels by Novel Tryptophan Hydroxylase Inhibitors for the Potential Treatment of Functional Gastrointestinal Disorders. *Journal of Medicinal Chemistry* 51, 3684-7 (2008); Liu, Q., et al., Discovery and Characterization of Novel Tryptophan Hydroxylase Inhibitors That Selectively Inhibit Serotonin Synthesis in the Gastrointestinal Tract. *The Journal of Pharmacology and Experimental Therapeutics* 325, 47-55 (2008).

Spirocyclic compounds that act as inhibitors of THP and are useful in the treatment of various diseases and disorders associated with peripheral serotonin, including the cardiovascular diseases of pulmonary arterial hypertension (PAH) and associated pulmonary arterial hypertension (APAH) and carcinoid syndrome are known. (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate and (S)-8-(2-amino-6-((R)-1-(5-chloro-[1,1'-biphenyl]-2-yl)-2,2,2-trifluoroeth-oxy)pyrimidin-4-yl)-2,8-diazaspiro[4.5]decane-3-carboxylic acid are known compounds.

There is a need to selectively reduce tissue 5-HT (particularly intestinal 5-HT and lung 5-HT) levels as a means for treating and preventing 5-HT-associated diseases and modulation and/or reduction of serotonin levels, particularly peripheral serotonin levels, as well as 5-HIAA levels in the urine. There is also a need to achieve desirable $AUC_{0-tau}$ levels in the bloodstream. There is a more particular need to treat or prevent the cardiovascular diseases of pulmonary arterial hypertension (PAH) and associated pulmonary arterial hypertension (APAH).

SUMMARY OF THE DISCLOSURE

According to the present disclosure, there is provided a daily dosage regimen for treating pulmonary arterial hypertension. The regimen takes the form of two discrete dosage forms. Each dosage form includes an amount from about 600 mg to about 800 mg of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate.

Further according to the present disclosure, there is provided a daily dosage regimen for treating pulmonary arterial hypertension. The regimen has an amount from about 1200 mg to about 1600 mg of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate.

Also according to the present disclosure, there is provided a method for treating pulmonary arterial hypertension. The method has the step of administering to a human patient in need thereof an amount from about 1200 mg to about 1600 mg of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate per day.

Further according to the present disclosure, there is provided a method for reducing the level of serotonin biosynthesis by at least 50% in a human patient in need thereof within 14 days after commencement of treatment. The method has the step of administering to the human patient an amount from about 800 mg to about 1600 mg of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate per day.

Still further according to the present disclosure, there is provided a method for achieving an $AUC_{0-tau}$ of ≥2530 ng·hr/mL of (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid in a human patient within 14 days after commencement of administration. The method has the step of administering daily to the human patient an effective amount of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate.

According to the present disclosure, there is provided a method of achieving a >50% reduction in urinary 5-HIAA in a human patient within 14 days after commencement of administration. The method has the step of administering daily to a human patient an effective amount of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate.

Further according to the present disclosure, there is provided a method for treating pulmonary arterial hypertension. The method has the step of administering daily to a human patient in need thereof an amount of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate sufficient to achieve an $AUC_{0-tau}$ of ≤2530 ng·hr/mL of (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid within 14 days after commencement of administration.

According to the present disclosure, there is provided a method for treating pulmonary arterial hypertension. The method has the step of administering daily to a human patient in need thereof an amount of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate sufficient to achieve a >50% reduction in urinary 5-HIAA within 14 days after commencement of administration.

BRIEF DESCRIPTION OF THE DRAWINGS

Embodiments of the present disclosure are described herein with reference to the following figures.

Figure 1:
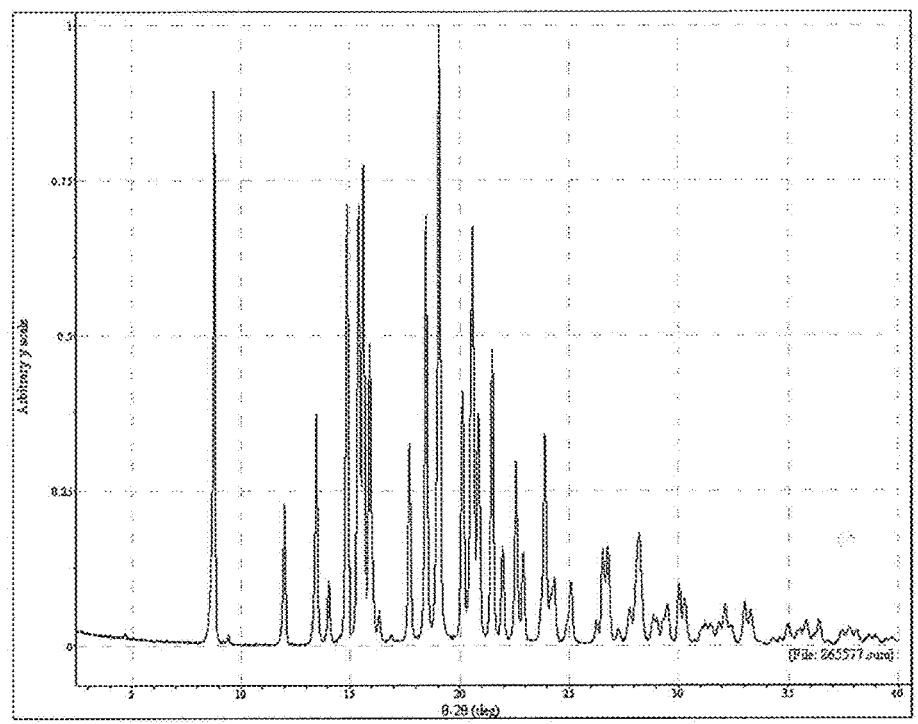
FIG. 1 is a plot of an XRPD of a crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate according to the present disclosure (crystalline Form 3).
Figure 2:
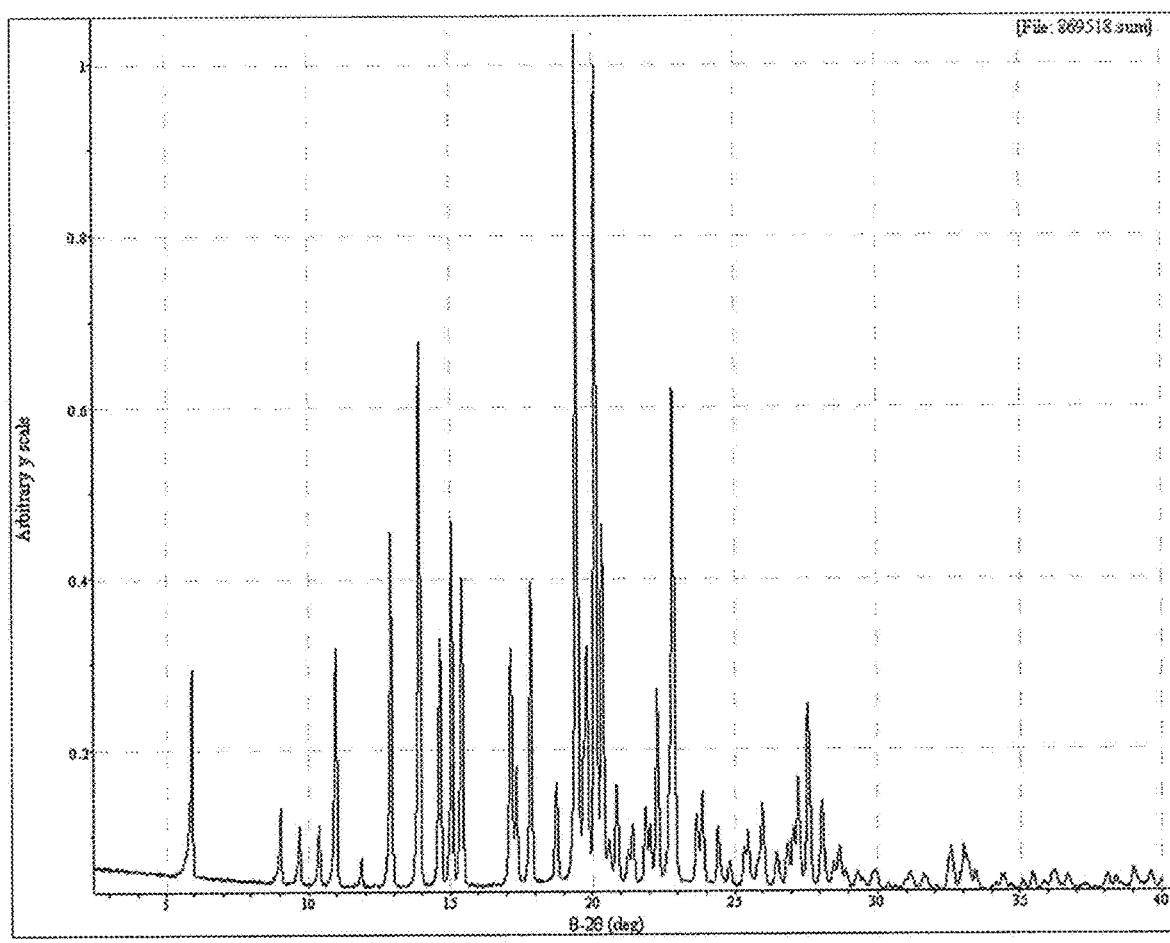
FIG. 2 is a plot of an XRPD of a crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate of a different polymorphic form than that of FIG. 1 (crystalline Form 1).
Figure 3A:
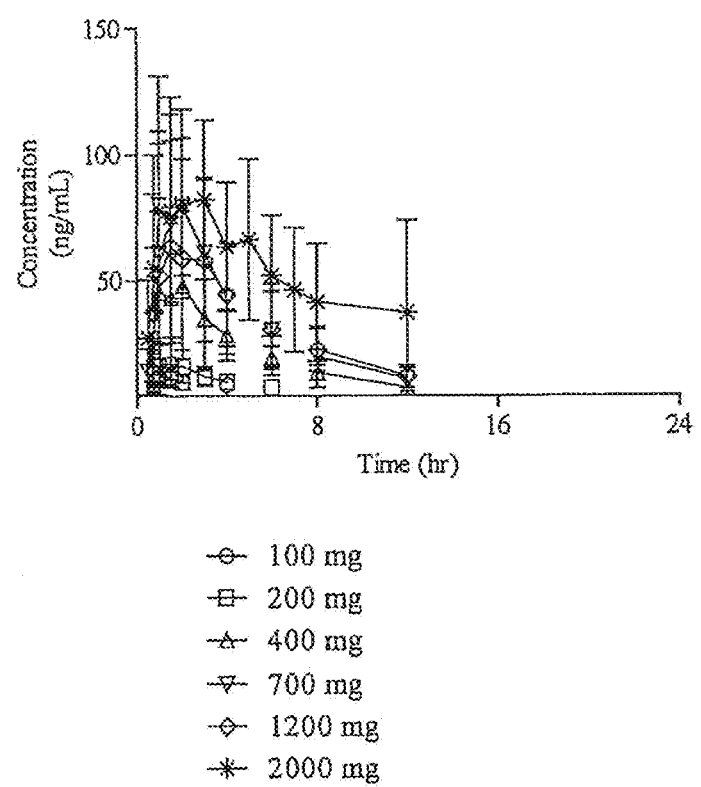
FIG. 3a is a plot of mean (±SD) plasma concentration-time profiles of KAR5585 following administration of 100-2000 mg of KAR5585 under fasting conditions—Cohorts 1-6 (linear scale).
Figure 3B:
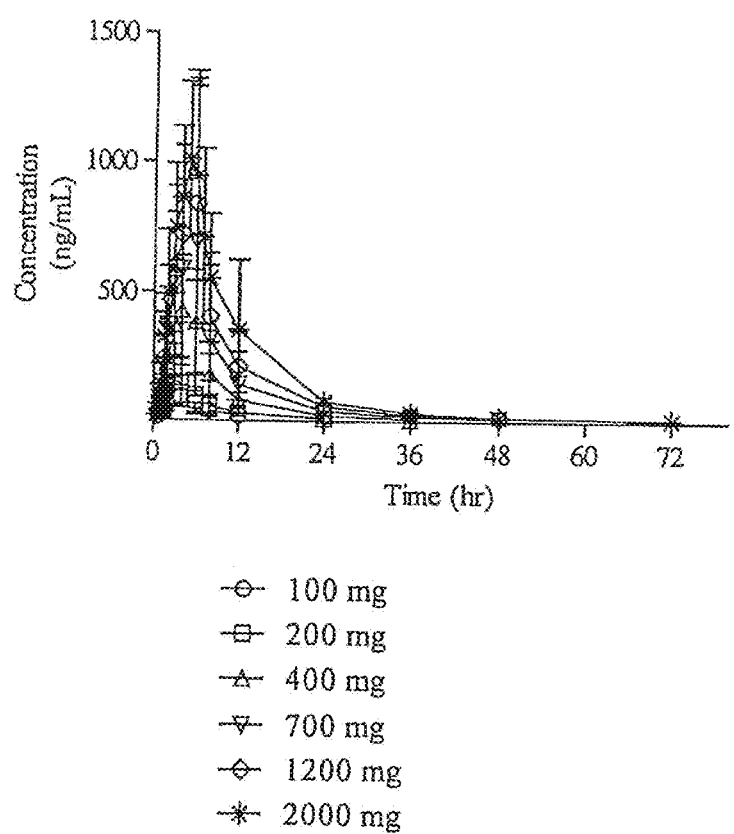
FIG. 3b is a plot of mean (±SD) plasma concentration-time profiles of KAR5417 following administration of 100-2000 mg of KAR5585 under fasting conditions—Cohorts 1-6 (linear scale) for KAR5417.
Figure 4A:
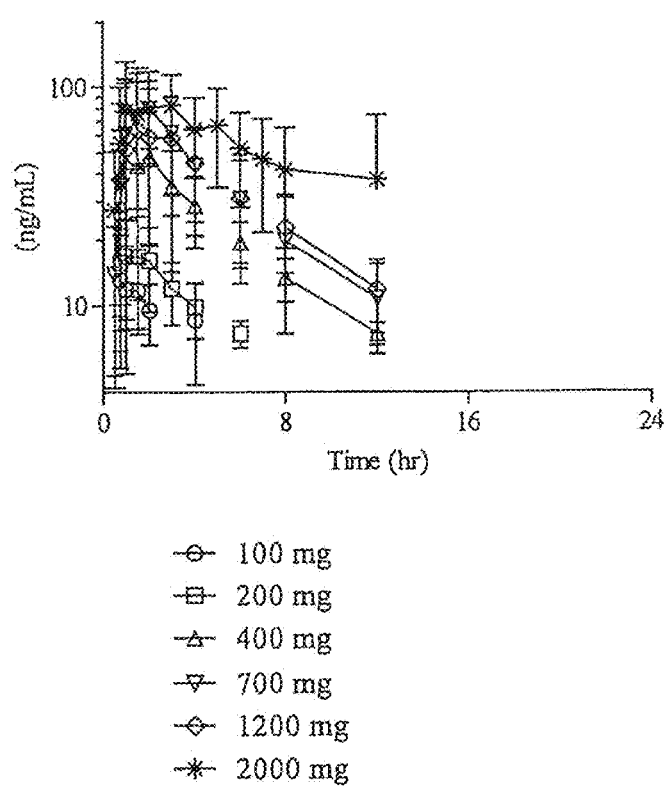
FIG. 4a is a plot of mean (±SD) plasma concentration-time profiles of KAR5585 and KAR5417 following administration of 100-2000 mg of KAR5585 under fasting conditions—Cohorts 1-6 (log scale) for KAR5585.
Figure 4B:
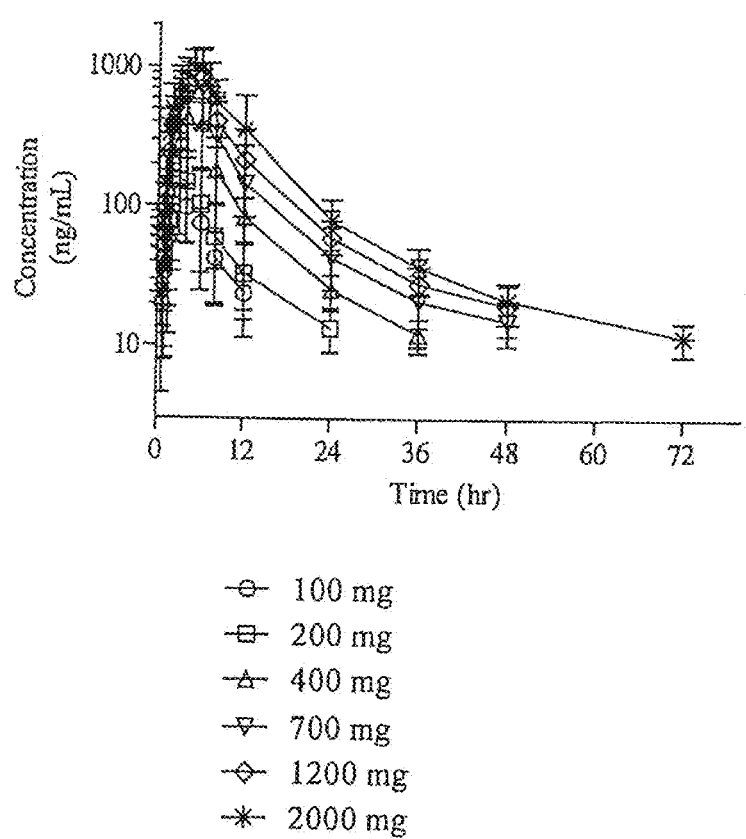
FIG. 4b is a plot of mean (±SD) plasma concentration-time profiles of KAR5585 and KAR5417 following administration of 100-2000 mg of KAR5585 under fasting conditions—Cohorts 1-6 (log scale) for KAR5417.
Figure 5A:
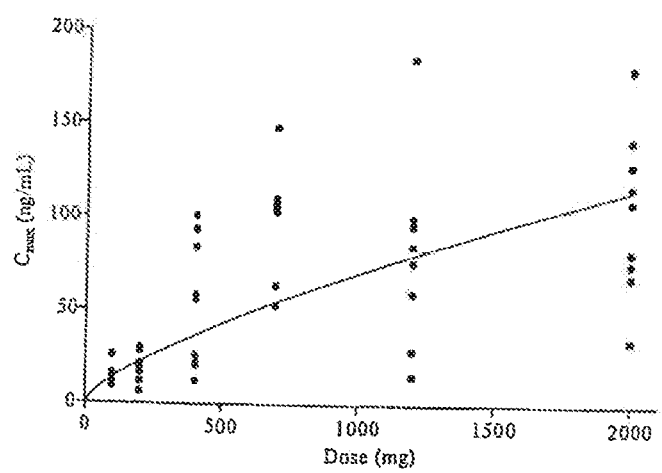
FIG. 5a is a plot of dose vs. plasma $C_{max}$ values for KAR5585 and KAR5417 in fasted healthy volunteers following a single oral dose of KAR5585.
Figure 5B:
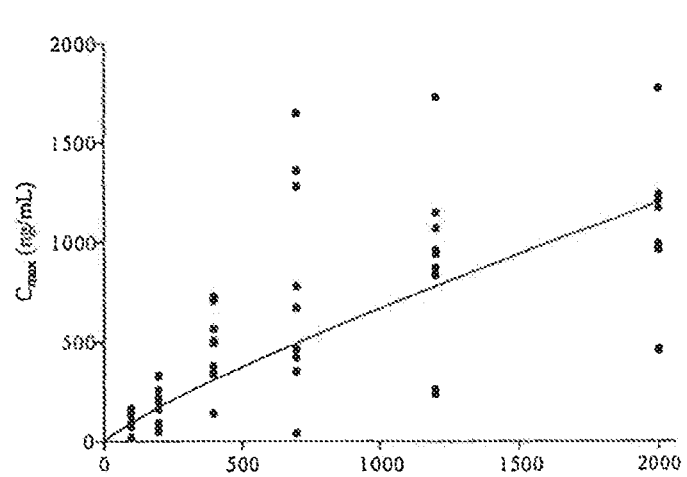
FIG. 5b is a plot of dose vs. plasma $C_{max}$ values for KAR5585 and KAR5417 in fasted healthy volunteers following a single oral dose of KAR5417.
Figure 6A:
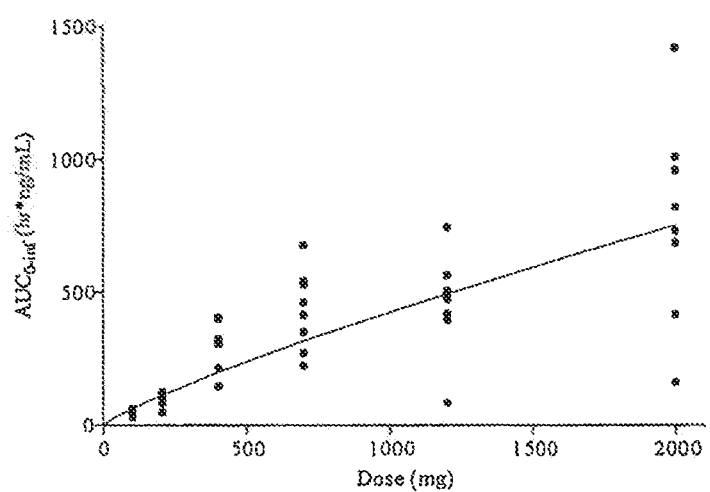
FIG. 6a is a plot of dose vs. plasma $AUC_{inf}$ values for KAR5585 and KAR5417 in fasted healthy volunteers following a single oral dose of KAR5585.
Figure 6B:
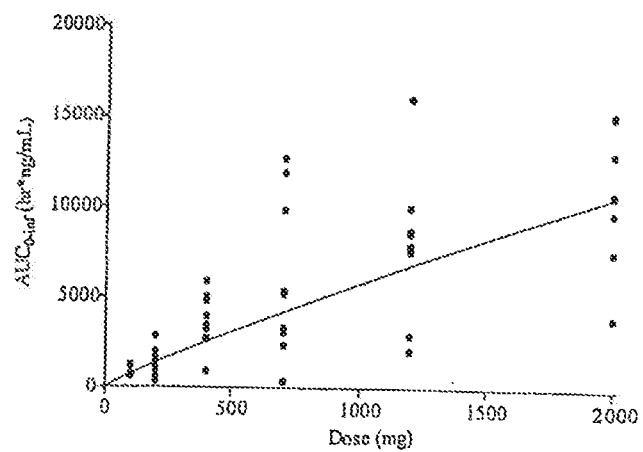
FIG. 6b is a plot of dose vs. plasma $AUC_{inf}$ values for KAR5585 and KAR5417 in fasted healthy volunteers following a single oral dose of KAR5585.

DETAILED DESCRIPTION OF THE DISCLOSURE (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate ("KAR5585") is a useful TPH1 inhibitor. The amorphous form of KAR5585 is disclosed at Example 63i of U.S. Pat. No. 9,199,994. KAR5585 has the following structure:

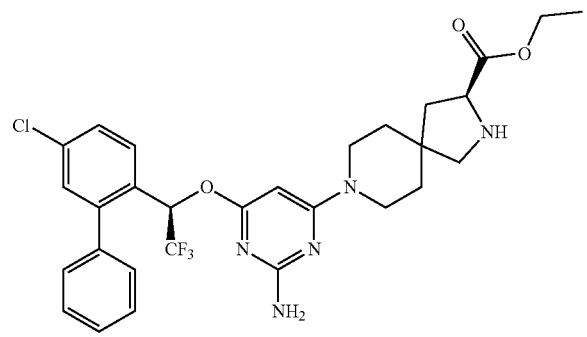 [SMILES: CCOC(=O)[C@@H]1CC2(CCN(c3cc(O[C@H](c4ccc(Cl)cc4-c4ccccc4)C(F)(F)F)nc(N)n3)CC2)CN1]

Two crystalline forms of KAR5585, i.e., polymorphs are known. One is denoted as "crystalline Form 3" and the other as "crystalline Form 1". Form 3 exhibits substantially greater thermodynamic stability compared to Form 1 and is supportive of longer shelf life, particularly at temperatures of less than 95° C. and more particularly at temperatures of less than 80° C.

The crystalline Form 3 exhibits the XRPD (X-ray powder diffraction) pattern set forth below in Table 1.

TABLE 1

Observed Peaks for X-ray Powder Diffraction Pattern for KAR5585, Form 3

| Peak position (°2θ) | d space (Å) | Intensity (%) |
|---|---|---|
| 8.78 ± 0.20 | 10.077 ± 0.235 | 90 |
| 12.00 ± 0.20 | 7.375 ± 0.125 | 25 |
| 13.47 ± 0.20 | 6.573 ± 0.099 | 39 |
| 14.02 ± 0.20 | 6.316 ± 0.091 | 12 |
| 14.87 ± 0.20 | 5.956 ± 0.081 | 71 |
| 15.39 ± 0.20 | 5.757 ± 0.075 | 72 |
| 15.61 ± 0.20 | 5.677 ± 0.073 | 78 |
| 15.89 ± 0.20 | 5.576 ± 0.071 | 50 |
| 16.31 ± 0.20 | 5.434 ± 0.067 | 7 |
| 17.70 ± 0.20 | 5.011 ± 0.057 | 34 |
| 18.45 ± 0.20 | 4.809 ± 0.052 | 70 |
| 19.05 ± 0.20 | 4.658 ± 0.049 | 100 |
| 20.12 ± 0.20 | 4.413 ± 0.044 | 42 |
| 20.57 ± 0.20 | 4.317 ± 0.042 | 68 |
| 20.84 ± 0.20 | 4.262 ± 0.041 | 39 |
| 21.46 ± 0.20 | 4.141 ± 0.039 | 49 |
| 21.94 ± 0.20 | 4.051 ± 0.037 | 18 |
| 22.56 ± 0.20 | 3.941 ± 0.035 | 31 |
| 22.90 ± 0.20 | 3.884 ± 0.034 | 17 |
| 23.90 ± 0.20 | 3.723 ± 0.031 | 35 |
| 24.32 ± 0.20 | 3.660 ± 0.030 | 13 |
| 25.07 ± 0.20 | 3.552 ± 0.028 | 12 |
| 26.54 ± 0.20 | 3.359 ± 0.025 | 17 |
| 26.76 ± 0.20 | 3.332 ± 0.025 | 18 |
| 27.79 ± 0.20 | 3.210 ± 0.023 | 8 |
| 28.21 ± 0.20 | 3.163 ± 0.022 | 19 |
| 29.48 ± 0.20 | 3.030 ± 0.020 | 9 |

TABLE 1-continued

Observed Peaks for X-ray Powder Diffraction Pattern for KAR5585, Form 3

| Peak position (°2θ) | d space (Å) | Intensity (%) |
|---|---|---|

In another aspect, Form 3 exhibits prominent XRPD peaks set forth below in Table 2.

TABLE 2

Prominent Observed Peaks for X-ray Powder Diffraction Pattern for KAR5585, Form 3

| Peak position (°2θ) | d space (Å) | Intensity (%) |
|---|---|---|
| 8.78 ± 0.20 | 10.077 ± 0.235 | 90 |
| 14.87 ± 0.20 | 5.956 ± 0.081 | 71 |
| 15.39 ± 0.20 | 5.757 ± 0.075 | 72 |
| 15.61 ± 0.20 | 5.677 ± 0.073 | 78 |
| 18.45 ± 0.20 | 4.809 ± 0.052 | 70 |
| 19.05 ± 0.20 | 4.658 ± 0.049 | 100 |

In yet another aspect, Form 3 exhibits a characteristic XRPD peak at 19.05±0.20 (° 2).

Crystalline Form 1 crystalline compound exhibits the XRPD (X-ray powder diffraction) pattern set forth below in Table 3.

TABLE 3

Observed Peaks for X-Ray Powder Diffraction Pattern for Form 1

| Peak position (°2θ) | d space (Å) | Intensity (%) |
|---|---|---|
| 5.92 ± 0.20 | 14.936 ± 0.522 | 27 |
| 9.01 ± 0.20 | 9.816 ± 0.222 | 11 |
| 9.68 ± 0.20 | 9.140 ± 0.192 | 9 |
| 10.38 ± 0.20 | 8.523 ± 0.167 | 9 |
| 10.95 ± 0.20 | 8.082 ± 0.150 | 30 |
| 11.85 ± 0.20 | 7.468 ± 0.128 | 6 |
| 12.90 ± 0.20 | 6.861 ± 0.108 | 43 |
| 13.89 ± 0.20 | 6.376 ± 0.093 | 65 |
| 14.62 ± 0.20 | 6.057 ± 0.084 | 31 |
| 15.04 ± 0.20 | 5.890 ± 0.079 | 44 |
| 15.41 ± 0.20 | 5.750 ± 0.075 | 38 |
| 17.13 ± 0.20 | 5.176 ± 0.061 | 30 |
| 17.83 ± 0.20 | 4.974 ± 0.056 | 37 |
| 18.72 ± 0.20 | 4.741 ± 0.051 | 14 |
| 19.44 ± 0.20 | 4.567 ± 0.047 | 100 |
| 19.79 ± 0.20 | 4.487 ± 0.045 | 30 |
| 20.11 ± 0.20 | 4.417 ± 0.044 | 97 |
| 20.34 ± 0.20 | 4.366 ± 0.043 | 44 |
| 20.84 ± 0.20 | 4.262 ± 0.041 | 14 |
| 21.41 ± 0.20 | 4.151 ± 0.039 | 10 |
| 21.88 ± 0.20 | 4.063 ± 0.037 | 11 |
| 22.28 ± 0.20 | 3.991 ± 0.036 | 25 |
| 22.83 ± 0.20 | 3.895 ± 0.034 | 60 |
| 23.85 ± 0.20 | 3.731 ± 0.031 | 13 |
| 24.40 ± 0.20 | 3.648 ± 0.030 | 9 |
| 25.45 ± 0.20 | 3.500 ± 0.027 | 9 |
| 25.97 ± 0.20 | 3.431 ± 0.026 | 12 |
| 27.22 ± 0.20 | 3.276 ± 0.024 | 15 |
| 27.58 ± 0.20 | 3.235 ± 0.023 | 23 |
| 28.06 ± 0.20 | 3.180 ± 0.022 | 12 |
| 28.66 ± 0.20 | 3.115 ± 0.021 | 7 |

In still another aspect, Form 1 exhibits prominent XRPD peaks set forth below in Table 4.

TABLE 4

Prominent Observed Peaks for X-Ray Powder
Diffraction Pattern for Compound 1, Form 1

| Peak position (°2θ) | d space (Å) | Intensity (%) |
| --- | --- | --- |
| 12.90 ± 0.20 | 6.861 ± 0.108 | 43 |
| 13.89 ± 0.20 | 6.376 ± 0.093 | 65 |
| 15.04 ± 0.20 | 5.890 ± 0.079 | 44 |
| 19.44 ± 0.20 | 4.567 ± 0.047 | 100 |
| 20.11 ± 0.20 | 4.417 ± 0.044 | 97 |
| 20.34 ± 0.20 | 4.366 ± 0.043 | 44 |
| 22.83 ± 0.20 | 3.895 ± 0.034 | 60 |

The amorphous form of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate can be prepared by the method set forth in Example 63i of U.S. Pat. No. 9,199,994, which is incorporated herein by reference in its entirety. The amorphous form can then be converted to crystalline form by methods described in U.S. Ser. No. 16/683,509, filed Nov. 14, 2019, which is incorporated herein by reference in its entirety. Forms 1 and 3 can be prepared by the methods set forth in U.S. Ser. No. 16/683,509.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The Form 3 compound can be used to inhibit the activity of the TPH1 enzyme in a cell by contacting the cell with an inhibiting amount of a compound of the disclosure. The cell can be part of the tissue of a living organism, or can be in culture, or isolated from a living organism. Additionally, the Form 3 compound can be used to inhibit the activity of the TPH1 enzyme in an animal, individual, or patient, by administering an inhibiting amount of a compound of the disclosure to the cell, animal, individual, or human patient.

The Form 3 compound can also lower peripheral serotonin levels in an animal, individual, or patient, by administering an effective amount of a compound of the disclosure to the animal, individual, or patient. In some embodiments, the Form 3 compound can lower levels of peripheral serotonin (e.g., 5-HT in the GI tract or lung tissue) selectively over non-peripheral serotonin (e.g., 5-HT in the CNS). In some embodiments, the selectivity can be 2-fold or more, 3-fold or more, 5-fold or more, 10-fold or more, 50-fold or more, or 100-fold or more.

As TPH1 inhibitors that can lower peripheral serotonin levels, the Form 3 compound is useful in the treatment and prevention of various diseases associated with abnormal expression or activity of the TPH1 enzyme, or diseases associated with elevated or abnormal peripheral serotonin levels. In some embodiments, the treatment or prevention includes administering to a patient in need thereof a therapeutically effective amount of a TPH1 inhibitor of the Form 3 compound. The Form 3 compound is also useful in the treatment and prevention of serotonin syndrome.

The efficacy of amorphous (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate in inhibiting TPH1 in mice was demonstrated in U.S. Pat. No. 9,199,994 in biological assays at Example 63i and Table 27.

Biological assays, some of which are described herein, can be used to determine the inhibitory effect of compounds against TPH (such as TPH1) in vitro and/or in vivo. In vitro biochemical assays for human, mouse, and rat TPH1 and human TPH2, PheOH, and TH may be used to measure inhibition of enzyme activity and the selectivity among TPH1, TPH2, PheOH, and TH. In addition, the efficacy of these compounds can be determined, for example, by measuring their effect on intestinal 5-HT levels in rodents after oral administration.

The metabolite of KAR5585 is (S)-8-(2-amino-6-((R)-1-(5-chloro-[1,1'-biphenyl]-2-yl)-2,2,2-trifluoroeth-oxy)pyrimidin-4-yl)-2,8-diazaspiro[4.5]decane-3-carboxylic acid, which is of the formula

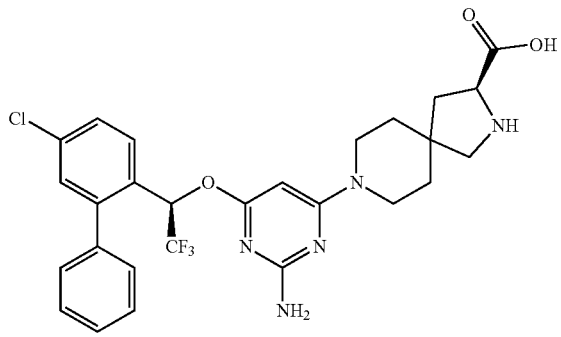 [SMILES: Nc1nc(O[C@H](c2ccc(Cl)cc2-c2ccccc2)C(F)(F)F)cc(N2CCC3(CC2)CN[C@H](C(=O)O)C3)n1]

(S)-8-(2-amino-6-((R)-1-(5-chloro-[1,1'-biphenyl]-2-yl)-2,2,2-trifluoroeth-oxy)pyrimidin-4-yl)-2,8-diazaspiro[4.5]decane-3-carboxylic acid is referred to herein as KAR5417. When KAR5585 enters the bloodstream, it substantially converts to KAR5417. The amorphous form of KAR5417 can be prepared by the method set forth in Example 34c of U.S. Pat. No. 9,199,994.

KAR5585 has been found to be particularly useful in treating and preventing pulmonary arterial hypertension (PAH). Prior studies have characterized treatment of PAH in rats, but there remains a need for efficacy and dosage to be characterized such that effective treatment of human adults can be carried out.

One aspect of the present disclosure is a daily dosage regimen for treatment of PAH in adults. The regimen takes the form of two discrete dosage forms. Each dosage form includes an amount from about 600 mg to about 800 mg of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate of Form 3. A preferred daily regimen employs two oral dosage forms taken twice per day (BID) up to 14 days. Another preferred aspect are dosage forms having 600 mg or 800 mg of KAR5585 (Form 3).

Another aspect of the dosage regimen for treating pulmonary arterial hypertension is administration of an amount from about 1200 mg to about 1600 mg of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate per day.

Another aspect of the present disclosure is a method for reducing the level of serotonin (5-HT) biosynthesis by at least 50% in a human patient within 14 days after commencement of treatment. The method has the step of administering to the human patient about 800 mg to about 1600 mg of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro

[4.5]decane-3-carboxylate per day. Serotonin levels are determined by the methods disclosed in the examples below.

Another aspect of the present disclosure is treatment of pulmonary arterial hypertension by achievement an $AUC_{0\text{-}tau}$ of $\geq 2530$ ng·hr/mL of (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid in a human patient within 14 days after commencement of administration of a sufficient amount to the human patient. A preferred level of $AUC_{0\text{-}tau}$ of $\geq 2530$ ng·hr/mL. $AUC_{0\text{-}tau}$ is determined by methods disclosed in the examples below.

Another aspect of the present disclosure is treatment of pulmonary arterial hypertension by achievement of a >50% reduction in urinary 5-HIAA in a human patient within 14 days after commencement of administration of a sufficient amount to the human patient. Urinary 5-HIAA is determined by methods disclosed in the examples below.

Other diseases treatable or preventable by administering a TPH1 inhibitor of the disclosure include bone disease such as, for example, osteoporosis, osteoporosis pseudoglioma syndrome (OPPG), osteopenia, osteomalacia, renal osteodystrophy, Paget's disease, fractures, and bone metastasis, In some embodiments, the disease is osteoporosis, such as primary type 1 (e.g., postmenopausal osteoporosis), primary type 2 (e.g., senile osteoporosis), and secondary (e.g., steroid- or glucocorticoid-induced osteoporosis).

Further diseases treatable or preventable by the methods of the disclosure include cardiovascular diseases such as atherosclerosis and pulmonary hypertension (PH), including idiopathic or familial PH, and including PH associated with or brought on by other diseases or conditions. In some embodiments, the PH disease is pulmonary arterial hypertension (PAH).

The types of PAH treatable according to the methods of the disclosure include (1) idiopathic (IPAH), (2) familial (FPAH), and (3) associated (APAH) which is the most common type of PAH. The latter is PAH which is associated with other medical conditions including, for example, (1) collagen vascular disease (or connective tissue disease) that include autoimmune diseases such as scleroderma or lupus; (2) congenital heart and lung disease; (3) portal hypertension (e.g., resulting from liver disease); (4) HIV infection; (5) drugs (e.g., appetite suppressants, cocaine, and amphetamines; and (6) other conditions including thyroid disorders, glycogen storage disease, Gaucher disease, hereditary hemorrhagic telangiectasia, hemoglobinopathies, myeloproliferative disorders, and splenectomy. APAH can also be PAH associated with abnormal narrowing in the pulmonary veins and/or capillaries such as in pulmonary veno-occlusive disease (PVOD) and pulmonary capillary hemangiomatosis. Another type of PAH is associated with persistent pulmonary hypertension of the newborn (PPHN).

Further diseases treatable or preventable by the methods of the present disclosure include metabolic diseases such as diabetes and hyperlipidemia; pulmonary diseases such as chronic obstructive pulmonary disease (COPD), and pulmonary embolism; gastrointestinal diseases such as IBD, colitis, chemotherapy-induced emesis, diarrhea, carcinoid syndrome, celiac disease, Crohn's disease, abdominal pain, dyspepsia, constipation, lactose intolerance, MEN types I and II, Ogilvie's syndrome, pancreatic cholera syndrome, pancreatic insufficiency, pheochromacytoma, scleroderma, somatization disorder, Zollinger-Ellison Syndrome, or other gastrointestinal inflammatory conditions; liver diseases such as chronic liver disease; cancers such as liver cancer, breast cancer, cholangiocarcinoma, colon cancer, colorectal cancer, neuroendocrine tumors, pancreatic cancer, prostate cancer, and bone cancer (e.g., osteosarcoma, chrondrosarcoma, Ewings sarcoma, osteoblastoma, osteoid osteoma, osteochondroma, enchondroma, chondromyxoid fibroma, aneurysmal bone cyst, unicameral bone cyst, giant cell tumor, and bone tumors); blood diseases (e.g., myeloproliferative syndrome, myelodysplasia syndrome, Hodgkin's lymphoma, non-Hodgkin's lymphoma, myeloma, and anemia such as aplastic anemia and anemia associated with kidney disease; and blood cancers (e.g., leukemias such as acute lymphocytic leukemia (ALL), chronic lymphocytic leukemia (CLL), acute myeloid leukemia (AML), and chronic myeloid leukemia (CML)).

A further treatable disease is the treatment and prevention of carcinoid syndrome. Carcinoid syndrome is a paraneoplastic syndrome exhibiting the signs and symptoms that occur secondary to carcinoid tumors. Carcinoid syndrome is caused by a carcinoid tumor that secretes serotonin or other hormones into the bloodstream. Carcinoid tumors usually occur in the gastrointestinal tract, including the stomach, appendix, small intestine, colon, and rectum or in the lungs. Common symptoms include skin flushing, facial skin lesions, diarrhea, irritable bowel syndrome, cramping, difficulty breathing, and rapid heartbeat.

In some embodiments, the present disclosure includes methods of lowering plasma cholesterol, lowering plasma triglycerides, lowering plasma glycerol, lowering plasma free fatty acids in a patient by administering to said patient a therapeutically effective amount of a compound of the disclosure.

KAR5585 is also useful in the treatment and prevention of inflammatory disease, such as allergic airway inflammation (e.g., asthma).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the enzyme with a compound of the disclosure includes the administration of a compound of the present disclosure to an individual or patient, such as a human, having the TPH1 enzyme, as well as, for example, introducing a compound of the disclosure into a sample containing a cellular or purified preparation containing the TPH1 enzyme.

As used herein, the term "individual" or "patient" used interchangeably, refers to any animal, including mammals, preferably mice, rats, other rodents, rabbits, dogs, cats, swine, cattle, sheep, horses, or primates, and, most preferably, humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology) or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" refers to inhibiting onset or worsening of the disease; for example, in an individual who may be predisposed to the disease, condition or disorder but does not yet experience or display the pathology or symptomatology of the disease.

KAR5585 can be administered to human patients in need of such treatment in appropriate dosages that will provide prophylactic and/or therapeutic efficacy. The dose required for use in the treatment or prevention of any particular disease or disorder will typically vary from patient to patient depending on, for example, particular compound or composition selected, the route of administration, the nature of the condition being treated, the age and condition of the patient, concurrent medication or special diets then being followed by the patient, and other factors. The appropriate dosage can be determined by the treating physician.

KAR5585 can be administered orally, subcutaneously, topically, parenterally, by inhalation spray or rectally in dosage unit formulations containing pharmaceutically acceptable carriers, adjuvants and vehicles. Parenteral administration can involve subcutaneous injections, intravenous or intramuscular injections or infusion techniques. Treatment duration can be as long as deemed necessary by a treating physician. The compositions can be administered one to four or more times per day. A treatment period can terminate when a desired result, for example, a particular therapeutic effect, is achieved. Alternatively, a treatment period can be continued indefinitely.

In some embodiments, the pharmaceutical compositions can be prepared as solid dosage forms for oral administration (e.g., capsules, tablets, pills, dragees, powders, granules and the like). A tablet can be prepared by compression or molding. Compressed tablets can include one or more binders, lubricants, glidants, inert diluents, preservatives, disintegrants, or dispersing agents. Tablets and other solid dosage forms, such as capsules, pills and granules, can include coatings, such as enteric coatings.

Solid and liquid dosage forms can be formulated so that they conform to a desired release profile, e.g., immediate release, delayed release, and extended or sustained release.

The amount of KAR5585 to be administered will vary depending on factors such as the following: method of administration, release profile, and composition formulation. Typically, for KAR5585 in an oral dosage form to treat or prevent a disease, particularly PH/PAH/APAH/IPAH/FPAH, a typical dosage will be about 1 mg/kg/day to about 50 mg/kg/day and more typically from about 5 mg/kg/day to about 30 mg/kg/day, based on the weight of the patient. A most preferred active is Form 3. Individual oral dosage forms typically have from about 50 mg to about 3000 mg of KAR5585 and additional amounts of one or more pharmaceutically acceptable excipients. Other useful individual oral dosage forms can, by way of example, have KAR5585 in amounts of 100 mg, 150 mg, 200 mg, 250 mg, 300 mg, 350 mg, or 400 mg, 450 mg, 500 mg, 550 mg, 575 mg, 600 mg, 625 mg, 650 mg, 675 mg, 700 mg, 725 mg, 750 mg, 775 mg, 800 mg, 900 mg, 950 mg, 1000 mg, 1050 mg, 1100 mg, 1150 mg, and about 1200 mg. Other amounts between 50 mg to 3000 mg are possible, for example, from about 325 mg to about 475 mg, from about 350 mg to about 500 mg, from about 375 mg to about 525 mg, from about 400 mg to about 550 mg, from about 425 mg to about 575 mg, from about 450 mg to about 600 mg, from about 475 mg to about 625 mg, from about 500 mg to about 650 mg, from about 525 mg to about 675 mg, from about 550 mg to about 700 mg, from about 575 mg to about 725 mg, from about 600 mg to about 750 mg, from about 625 mg to about 775 mg, from about 650 mg to about 800 mg, from about 675 mg to about 825 mg, from about 700 mg to about 850 mg, from about 725 mg to about 875 mg, from about 750 mg to about 900 mg, from about 775 mg to about 925 mg, from about 800 mg to about 950 mg, from about 825 to about 975, from about 850 mg to about 1000 mg, from about 900 mg to about 1150 mg, from about 1000 mg to about 1150 mg, from about 1100 mg to about 1250 mg, from about 1200 mg to about 1350 mg, and from about 1200 mg to about 1350 mg. Particularly preferred dosage regimens are 600 mg to 800 mg twice per day (BID). Especially preferred regimen embodiments are 600 mg BID and 800 mg BID.

"wt %" means weight percent based on the total weight of the composition or formulation.

Preferred dosage forms have the crystalline compound of Form 3 present in a proportion that is 90 wt % or more, and more preferably 95 wt % or more, by weight of any (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate present.

Dosage forms have the crystalline compound of Form 3 therein in any amount or proportion. Typical proportions include about 20 wt % or more, about 60 wt % or more, and about 90 wt % or more, based on the total weight of the dosage form (with the balance predominantly excipients, carriers, and vehicles). Particularly useful proportions are 25 wt % and 60 wt %.

Compositions for inhalation or insufflation include solutions and suspensions in pharmaceutically acceptable aqueous or organic solvents, or mixtures thereof, and powders. Liquid dosage forms for oral administration can include, for example, pharmaceutically acceptable emulsions, microemulsions, solutions, suspensions, syrups and elixirs. Suspensions can include one or more suspending agents.

Dosage forms for transdermal administration of a subject composition include powders, sprays, ointments, pastes, creams, lotions, gels, solutions and patches.

The Form 3 compound and compositions containing same can be administered in the form of an aerosol, which can be administered, for example, by a sonic nebulizer.

Pharmaceutical compositions suitable for parenteral administration can include the Form 3 compound together with one or more pharmaceutically acceptable sterile isotonic aqueous or non-aqueous solutions, dispersions, suspensions or emulsions.

Alternatively, the composition can be in the form of a sterile powder which can be reconstituted into a sterile injectable solutions or dispersion just prior to use.

The disclosure is further illustrated herein by the following non-limiting examples.

Examples

TABLE 5

Abbreviations used in the examples include the following:

| Abbreviation | Explanation |
|---|---|
| % CV | percent coefficient of variation |
| β-hCG | beta human chorionic gonadotropin |
| 5-HIAA | 5-hydroxyindoleacetic acid |
| 5-HT | 5-hydroxytryptamine (serotonin) |
| Adjusted | the 5-HIAA measured in urine during 24 hours, adjusted |

TABLE 5-continued

Abbreviations used in the examples include the following:

| Abbreviation | Explanation |
|---|---|
| urine 5-HIAA | for the mean 24-hour creatinine excretion on Days 1, 7, and 14 |
| AE | adverse event |
| AESI | adverse event of special interest |
| ALP | alkaline phosphatase |
| ALT | alanine aminotransferase |
| AST | aspartate aminotransferase |
| AUC | area under the concentration versus time curve |
| $AUC_{0-12}$ | area under the concentration versus time curve from time 0 to 12 hours after dosing, computed using the trapezoidal rule |
| $AUC_{0-24}$ | area under the concentration versus time curve from time 0 to 24 hours after dosing, computed using the trapezoidal rule |
| $AUC_{0-inf}$ | area under the concentration versus time curve from time 0 extrapolated to infinity |
| $AUC_{0-tau}$ | area under the concentration-time curve from time 0 to time of last quantifiable concentration |
| BID | twice daily (from Latin, bis in die) |
| BILI | bilirubin |
| BLQ | below the lower limit of quantitation |
| BMI | body mass index |
| BP | blood pressure |
| $C_{12\,hr}$ | concentration, obtained 12 hr after an administered dose |
| $C_{max}$ | maximum (or peak) serum concentration |
| $C_{min}$ | minimum serum concentration |
| CI | confidence interval |
| CL/F | apparent oral clearance |
| CRO | contract research organization; Ce3, Inc. |
| CRU | clinical research unit |
| ddHR | placebo-adjusted mean change from Baseline in heart rate |
| ddQTcF | placebo-adjusted mean change from Baseline in QTcF |
| ECG | electrocardiogram |
| eCRF | electronic case report form |
| Estimated urine 5-HIAA | the 5-HIAA measured in urine during 24 hours, corrected for the estimated creatinine excretion based on subject weight, age, gender, and race |
| FDA | Food and Drug Administration |
| GCP | Good Clinical Practice |
| GGT | gamma-glutamyl transpeptidase |
| Geo. | geometric |
| Hg | millimeters of mercury |
| HR | heart rate |
| ICF | informed consent form |
| ICH | International Council for Harmonisation of Technical Requirements for Pharmaceuticals for Human Use |
| IRB | Institutional Review Board |
| IUD | intrauterine device |
| KAR5417 | an active metabolite of the investigational product KAR5585 |
| KAR5585 | the investigational product; it is a prodrug of KAR5417 |
| LDH | lactate dehydrogenase |
| Max | maximum |
| Measured urine 5-HIAA | the 5-HIAA measured in urine during 24 hours, without adjustment for daily variations in creatinine excretion |
| MedDRA | Medical Dictionary for Regulatory Activities |
| Min | minimum |
| MOA | mechanism of action |
| N, n | number |
| OAE | other significant adverse event |
| OTC | over the counter |
| PAH | pulmonary arterial hypertension |
| Param. | parameter |
| PCS | potentially clinically significant |
| PD | pharmacodynamics(s) |
| PI | Principal Investigator; the investigator who leads the study conduct at an individual study center. Every study center has a PI. |
| PK | pharmacokinetic(s) |
| PT | preferred term |
| QD | once daily (from Latin, quaque die) |
| QTcF | QT interval corrected for heart rate by applying Fridericia's formula; the unit for QTcF is milliseconds (msec) |
| $R_{AUC0-12}$ | accumulation ratio for $AUC_{0-12}$ |
| $R_{CMAX}$ | accumulation ratio for $C_{max}$ |
| SAE | serious adverse event |
| SAP | Statistical Analysis Plan |
| SD | standard deviation |
| SOC | system organ class |
| Stat. | statistical |
| SRC | Safety Review Committee |
| Study drug | investigational product, reference product (placebo), or both |
| $t_{1/2}$ | apparent terminal half-life after oral administration |
| TEAE | treatment-emergent adverse event |
| $t_{max}$ | time of maximum observed concentration |
| TPH1 | tryptophan hydroxylase 1 |
| Urine 5-HIAA/ 24 hours/g creatinine | urine 5-HIAA/24 hours divided by corresponding total creatinine (gram) measured/24 hours |
| WHODD | World Health Organization Drug Dictionary |

Methodology:

Study KAR5585-101 was a first-in-human, Phase 1, randomized, double-blind, placebo-controlled, single-center trial conducted in 2 parts to assess the safety, tolerability, PK, cardiac conduction, and biomarkers of target engagement effects of single ascending doses (SAD, Part 1) and multiple ascending doses (MAD, Part 2) of KAR5585 in healthy adult subjects. Food effect was to be evaluated in Part 1, Period 2. Part 2 was permitted to begin before Part 1 was completed and, in each part, the data from each dose Cohort were to be reviewed for safety before the next dose Cohort was enrolled.

The KAR5585 administered doses were the following:
In Part 1 (SAD) Period 1 (fasting): 100 mg, 200 mg, 400 mg, 700 mg, 1200 mg, or 2000 mg or matching placebo in Cohorts 1 through 6, respectively
In Part 1 (SAD) Period 2 (fed, high-fat food effect): 400 mg in Cohort 3 only
In Part 2 (MAD): 100 mg (fasting), 100 mg (fed), 200 mg (fed), and 400 mg (fed) or matching placebo administered twice daily (BID) approximately every 12 hours for 27 doses in Cohorts 1 through 4, respectively.
Doses of KAR5585 and placebo were to be administered orally in a capsule dosage form. Active drug capsules containing KAR5585 were provided in 50, 200, and 300 mg strengths; thus, more than 1 capsule was required to achieve some of the study doses.

Number of Patients (Planned and Analyzed):

Enrollment of 60 adult subjects (5 Cohorts of 12 subjects each) was originally planned in each part. In addition, up to 2 Cohorts of 12 subjects each may have been added to either or both parts, if necessary, based upon safety and PK data from the previous Cohorts, for a total of up to 168 subjects participating in the trial. Subjects were allowed to participate in Part 1 or Part 2, but not in both parts.

Part 1 had 6 Cohorts of 12 subjects each (for a total of 72 subjects) and Part 2 had 4 Cohorts of 12 subjects each (for a total of 48 subjects). In Part 1, the 12 subjects in Cohort 3 (400 mg) were studied twice, once under fasting conditions (Period 1) and once under fed conditions (Period 2) for food-effect assessment.

Test Product, Dose and Mode of Administration, Batch Number:

KAR5585, 50, 200 and 300 mg oral capsules administered as single doses of 100 mg, 200 mg, 400 mg, 700 mg, 1200 mg or 2000 mg (Part 1) or multiple doses of 100 mg, 200 mg or 400 mg every 12 hours for 14 days (27 doses)

(Part 2). Batches were Batch PID-19JUL15-111 (50 mg), PID-19JUL15-110 (200 mg), PID-19JUL15-109 (300 mg)

Duration of Treatment:

Part 1 (SAD): Single dose under fasted conditions; subjects included in the fed Cohort were to receive a second dose of KAR5585 (same dose level) or placebo.

Part 2 (MAD): BID doses (separated by approximately 12 hours on Days 1 to 13) and a single AM dose on Day 14. One or more of the MAD Cohort could have been dosed once daily (QD).

Reference Therapy, Dose and Mode of Administration, Batch Number:

Placebo, oral capsules. Batch PID-19JUL15-108 (matching 50 mg); PID-19JUL15-107 (matching 200 mg and 300 mg)

Pharmacokinetics:

Pharmacokinetic characteristics of KAR5585 and KAR5417 were to be evaluated in Parts 1 and 2 by measuring drug concentrations in plasma and urine and calculating PK parameters.

Biomarkers:

Biomarkers were to be evaluated in Part 2 by measuring concentrations of serotonin (5-hydroxytryptamine [5-HT]) in serum and 5-hydroxyindoleacetic acid (5-HIAA) in plasma and urine. As well, the relationship of biomarkers to PK parameters was to be evaluated.

Biomarker Analysis:

The biomarker analysis was to be based on the Biomarker Population (all subjects with evaluable biomarker measurements at baseline [Day 1 predose] and at least one after dosing [Day 7 or Day 14]). For analyses focused on the relationship between the PK parameters area under the concentration versus time curve (AUC) computed using the trapezoidal rule from time 0 to 24 hours after dosing ($AUC_{0-24}$), minimum observed concentration ($C_{min}$), and maximum observed concentration ($C_{max}$), and biomarkers, only subjects who had all biomarkers and these PK parameters assessed were to be included.

Biomarker data were to be collected only in Part 2. The following biomarkers were to be analyzed:

Serum 5-HT

Plasma 5-HIAA

Urine 5-HIAA/24 hours (as measured, adjusted, estimated, and per gram creatinine)

The a priori primary biomarker endpoint was to be the change in plasma 5-HIAA concentration on Day 14 from Day 1. The null hypothesis to be tested was that there was no difference between the change from Day 1 predose to Day 14 between placebo and KAR5585.

Linear regression was to be performed using biomarker changes, absolute and relative (%), from Day 1, at predose on Day 7 or Day 14 versus $AUC_{0-24}$, $C_{max}$, and $C_{min}$ in corresponding study days. The slopes and corresponding 95% confidence intervals (CIs) were to be tabulated.

Summary statistics (mean, standard deviation [SD], median, minimum [Min], and maximum [Max]) were to be tabulated for each biomarker, by Cohort, with absolute and relative (%) changes from Day 1 predose. Corresponding time course plots of the mean measurement for each biomarker were to be displayed graphically. The time course for each individual subject, by Cohort, was also to be displayed graphically.

For each biomarker, least mean squared differences and the corresponding 95% CIs were to be estimated for change from baseline between KAR5585 treatment groups and placebo at Day 7 or Day 14. The values were to be tabulated with P values testing whether the difference of changes was equal to 0.

Absolute and relative changes in each biomarker at Day 7 and Day 14 from Day 1 predose versus $AUC_{0-24}$, $C_{max}$, and $C_{min}$ were to be displayed graphically.

Blood and urine sample collection details for biomarker analysis and the biomarker concentrations were to be listed.

Pharmacokinetic Analysis:

The PK analysis was to be based on the PK Concentration Population (all subjects receiving active study medication and having any measurable plasma concentration of study medication at any time point) and the PK Evaluable Population (all subjects with sufficient KAR5585 and KAR5417 concentration-time data to support PK analysis). Pharmacokinetic data were to be summarized descriptively.

SUMMARY—CONCLUSIONS

Pharmacokinetics Results:

Part 1 SAD PK:

KAR5585 is a prodrug for the active tryptophan hydroxylate 1 (TPH1) inhibitor KAR5417. Following KAR5585 administration, KAR5585 was rapidly absorbed. The median time of maximum observed concentration ($t_{max}$) ranged between 1.5 and 3 hours postdose. Following administration of KAR5585, KAR5417 appeared rapidly in plasma, an observation consistent with rapid absorption of KAR5585 and efficient conversion to KAR5417.

The mean extent of systemic exposure to the active TPH1 inhibitor, KAR5417, as measured by mean $AUC_{0-24}$ and AUC from time 0 extrapolated to infinity ($AUC_{0-inf}$), appeared to increase in a dose-proportional manner between the 100 and 700 mg dose levels, with a 6.3-fold and 6.8-fold increase in mean $AUC_{0-24}$ and mean $AUC_{0-inf}$ estimates, respectively, for a 7-fold increase in dose between the 100 mg dose and the 700 mg dose. At doses greater than 700 mg, there were less than dose-proportional increases in $AUC_{0-24}$ and $AUC_{0-inf}$ values, with a 1.7-fold and 1.81-fold increase over the 2.86-fold increase in dose between 700 mg and 2000 mg. The mean apparent terminal half-life ($t_{1/2}$) after oral administration of KAR5417 increased with increasing dose levels studied, and ranged between 4.7 hours (100 mg dose) and 22.6 hours (2000 mg dose) after oral administration of KAR5585.

Administration of KAR5585 under fed conditions increased the extent and peak of exposure of both KAR5585 and KAR5417, with KAR5417 mean AUC from time 0 extrapolated to infinity ($AUC_{0-inf}$) increasing 1.8-fold from 3650 ng·hr/mL to 6710 ng·hr/mL and $C_{max}$ increasing 1.8-fold from 485 ng/mL to 860 ng/mL, under fasting and fed conditions, respectively. This was considered to be a clinically relevant change in exposure.

Part 2 MAD PK

KAR5585 was rapidly absorbed following oral administration.

Overall, the mean extent of systemic exposure to KAR5417, as measured by mean AUC from time 0 to 12 hours after dosing ($AUC_{0-12}$) and mean $AUC_{0-24}$, appeared to be comparable under fasted conditions (Part 2, Cohort 1; Day 1 $AUC_{0-12}$=741 hr*ng/mL; Day 14 $AUC_{0-24}$=1650 hr*ng/mL) relative to fed conditions (Part 2, Cohort 2; Day 1 $AUC_{0-12}$=470 hr*ng/mL; Day 14 $AUC_{0-24}$=1220 hr*ng/mL). This observation is in contrast to the food-effect comparison in Part 1, Cohort 3A and 3B KAR5585 400 mg).

In Part 1, a high-fat, high-calorie meal resulted in $AUC_{0-inf}$ of KAR5417 that was approximately 1.8-fold higher following drug administration of KAR5585 400 mg under fed conditions ($AUC_{0-inf}$=6710 ng·hr/mL) relative to fasting conditions ($AUC_{0-inf}$=3650 ng·hr/mL).

Steady-state plasma levels of KAR5417 were achieved by Day 7 as assessed by comparison of Day 7 and Day 14 $AUC_{0-12}$ and concentration obtained 12 hours after an administered dose ($C_{12hr}$) values following BID oral administration of KAR5585 for 14 days. Accumulation ratios for KAR5417 compared accumulation ratio for $C_{max}$ ($R_{Cmax}$) and accumulation ratio for $AUC_{0-12}$ ($R_{AUC0-12}$) for Day7/Day 1 and Day 14/Day 1, and verified that steady-state was achieved by Day 7. The $R_{AUC0-12}$ values for KAR5417 ranged from 2.19-2.57, 1.09-1.34 and 1.65-2.38 for the 100 mg, 200 mg, and 400 mg doses of KAR5585, respectively, suggesting that the PK of KAR5417 was independent of time, and that steady-state was achieved on Day 7 following repeated BID administration for 14-days.

Biomarker Results:

Dose- and time-dependent reductions were observed in 5-HIAA (a PD marker of 5-HT synthesis) in both plasma and urine. At the highest KAR5585 dose, 400 mg, mean percent change in plasma 5-HIAA concentration was 53.33 from Day 1 to Day 14, whereas mean percent change in subjects randomized to placebo was +20.12. Mean differences of both absolute and percent changes from Day 1 to Day 14 in plasma 5-HIAA concentration were statistically significant in favor of KAR5585 compared to placebo in each dose group and for all doses combined at Day 14.

There was a strong association between urine 5-HIAA/24 hours and KAR5585 dose. At the highest KAR5585 dose, 400 mg, mean percent change in measured urine 5-HIAA was 050.85 from Day 1 to Day 14, whereas mean percent change in subjects randomized to placebo was +3.97. Mean differences of absolute and relative changes from Day 1 to day 14 were statistically significant in favor of KAR5585 in all dose groups except one (the relative change on Day 14 for the KAR5585 100 mg fasting dose group). Results were comparable in urine 5-HIAA/24 hours as adjusted, estimated, and per gram creatinine.

A strong relationship was seen between KAR5417 exposure and 5-HIAA reductions. A strong relationship between both plasma and urine 5-HIAA is supported by the observation that higher exposure to KAR5417, as measured by the PK parameters $AUC_{0-24}$, $C_{max}$, $C_{12}$, and $AUC_{0-12}$, was associated with greater reduction in 5-HIAA.

Safety Results:

Part 1, SAD, Period 1—Fasting Administration

KAR5585, administered as a single ascending oral dose (100 mg, 200 mg, 400 mg, 700 mg, 1200 mg or 2000 mg), was safe and well-tolerated in 54 healthy adult subjects.

Part 1, SAD, Period 2—Fed Administration (Food Effect):

KAR5585 400 mg, administered as a single oral dose under fed conditions, was well-tolerated in 9 healthy adult subjects.

Part 2, MAD—Fasting and Fed Administration:

KAR5585, administered as multiple ascending oral doses of 100 mg (fasting), 100 mg (fed), 200 mg (fed), and 400 mg (fed), BID for up to 14 days (27 doses), was safe and well-tolerated in 36 healthy adult subjects. One or more of the MAD Cohorts could have been dosed QD, but none was.

CONCLUSION

No safety, tolerability, PK, or cardiac-conduction concerns were identified during the course of the study. The administration of KAR5585 was well tolerated throughout the trial: in Part 1 (SAD) Period 1, at doses of 100 mg, 200 mg, 400 mg, 700 mg, 1200 mg or 2000 mg under fasting conditions; in Part 1 (SAD) Period 2, at a dose of 400 mg under fed conditions; and in Part 2 (MAD) at doses of 100 mg (fasting), 100 mg (fed), 200 mg (fed), and 400 mg (fed).

Following administration of KAR5585 (prodrug), KAR5417 (active TPH1 inhibitor) appeared rapidly in plasma, an observation consistent with rapid absorption of KAR5585 and efficient conversion to KAR5417. A strong relationship was seen between KAR5417 exposure and 5-HIAA reductions.

Neither the prodrug (KAR5585) nor the active drug (KAR5417) showed any tendency to increase QTcF in a dose-dependent manner.

As described in the PK SAP, the following PK parameters (as appropriate) were to be generated from KAR5585 and KAR5417 individual plasma concentrations from Part 1, Day 1; and Part 2, Days 1, 7, and 14 within the PK Evaluable Population:

| | |
|---|---|
| $C_{max1}$ | Maximum concentration, obtained after first daily dose |
| $C_{max2}$ | Maximum concentration, obtained after second daily dose |
| $C_{12\ hr}$ | Concentration, obtained 12 hours after an administered dose |
| $C_{max1}/C_{12\ hr}$ | Ratio of maximum concentration, obtained after first daily dose to the concentration, obtained 12 hours after first administered daily dose |
| $C_{max1}/D$ | Dose-normalized $C_{max}$, obtained after first daily dose |
| $t_{max1}$ | Time to maximum concentration, obtained after first daily dose |
| $t_{max2}$ | Time to maximum concentration, obtained after second daily dose |
| $AUC_{0-tau}$ | Area under the concentration versus time curve from time 0 to the last quantifiable point within the dosing interval, using the trapezoidal rule |
| $AUC_{0-12}$ | Area under the concentration versus time curve from time 0 to 12 hours after dosing, using the trapezoidal rule |
| $AUC_{0-24}$ | Area under the concentration versus time curve from time 0 to 24 hours after dosing, using the trapezoidal rule |
| $AUC_{0-24}/D$ | Dose-normalized $AUC_{0-24}$ (Day for SAD, Day 1 and Day 7 for MAD) |
| $\lambda_z$ | Apparent terminal rate constant after oral administration |
| $t_{1/2}$ | Apparent terminal half-life after oral administration |
| $AUC_{0-inf}$ | Area under the concentration versus time curve from time 0 to infinity (SAD only) |
| AUC Extrap | Percent of $AUC_{0-\infty}$ extrapolated after the last quantifiable concentration |
| CL/F | Apparent oral clearance |
| $CL_{ss}/F$ | Apparent oral clearance at steady-state |
| $V_z/F$ | Apparent oral volume of distribution dependent during the terminal phase |

The doses administered were the following:
  In Part 1 (SAD) Period 1: single KAR5585 doses of 100 mg, 200 mg, 400 mg, 700 mg, 1200 mg, or 2000 mg or matching placebo in Cohorts 1 through 6, respectively.
  In Part 1 (SAD) Period 2: 400 mg in Cohort 3 only.
  In Part 2 (MAD): KAR5585 100 mg (fasting), 100 mg (fed), 200 mg (fed), and 400 mg (fed) or matching placebo administered BID (approximately every 12 hours) for 27 doses in Cohorts 1 through 4, respectively.

Doses were administered using the capsule strengths or sizes shown in Table 9.

TABLE 6

Doses and Capsule Strengths Administered

| | Part 1 (SAD) | | Part 2 (MAD) | |
|---|---|---|---|---|
| Cohort | Dose (mg) | Capsules Administered (KAR5585 or Placebo) | Dose (mg) | Capsules Administered (KAR5585 or Placebo) |
| 1 | 100 | Two 50 mg or matching | 100 | Two 50 mg or matching |

TABLE 6-continued

Doses and Capsule Strengths Administered

| Cohort | Part 1 (SAD) | | Part 2 (MAD) | |
|---|---|---|---|---|
| | Dose (mg) | Capsules Administered (KAR5585 or Placebo) | Dose (mg) | Capsules Administered (KAR5585 or Placebo) |
| | | placebo | | placebo |
| 2 | 200 | One 200 mg or matching placebo | 100 | Two 50 mg or matching placebo |
| 3 | 400 | Two 200 mg or matching placebo | 200 | One 200 mg or matching placebo |
| 4 | 700 | Two 200 mg + one 300 mg or matching placebo | 400 | Two 200 mg or matching placebo |
| 5 | 1200 | Four 300 mg or matching placebo | | |
| 6 | 2000 | Six 300 mg or matching placebo + one 200 mg or matching placebo | | |

Abbreviations:
MAD, multiple ascending dose;
SAD, single ascending dose

Figure 19A:
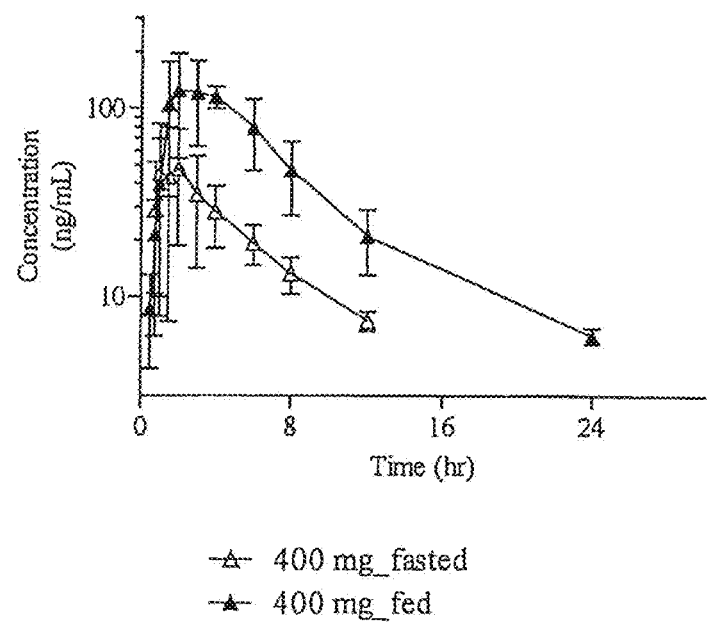
FIG. 19a is a plot of mean (±SD) plasma concentration-time profiles of KAR5585 following administration of 400 mg of KAR5585 under fed and fasting conditions—Cohorts 3A and 3B (log scale).
Figure 19B:
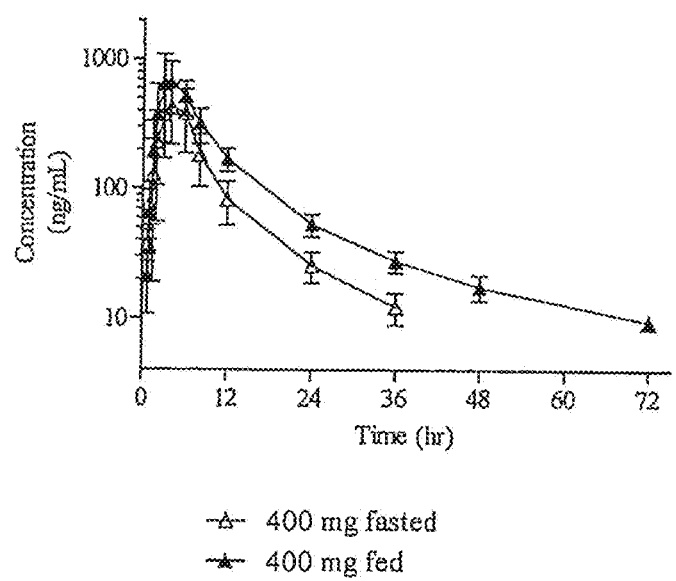
FIG. 19b is a plot of mean (±SD) plasma concentration-time profiles of KAR5417 following administration of 400 mg of KAR5585 under fed and fasting conditions—Cohorts 3A and 3B (log scale).
Figure 20:
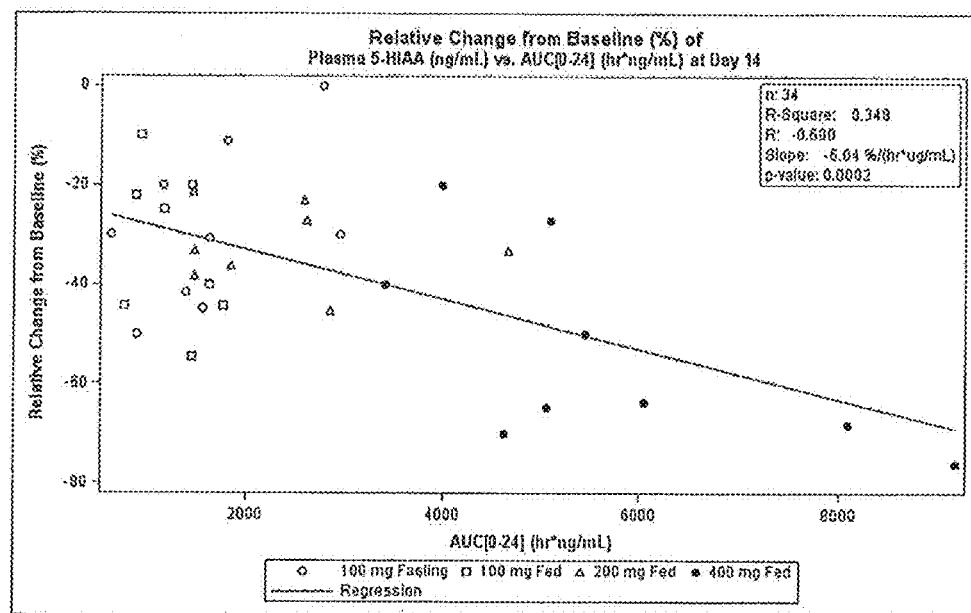
FIG. 20 is a plot of relative change from baseline percentage of plasma 5-HIAA vs $AUC_{0-24}$ at Day 14.

Pharmacokinetics Results and Tabulations of Individual Subject Data:
Plasma Concentrations:

The locations of individual and mean estimates of plasma KAR5585 and KAR5417 concentrations are tabulated below:

Mean plasma concentration-time profiles of KAR5585 and KAR5417 following administration of 100-2000 mg KAR5585 under fasting conditions in healthy adult subjects—Cohorts 1-6 (linear and semi-log scales) are presented in FIGS. 3a and 3b 5 and FIGS. 4a and 4b, respectively. Mean plasma concentration time profiles of KAR5585 and KAR5417 following administration of 400 mg of KAR5417 under fasting and fed conditions—Cohorts 3A and 3B (linear and semi-log scales) are presented in 18a and 18b and FIGS. 19a and 19b, respectively.

The mean peak plasma KAR5585 concentrations were reached between 1.5 and 3 hours following single-dose fasting oral administration of 100, 200, 400, 700, 1200 and 2000 mg KAR5585. For doses of 100 to 1200 mg KAR5585 the time to peak plasma concentrations of KAR5585 were reached between 0.75 and 6 hours. For the 2000 mg dose the time to peak plasma concentrations of KAR5585 ranged from 0.75 to 12 hours. Mean KAR5585 concentrations increased with increasing doses. KAR5585 concentrations remained above the LLOQ (4.94 ng/mL) up to 4 hours in most subjects following the 100 mg dose, in one subject KAR5585 was BLQ at all time-points and in another subject KAR5585 was measurable up to 8 hours. KAR5585 concentrations remained above the LLOQ (4.94 ng/mL) up to 12 hours following the 400, 700, 1200 and 200 mg doses of KAR5585.

The mean peak plasma KAR5417 concentrations were reached between 1.5 and 3 hours following single-dose fasting oral administration of 100, 200, 400, 700, 1200 and 2000 mg KAR5585. For doses of 100 to 1200 mg KAR5585 the time to peak plasma concentrations of KAR5417 were reached between 2 and 6 hours. For the 2000 mg dose of KAR5585 the time to peak plasma concentrations of KAR5417 ranged from 3 to 12 hours. Mean KAR5417 concentrations increased with increasing doses. KAR5417 concentrations remained above the LLOQ (7.65 ng/mL) up to 12, 24, 36, 48, 48 and 72 hours following the 100, 200, 400, 700, 1200 and 2000 mg doses, respectively. The plasma concentrations of KAR5417 were approximately 10-fold higher than the plasma concentrations of KAR5585.

Following administration of 400 mg KAR5585, peak mean plasma KAR5585 concentrations were observed at later times and sustained longer under fed relative to fasting conditions ($t_{max}$ was 3.0 and 2.07 hour postdose, for fed and fasted states, respectively). The peak mean concentrations were approximately 320% higher following drug administration under fed conditions ($C_{max}$=169 ng/mL) relative to fasting conditions ($C_{max}$=52.8 ng/mL). KAR5585 mean concentrations following drug administration under fed conditions were higher relative to fasting conditions and KAR5585 levels were measurable to 24 hours in the fed state, relative to 12 hours in the fasted state.

Following administration of 400 mg KAR5585, peak mean plasma KAR5417 concentrations were observed at similar times under fasting and fed conditions (4 hour postdose). The peak mean concentrations were approximately 177% higher following drug administration underfed conditions ($C_{max}$=860 ng/mL) relative to fasting conditions ($C_{max}$=485 ng/mL). KAR5417 mean concentrations following drug administration under fed conditions were higher relative to fasting conditions and KAR5585 levels were measurable to 72 hours in the fed state, relative to 36 hours in the fasted state.

TABLE 7

(Summary of the Mean Pharmacokinetic Parameters of KAR5585 Following a Single Oral Dose of KAR5585 (Cohorts 1-6) (Pharmacokinetic Evaluable Population))

| Dose (mg) | Stat. Param. | $t_1$ (hr) | $t_{max}{}^a$ (hr) | $C_{max}$ (ng/mL) | $C_{max}$/D [(ng/mL)/mg] | $C_{12}$ (ng/mL) | $C_{max}$/$C_{12}$ | AUC$_{0\text{-}tau}$ (hr*ng/mL) | AUC$_{0\text{-}12}$ (hr*ng/mL) |
|---|---|---|---|---|---|---|---|---|---|
| 100 (fasted) Cohort 1 | N | 3 | 8 | 8 | 8 | 0 | 0 | 8 | 3 |
| | Mean | 1.89 | 1.50 | 13.9 | 0.139 | BLQ | ND | 35.0 | 48.1 |
| | SD | 1.11 | 0.750, 6.00 | 5.35 | 0.0535 | NR | ND | 24.9 | 16.2 |
| | CV % | 58.5 | NA | 38.4 | 38.4 | NR | ND | 71.1 | 33.7 |
| | Geo. Mean | 1.71 | NA | 13.2 | 0.132 | BLQ | ND | 27.4 | 46.2 |
| | Geo. CV % | 58.2 | NA | 33.6 | 33.6 | NR | ND | 91.3 | 36.8 |
| 200 (fasted) Cohort 2 | N | 7 | 8 | 8 | 8 | 0 | 0 | 8 | 7 |
| | Mean | 3.63 | 1.78 | 19.2 | 0.0961 | BLQ | ND | 61.4 | 85.8 |
| | SD | 2.02 | 0.750, 3.00 | 7.84 | 0.0392 | NR | ND | 27.3 | 20.5 |
| | CV % | 55.7 | NA | 40.8 | 40.8 | NR | ND | 44.5 | 23.8 |
| | Geo. Mean | 3.17 | NA | 17.5 | 0.0875 | BLQ | ND | 52.0 | 83.3 |
| | Geo. CV % | 61.6 | NA | 53.0 | 53.0 | NR | ND | 85.5 | 28.0 |
| 400 | N | 7 | 9 | 9 | 9 | 7 | 7 | 9 | 8 |

TABLE 7-continued (Summary of the Mean Pharmacokinetic Parameters of KAR5585 Following a Single
Oral Dose of KAR5585 (Cohorts 1-6) (Pharmacokinetic Evaluable Population))

| | | | | | | | | | |
|---|---|---|---|---|---|---|---|---|---|
| (fasted) | Mean | 4.08 | 2.07 | 52.8 | 0.132 | 7.45 | 8.44 | 219 | 246 |
| Cohort 3A | SD | 0.635 | 1.00, 6.00 | 34.0 | 0.0851 | 0.879 | 4.64 | 112 | 86.6 |
| | CV % | 15.5 | NA | 64.4 | 64.4 | 11.8 | 55.0 | 51.0 | 35.3 |
| | Geo. Mean | 4.04 | NA | 42.0 | 0.105 | 7.40 | 7.20 | 176 | 231 |
| | Geo. CV % | 16.0 | NA | 88.1 | 88.1 | 12.0 | 72.0 | 103.0 | 40.4 |
| 400 | N | 9 | 9 | 9 | 9 | 9 | 9 | 9 | 9 |
| (fed) | Mean | 4.45 | 3.00 | 169 | 0.422 | 21.0 | 9.35 | 868 | 761 |
| Cohort 3B | SD | 1.27 | 1.50, 6.00 | 36.2 | 0.0904 | 7.97 | 4.39 | 152 | 86.7 |
| | CV % | 28.6 | NA | 21.4 | 21.4 | 38.0 | 47.0 | 17.5 | 11.4 |
| | Geo. Mean | 4.26 | NA | 165 | 0.413 | 19.7 | 8.36 | 854 | 756 |
| | Geo. CV % | 32.5 | NA | 22.6 | 22.6 | 38.4 | 55.7 | 19.6 | 12.3 |
| 700 | N | 8 | 8 | 8 | 8 | 6 | 6 | 8 | 8 |
| (fasted) | Mean | 3.46 | 1.75 | 99.4 | 0.142 | 10.7 | 12.2 | 386 | 392 |
| Cohort 4 | SD | 0.561 | 1.00, 3.00 | 29.3 | 0.0418 | 4.73 | 6.65 | 135 | 127 |
| | CV % | 16.2 | NA | 29.4 | 29.4 | 44.3 | 54.4 | 35.1 | 32.3 |
| | Geo. Mean | 3.42 | NA | 95.2 | 0.136 | 9.84 | 10.5 | 362 | 372 |
| | Geo. CV % | 16.8 | NA | 33.7 | 33.7 | 47.2 | 69.7 | 41.7 | 36.5 |
| 1200 | N | 8 | 9 | 9 | 9 | 7 | 7 | 9 | 8 |
| (fasted) | Mean | 3.58 | 2.00 | 83.0 | 0.0692 | 11.8 | 9.78 | 364 | 402 |
| Cohort 5 | SD | 1.35 | 1.00, 4.00 | 49.0 | 0.0408 | 4.33 | 5.27 | 189 | 164 |
| | CV % | 37.8 | NA | 59.0 | 59.0 | 36.8 | 53.9 | 51.9 | 40.7 |
| | Geo. Mean | 3.40 | NA | 68.1 | 0.0568 | 11.0 | 8.63 | 296 | 356 |
| | Geo. CV % | 33.9 | NA | 85.0 | 85.0 | 44.4 | 59.3 | 93.9 | 67.4 |
| 2000 | N | 8 | 9 | 9 | 9 | 8 | 8 | 9 | 9 |
| (fasted) | Mean | 4.84 | 2.00 | 104 | 0.0522 | 37.4 | 5.70 | 773 | 624 |
| Cohort 6 | SD | 1.05 | 0.750, 12.0 | 43.6 | 0.0218 | 36.7 | 3.98 | 418 | 239 |
| | CV % | 21.6 | NA | 41.8 | 41.8 | 98.1 | 69.9 | 54.0 | 38.3 |
| | Geo. Mean | 4.76 | NA | 95.1 | 0.0475 | 26.2 | 4.11 | 638 | 558 |
| | Geo. CV % | 20.2 | NA | 51.6 | 51.6 | 105 | 125 | 86.9 | 63.1 |

| | | Dose (mg) | Stat. Param. | $AUC_{0-24}$ (hr*ng/mL) | $AUC_{0-24}/D$ [(hr*ng/mL)/mg] | $AUC_{0-\infty}$ (hr*ng/mL) | $V_2/F$ (L) | CL/F (L/hr) |
|---|---|---|---|---|---|---|---|---|
| | | 100 | N | 3 | 3 | 3 | 3 | 3 |
| | | (fasted) | Mean | 49.6 | 0.496 | 49.5 | 5680 | 2210 |
| | | Cohort 1 | SD | 16.6 | 0.166 | 16.5 | 2830 | 849 |
| | | | CV % | 33.4 | 33.4 | 33.4 | 49.9 | 38.5 |
| | | | Geo. Mean | 47.5 | 0.475 | 47.5 | 5190 | 2110 |
| | | | Geo. CV % | 37.9 | 37.9 | 37.9 | 56.8 | 37.9 |
| | | 200 | N | 7 | 7 | 7 | 7 | 7 |
| | | (fasted) | Mean | 97.1 | 0.485 | 99.5 | 10300 | 2220 |
| | | Cohort 2 | SD | 25.9 | 0.130 | 28.0 | 4060 | 925 |
| | | | CV % | 26.7 | 26.7 | 28.1 | 39.5 | 41.6 |
| | | | Geo. Mean | 93.4 | 0.467 | 95.3 | 9610 | 2100 |
| | | | Geo. CV % | 33.1 | 33.1 | 35.4 | 40.5 | 35.4 |
| | | 400 | N | 7 | 7 | 7 | 7 | 7 |
| | | (fasted) | Mean | 297 | 0.742 | 302 | 8330 | 1480 |
| | | Cohort 3A | SD | 90.4 | 0.226 | 93.2 | 2240 | 606 |
| | | | CV % | 30.5 | 30.5 | 30.8 | 26.9 | 41.1 |
| | | | Geo. Mean | 283 | 0.707 | 288 | 8100 | 1390 |
| | | | Geo. CV % | 36.4 | 36.4 | 37.0 | 25.3 | 37.0 |
| | | 400 | N | 9 | 9 | 9 | 9 | 9 |
| | | (fed) | Mean | 885 | 2.21 | 915 | 2780 | 449 |
| | | Cohort 3B | SD | 128 | 0.321 | 148 | 549 | 85.2 |
| | | | CV % | 14.5 | 14.5 | 16.1 | 19.8 | 18.9 |
| | | | Geo. Mean | 876 | 2.19 | 903 | 2730 | 443 |
| | | | Geo. CV % | 15.8 | 15.8 | 17.7 | 21.2 | 17.7 |
| | | 700 | N | 8 | 8 | 8 | 8 | 8 |
| | | (fasted) | Mean | 432 | 0.617 | 436 | 9120 | 1810 |

TABLE 7-continued (Summary of the Mean Pharmacokinetic Parameters of KAR5585 Following a Single Oral Dose of KAR5585 (Cohorts 1-6) (Pharmacokinetic Evaluable Population))

|  |  |  |  |  |  |  |  |
|---|---|---|---|---|---|---|---|
| | Cohort 4 | SD | 148 | 0.211 | 150 | 4190 | 701 |
| | | CV % | 34.2 | 34.2 | 34.4 | 45.9 | 38.8 |
| | | Geo. Mean | 409 | 0.584 | 412 | 8390 | 1700 |
| | | Geo. CV % | 38.0 | 38.0 | 38.1 | 45.0 | 38.1 |
| 1200 (fasted) Cohort 5 | | N | 8 | 8 | 8 | 8 | 8 |
| | | Mean | 453 | 0.378 | 462 | 16900 | 3850 |
| | | SD | 182 | 0.152 | 186 | 12300 | 4080 |
| | | CV % | 40.2 | 40.2 | 40.2 | 72.7 | 106 |
| | | Geo. Mean | 400 | 0.333 | 406 | 14500 | 2960 |
| | | Geo. CV % | 70.9 | 70.9 | 73.0 | 58.7 | 73.0 |
| 2000 (fasted) Cohort 6 | | N | 9 | 9 | 8 | 8 | 8 |
| | | Mean | 806 | 0.403 | 778 | 25100 | 3820 |
| | | SD | 377 | 0.188 | 383 | 21900 | 3560 |
| | | CV % | 46.7 | 46.7 | 49.2 | 87.5 | 93.1 |
| | | Geo. Mean | 696 | 0.348 | 667 | 20600 | 3000 |
| | | Geo. CV % | 73.3 | 73.3 | 75.2 | 63.8 | 75.2 |

$^a$Median and range (Min, Max) presented;
Abbreviations:
$AUC_{0-12}$, area under the concentration versus time curve from time 0 to 12 hours after dosing, using the trapezoidal rule;
$AUC_{0-24}$, area under the concentration versus time curve from time 0 to 24 hours after dosing, using the trapezoidal rule;
$AUC_{0-tau}$, area under the concentration-time curve from time 0 to time of last quantifiable concentration;
BLQ, below the limit of quantitation;
CL/F, apparent oral clearance;
CV, coefficient of variation;
Geo., geometric;
hr, hour;
N, number;
NA, not applicable;
NR, not reported;
ND, not determined;
Param., parameter;
SD, standard deviation;
Stat., statistical;
$t_{1/2}$, apparent terminal half-life after oral administration;
$t_{max}$, time of maximum observed concentration;
$V_z/F$, volume of distribution during the terminal phase

TABLE 8

(Summary of the Mean Pharmacokinetic Parameters of KAR5417 Following a Single Oral Dose of KAR5585 (Cohorts 1-6) (Pharmacokinetic Evaluable Population))

| Dose (mg) | Stat. Param. | $t_{1/2}$ (hr) | $t_{max}^a$ (hr) | $C_{max}$ (ng/mL) | $C_{max}$/D (ng/mL)/mg | $C_{12}$ (ng/mL) | $C_{max}/C_{12}$ | $AUC_{0-tau}$ (hr*ng/ mL) | $AUC_{0-12}$ (hr*ng/ mL) | $AUC_{0-24}$ (hr*ng/ mL) | $AUC_{0-24}$/D (hr*ng/ mL)/mg | $AUC_{0-\infty}$ (hr*ng/ mL) |
|---|---|---|---|---|---|---|---|---|---|---|---|---|
| 100 (fasted) Cohort 1 | N | 8 | 9 | 9 | 9 | 8 | 8 | 9 | 8 | 8 | 8 | 8 |
| | Mean | 4.67 | 4.00 | 107 | 1.07 | 23.8 | 5.23 | 718 | 704 | 847 | 8.47 | 886 |
| | SD | 1.35 | 2.00, 6.00 | 44.2 | 0.442 | 8.61 | 1.64 | 358 | 172 | 251 | 2.51 | 293 |
| | CV % | 28.9 | NA | 41.5 | 41.5 | 36.1 | 31.3 | 49.8 | 24.5 | 29.6 | 29.6 | 33.1 |
| | Geo. Mean | 4.51 | NA | 93.1 | 0.931 | 22.5 | 5.04 | 605 | 686 | 816 | 8.16 | 847 |
| | Geo. CV % | 28.7 | NA | 72.6 | 72.6 | 36.6 | 28.7 | 83.2 | 24.2 | 29.1 | 29.1 | 32.6 |
| 200 (fasted) Cohort 2 | N | 9 | 9 | 9 | 9 | 9 | 9 | 9 | 9 | 9 | 9 | 9 |
| | Mean | 5.40 | 3.00 | 160 | 0.801 | 32.9 | 4.92 | 1120 | 947 | 1160 | 5.81 | 1230 |
| | SD | 1.08 | 2.00, 4.00 | 98.2 | 0.491 | 21.5 | 1.07 | 816 | 629 | 781 | 3.90 | 838 |
| | CV % | 20.0 | NA | 61.3 | 61.3 | 65.5 | 21.7 | 72.5 | 66.4 | 67.2 | 67.2 | 68.0 |
| | Geo. Mean | 5.29 | NA | 132 | 0.658 | 27.3 | 4.82 | 866 | 771 | 940 | 4.70 | 988 |
| | Geo. CV % | 21.6 | NA | 78.8 | 78.8 | 72.1 | 22.4 | 94.2 | 79.2 | 80.8 | 80.8 | 83.6 |
| 400 (fasted) Cohort 3A | N | 9 | 9 | 9 | 9 | 9 | 9 | 9 | 9 | 9 | 9 | 9 |
| | Mean | 11.3 | 4.00 | 485 | 1.21 | 82.5 | 6.04 | 3500 | 2690 | 3250 | 8.12 | 3650 |
| | SD | 9.24 | 3.00, 6.00 | 183 | 0.456 | 30.5 | 1.44 | 1440 | 1020 | 1210 | 3.02 | 1490 |
| | CV % | 81.6 | NA | 37.7 | 37.7 | 37.0 | 23.9 | 41.0 | 38.0 | 37.2 | 37.2 | 40.9 |
| | Geo. Mean | 9.29 | NA | 444 | 1.11 | 75.2 | 5.90 | 3120 | 2460 | 2970 | 7.43 | 3280 |

TABLE 8-continued (Summary of the Mean Pharmacokinetic Parameters of KAR5417 Following a Single
Oral Dose of KAR5585 (Cohorts 1-6) (Pharmacokinetic Evaluable Population))

| Dose (mg) | Stat. Param. | $t_{1/2}$ (hr) | $t_{max}^{a}$ (hr) | $C_{max}$ (ng/mL) | $C_{max}/D$ (ng/mL)/mg | $C_{12}$ (ng/mL) | $C_{max}/C_{12}$ | $AUC_{0-tau}$ (hr*ng/mL) | $AUC_{0-12}$ (hr*ng/mL) | $AUC_{0-24}$ (hr*ng/mL) | $AUC_{0-24}/D$ (hr*ng/mL)/mg | $AUC_{0-\infty}$ (hr*ng/mL) |
|---|---|---|---|---|---|---|---|---|---|---|---|---|
| | Geo. CV % | 67.8 | NA | 52.5 | 52.5 | 55.6 | 22.9 | 63.4 | 52.9 | 53.9 | 53.9 | 59.1 |
| 400 (fed) Cohort 3B | N | 9 | 9 | 9 | 9 | 9 | 9 | 9 | 9 | 9 | 9 | 9 |
| | Mean | 20.5 | 4.00 | 860 | 2.15 | 169 | 5.39 | 6440 | 4240 | 5430 | 13.6 | 6710 |
| | SD | 5.21 | 3.00, 6.00 | 224 | 0.561 | 34.7 | 2.06 | 1000 | 790 | 816 | 2.04 | 1070 |
| | CV % | 25.4 | NA | 26.1 | 26.1 | 20.6 | 38.2 | 15.6 | 18.6 | 15.0 | 15.0 | 15.9 |
| | Geo. Mean | 19.8 | NA | 831 | 2.08 | 165 | 5.03 | 6360 | 4170 | 5370 | 13.4 | 6630 |
| | Geo. CV % | 33.3 | NA | 28.8 | 28.8 | 20.8 | 42.2 | 17.3 | 20.2 | 16.2 | 16.2 | 17.9 |
| 700 (fasted) Cohort 4 | N | 9 | 9 | 9 | 9 | 9 | 9 | 9 | 9 | 9 | 9 | 9 |
| | Mean | 13.5 | 4.00 | 778 | 1.11 | 144 | 5.97 | 5840 | 4350 | 5310 | 7.58 | 6020 |
| | SD | 6.04 | 2.00, 6.00 | 537 | 0.767 | 126 | 1.53 | 4350 | 3010 | 3800 | 5.43 | 4410 |
| | CV % | 44.9 | NA | 69.0 | 69.0 | 87.4 | 25.5 | 74.4 | 69.3 | 71.5 | 71.5 | 73.2 |
| | Geo. Mean | 12.1 | NA | 544 | 0.777 | 93.8 | 5.80 | 3870 | 3050 | 3720 | 5.31 | 4170 |
| | Geo. CV % | 53.6 | NA | 157 | 157 | 153 | 26.6 | 180 | 153 | 149 | 149 | 150 |
| 1200 (fasted) Cohort 5 | N | 9 | 9 | 9 | 9 | 9 | 9 | 9 | 9 | 9 | 9 | 9 |
| | Mean | 14.9 | 6.00 | 896 | 0.747 | 213 | 4.53 | 7700 | 5350 | 6790 | 5.66 | 7970 |
| | SD | 5.60 | 3.00, 6.00 | 453 | 0.377 | 130 | 1.40 | 4000 | 2710 | 3480 | 2.90 | 4040 |
| | CV % | 37.5 | NA | 50.5 | 50.5 | 60.9 | 30.9 | 52.0 | 50.6 | 51.2 | 51.2 | 50.7 |
| | Geo. Mean | 14.0 | NA | 764 | 0.636 | 175 | 4.36 | 6580 | 4580 | 5810 | 4.84 | 6880 |
| | Geo. CV % | 41.5 | NA | 75.0 | 75.0 | 81.0 | 29.0 | 73.0 | 73.3 | 72.8 | 72.8 | 69.5 |
| 2000 (fasted) Cohort 6 | N | 9 | 9 | 9 | 9 | 9 | 9 | 9 | 9 | 9 | 9 | 9 |
| | Mean | 22.6 | 5.00 | 1080 | 0.542 | 354 | 4.23 | 10600 | 6910 | 9080 | 4.54 | 10900 |
| | SD | 5.07 | 3.00, 12.0 | 345 | 0.173 | 271 | 1.94 | 3510 | 2110 | 3000 | 1.50 | 3570 |
| | CV % | 22.4 | NA | 31.9 | 31.9 | 76.6 | 45.8 | 33.3 | 30.6 | 33.0 | 33.0 | 32.9 |
| | Geo. Mean | 22.1 | NA | 1030 | 0.515 | 280 | 3.67 | 9880 | 6550 | 8520 | 4.26 | 10200 |
| | Geo. CV % | 22.4 | NA | 37.2 | 37.2 | 83.8 | 70.2 | 43.9 | 38.3 | 42.6 | 42.6 | 43.0 |

$^{a}$Median and range (Min, Max) presented; $V_z/F$ and CL/F were not calculated for KAR5417 as this is a metabolite of KAR5585

Abbreviations:
$AUC_{0-12}$, area under the concentration versus time curve from time 0 to 12 hours after dosing, using the trapezoidal rule;
$AUC_{0-24}$, area under the concentration versus time curve from time 0 to 24 hours after dosing, using the trapezoidal rule;
$AUC_{0-tau}$, area under the concentration-time curve from time 0 to time of last quantifiable concentration;
BLQ, below the limit of quantitation;
CL/F, apparent oral clearance;
CV, coefficient of variation;
Geo., geometric;
hr, hour;
Max, maximum;
Min, minimum;
N, number;
NA, not applicable;
NR, not reported;
ND, not determined;
Param., parameter;
SD, standard deviation;
Stat., statistical;
$t_{1/2}$, apparent terminal half-life after oral administration;
$t_{max}$, time of maximum observed concentration;
$V_z/F$, volume of distribution during the terminal phase.

Pharmacokinetics of KAR5417:

KAR5417 is the active metabolite of the prodrug, KAR5585. Following administration of KAR5585, KAR5417 appeared rapidly in plasma, an observation consistent with rapid absorption of KAR5585 and efficient conversion to KAR5417; all subjects had measurable concentrations of KAR5417 by 0.25 hours postdose, and the median $t_{max}$ was comparable across all fasting Cohorts and ranged between 3 and 6 hours postdose.

In general, mean peak plasma KAR5417 concentrations, as measured by mean $C_{max}$, appeared to increase in a dose-proportional manner from 100-700 mg, mean $C_{max}$ values increased 7.27-fold over the 7-fold increase in dose between the 100 mg dose (Cohort 1) and the 700 mg dose (Cohort 4). At doses greater than 700 mg, there was a moderate increase in $C_{max}$ values, with a 1.38-fold increase over the 2.86-fold increase in dose between 700 mg (Cohort 4) and 2000 mg (Cohort 6).

Overall, the mean extent of systemic exposure to KAR5417, as measured by mean $AUC_{0-24}$ and $AUC_{0-inf}$, appeared to increase in a dose-proportional manner between the 100 and 700 mg dose levels, with a 6.3-fold and 6.8-fold increase in mean $AUC_{0-24}$ and mean $AUC_{0-inf}$ estimates, respectively, for a 7-fold increase in dose between the 100 mg dose (Cohort 1) and the 700 mg dose (Cohort 4). At dose levels greater than 700 mg, there was a less than dose-proportional increase in $AUC_{0-24}$ and $AUC_{0-inf}$ values, with a 1.7-fold and 1.81-fold increase over the 2.86-fold increase in dose between 700 mg (Cohort 4) and 2000 mg (Cohort 6).

Administration of the KAR5585 under fed conditions increased the extent and peak of exposure of KAR5417 with mean AUCs ($AUC_{0-inf}$) increasing 1.8-fold from 3650 ng·hr/mL to 6710 ng·hr/mL and $C_{max}$ increasing 1.8-fold from 485 ng/mL to 860 ng/mL, under fasting and fed conditions, respectively. This was considered to be a clinically relevant change in exposure.

The mean apparent elimination half-life of KAR5417 increased with increasing dose levels studied, and ranged between 4.67 (100 mg dose) and 22.6 hours (2000 mg dose) after oral administration of KAR5585. The elimination phase of KAR5417 was characterized based on the last 3 to 6 measurable time points.

Dose Proportionality Assessment of KAR5585 and KAR5417

Scatter plots of individual plasma KAR5585 and KAR5417 $C_{max}$ and $AUC_{0-inf}$ versus KAR5585 dose are presented in FIGS. 5a and 5b and FIGS. 6a and 6b, respectively.

The dose proportionality assessment of plasma KAR5585 and KAR5417 PK parameters are summarized in Table 18. Dose proportionality was assessed for KAR5585 and KAR5417 after single-dose administration using the power model. From plots of exposure (e.g., $C_{max}$, $AUC_{0-12}$, $AUC_{0-tau}$, and/or $AUC_{0-inf}$) versus dose, increases in exposure were deemed dose proportional if the 90% confidence intervals (CIs) for the slope (β in the following equation(s) included unity (e.g., 1.0).

The 95% CI for the slope of from the power model for $AUC_{0-inf}$ and $C_{max}$ for KAR5417 included the value of 1. Therefore, dose proportionality was concluded for $AUC_{0-inf}$ and $C_{max}$ for KAR5417 in the studied dose range of 100 to 2000 mg KAR5585. Therefore, for KAR5417 $AUC_{0-inf}$ and $C_{max}$ PK parameters, conditions of statistical linearity were met.

The 95% CI for the slope of from the power model for $AUC_{0-inf}$ and $C_{max}$ for KAR5585 did not include the value of 1. Therefore, dose proportionality was not concluded for $AUC_{0-inf}$ and $C_{max}$ for KAR5585 in the studied dose range of 100 to 2000 mg KAR5585. Therefore, for KAR5585 $AUC_{0-inf}$ and $C_{max}$ PK parameters, conditions of statistical linearity were not met and exposure as assessed by $AUC_{0-inf}$ and $C_{max}$ appeared to increase in a less than dose proportional manner.

Food Effect Assessment of KAR5585 and KAR5417:

The statistical results for the food effect assessment following administration of 400 mg KAR5585 under fasting and fed conditions—Cohorts 3A and 3B is presented in Table 10.

TABLE 10

(Summary of Statistical Comparison of Plasma KAR5585 and KAR5417 Pharmacokinetic Parameters $AUC_{0-tau}$, $AUC_{0-inf}$, $C_{max}$: Food Effect Assessment [Cohort 3B (Fed) Versus Cohort 3A (Fasting)] (Pharmacokinetic Evaluable Population))

| Parameter | Geometric Mean | | Geometric LS Mean Ratio | 90% CI |
|---|---|---|---|---|
| | Cohort 3B (Fed) | Cohort 3A (Fasting) | | |
| KAR5585 | | | | |

TABLE 9

(Summary of Dose Proportionality Analysis of Plasma KAR5417 and KAR5585 Pharmacokinetic Parameters $AUC_{0-12}$, $AUC_{0-inf}$, $AUC_{0-tau}$, and $C_{max}$ Following 100 to 2000 mg of KAR5585 Administered as a Single Oral Dose under Fasting Conditions (Pharmacokinetic Evaluable Population))

| Pharmacokinetic Parameter | Analyte | Effect | Estimate | Degrees of Freedom | Standard Error | 95% Confidence Interval |
|---|---|---|---|---|---|---|
| $AUC_{0-12}$ | KAR5417 | Intercept | 14.5 | 51 | NC | NC |
| | | Slope (β) | 0.812 | 51 | 0.0898 | 0.632-0.992 |
| | KAR5585 | Intercept | 1.51 | 41 | NC | NC |
| | | Slope (β) | 0.794 | 41 | 0.0822 | 0.629-0.960 |
| $AUC_{0-inf}$ | KAR5417 | Intercept | 12.3 | 51 | NC | NC |
| | | Slope (β) | 0.891 | 51 | 0.0915 | 0.707-1.07 |
| | KAR5585 | Intercept | 1.46 | 39 | NC | NC |
| | | Slope (β) | 0.822 | 39 | 0.0908 | 0.638-1.01 |
| $AUC_{0-tau}$ | KAR5417 | Intercept | 6.54 | 52 | NC | NC |
| | | Slope (β) | 0.975 | 52 | 0.101 | 0.772-1.18 |
| | KAR5585 | Intercept | 0.258 | 49 | NC | NC |
| | | Slope (β) | 1.04 | 49 | 0.105 | 0.829-1.25 |
| $C_{max}$ | KAR5417 | Intercept | 1.95 | 52 | NC | NC |
| | | Slope (β) | 0.845 | 52 | 0.0938 | 0.657-1.03 |
| | KAR5585 | Intercept | 0.534 | 49 | NC | NC |
| | | Slope (β) | 0.707 | 49 | 0.0827 | 0.541-0.873 |

Dose proportionality was not rejected if the 95% CI for the slope included the value of 1.

Abbreviations:

$AUC_{0-12}$, area under the concentration versus time curve from time 0 to 12 hours after dosing, using the trapezoidal rule;
$AUC_{0-inf}$, area under the concentration versus time curve from time 0 extrapolated to infinity;
$AUC_{0-tau}$, area under the concentration-time curve from time 0 to time of last quantifiable concentration;
$C_{max}$, maximum observed concentration;
CI, confidence interval
NC, not calculated.

TABLE 10-continued (Summary of Statistical Comparison of Plasma KAR5585 and
KAR5417 Pharmacokinetic Parameters $AUC_{0-tau}$, $AUC_{0-inf}$, $C_{max}$:
Food Effect Assessment [Cohort 3B (Fed) Versus Cohort
3A (Fasting)] (Pharmacokinetic Evaluable Population))

| | Geometric Mean | | | |
|---|---|---|---|---|
| Parameter | Cohort 3B (Fed) | Cohort 3A (Fasting) | Geometric LS Mean Ratio | 90% CI |
| $C_{max}$ | 165 | 42.0 | 3.92 | 2.51-6.13 |
| $AUC_{0-tau}$ | 854 | 176 | 4.84 | 3.10-7.56 |
| $AUC_{0-inf}$ | 903 | 288 | 3.14 | 2.42-4.07 |
| | | KAR5417 | | |
| $C_{max}$ | 831 | 444 | 1.87 | 1.47-2.38 |
| $AUC_{0-tau}$ | 6360 | 3120 | 2.04 | 1.54-2.69 |
| $AUC_{0-inf}$ | 6630 | 3280 | 2.02 | 1.56-2.61 |

Parameters were ln-transformed prior to analysis.
Geometric LS means are calculated by exponentiating the LS means from the ANOVA.
Geometric Mean Ratio = (test/reference)
Cohort 3A (Fasting): 400 mg KAR5585 Administered as a Single Oral Dose Under Fasting Conditions (reference)
Cohort 4B (Fed): 400 mg KAR5585 Administered as a Single Oral Dose Under Fed Conditions (test)
Abbreviations:
ANOVA, analysis of variance;
$AUC_{0-inf}$, area under the concentration versus time curve from time 0 extrapolated to infinity;
$AUC_{0-tau}$, area under the concentration-time curve from time 0 to time of last quantifiable concentration;
CI, confidence interval;
$C_{max}$, maximum observed concentration;
LS means, least-squares means.

The exposure as assessed by $AUC_{0-tau}$ and $AUC_{0-inf}$ to KAR5585 following administration of 400 mg KAR5585 under fed conditions was approximately 3.1-4.8-fold relative to when the KAR5585 was administered under fasting conditions. Peak exposure ($C_{max}$) was approximately 3.9-fold higher. The exposure as assessed by $AUC_{0-tau}$ and $AUC_{0-inf}$ to KAR5417 following administration of the 400 mg KAR5585 under fed conditions was approximately 2-fold higher relative to when the KAR5585 was administered under fasting conditions. Peak exposure was approximately 1.87-fold higher. The 90% CI for $C_{max}$, $AUC_{0-tau}$, and $AUC_{0-inf}$ were outside the commonly accepted range of 80-125% suggesting that there was a food effect for $AUC_{0-tau}$ and $AUC_{0-inf}$ and $C_{max}$ for KAR585 and KAR5417. The increase in systemic exposure was considered to be a clinically relevant effect on the oral absorption pharmacokinetics of KAR5585 and KAR5417.

Figure 7:
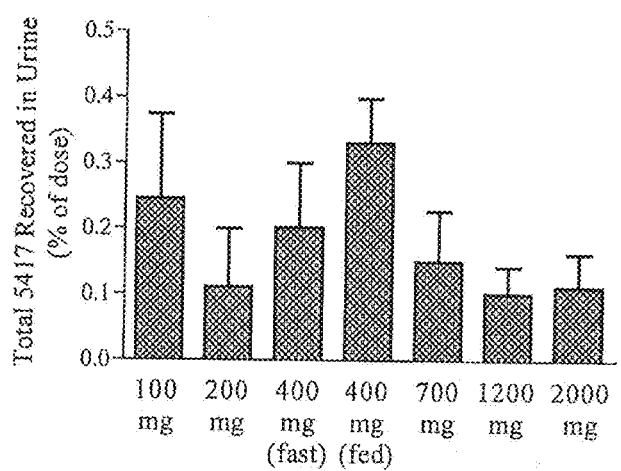
FIG. 7 is a bar graph of mean (±SD) total percent of dose excreted in urine as KAR5417 in fasted healthy volunteers following a single oral dose of KAR5585.
Figure 8:
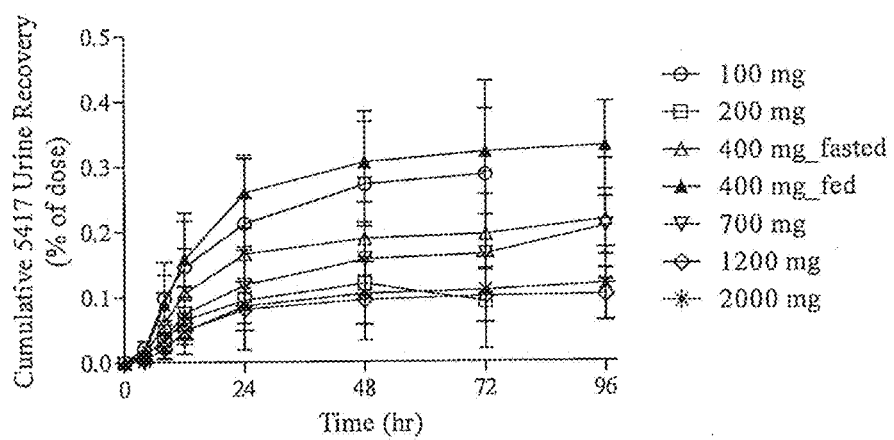
FIG. 8 is a plot of cumulative mean (±SD) urine recoveries vs. sampling time of KAR5417 in fasted healthy volunteers following a single oral dose of KAR5585.

Urine Concentrations:

The locations of individual and mean estimates of urine KAR5585 and KAR5417 concentrations and cumulative excretion tabulated below:

Mean total percent of dose excreted in urine as KAR5417 and mean cumulative urine recoveries in fasted healthy volunteers following administration of 100-2000 mg KAR5585 under fasting conditions in healthy adult subjects—Cohorts 1-6 are presented in FIGS. 7 and 8.

Mean urine PK parameters for KAR5585 and KAR5417 in healthy volunteers following a single oral dose of KAR5585—Cohorts 1-6 are presented in Table 12 and Table 13, respectively.

In almost all subjects, KAR5585 could not be quantified in urine samples and the amount excreted (Ae) in urine was less than 0.004% of the administered dose at all dose levels (Table 20).

KAR5417 could be quantified in urine samples and the amount excreted (Ae) in urine ranged from 0.102 to 0.331% of the administered dose (Table 13), assuming complete conversion of KAR5585 to KAR5417. The highest amount of KAR5417 excreted, 0.331% of the dose.

FIG. 7 was in the 400 mg fed Cohort (Cohort 3B) and was consistent with the effect of food to increase oral absorption of KAR5585. In general, the amount of KAR5417 excreted in urine was independent of dose in fasted subjects. The majority of urinary excretion of KAR5417 occurred in the first 24 hours after an oral dose of KAR5585.

Renal clearance of KAR5417 was calculated from the area under the plasma time concentration curve ($AUC_{0-96}$) for KAR5417 and the amount of KAR5417 recovered in urine (Table 21). Renal clearance of KAR5417 ranged from 157 to 296 mL/hr and was largely independent of administered dose of KAR5585 (Table 21).

The measurement of KAR5585 and KAR5417 in human urine indicates that renal clearance and elimination of KAR5585 and KAR5417 was a very minor route of elimination of KAR5585 following single dose administration in humans.

TABLE 11

(Mean (±SD) Urine PK Parameters for KAR5585 in
Healthy Volunteers Following a Single Oral Dose
of KAR5585 (Pharmacokinetic Evaluable Population))

| Dose (mg) | Stat. Param. | Amount Excreted($A_e$) (μg) | Total Excreted (%) | Plasma $AUC_{0-96}$ (ng · hr/mL) | $CL_R$ (mL/hr) |
|---|---|---|---|---|---|
| 100 | N | 9 | 9 | 3 | 3 |
| | Mean | 0 | 0 | 49.7 | 0 |
| | SD | 0 | 0 | 16.6 | 0 |
| | CV % | 0 | 0 | 33.4 | 0 |
| 200 | N | 9 | 9 | 7 | 7 |
| | Mean | 0 | 0 | 100 | 0 |
| | SD | 0 | 0 | 27.7 | 0 |
| | CV % | 0 | 0 | 27.7 | 0 |
| 400 | N | 9 | 9 | 7 | 7 |
| (Fasted) | Mean | 13.8 | 0.00346 | 303 | 51.5 |
| | SD | 24.6 | 0.00616 | 93.2 | 88.9 |
| | CV % | 178 | 178 | 30.8 | 173 |
| 400 | N | 9 | 9 | 9 | 9 |
| (Fed) | Mean | 0 | 0 | 917 | 0 |
| | SD | 0 | 0 | 147 | 0 |
| | CV % | 0 | 0 | 16.0 | 0 |
| 700 | N | 9 | 9 | 8 | 9 |
| | Mean | 0 | 0 | 436 | 0 |
| | SD | 0 | 0 | 150 | 0 |
| | CV % | 0 | 0 | 34.4 | 0 |
| 1200 | N | 9 | 9 | 8 | 9 |
| | Mean | 0 | 0 | 463 | 0 |
| | SD | 0 | 0 | 186 | 0 |
| | CV % | 0 | 0 | 40.1 | 0 |
| 2000 | N | 9 | 9 | 8 | 8 |
| | Mean | 1.50 | 0.0000751 | 779 | 2.30 |
| | SD | 4.51 | 0.000225 | 384 | 6.50 |
| | CV % | 300 | 300 | 49.3 | 283 |

Abbreviations:
CV, coefficient of variation;
N, number;
Param., parameter;
SD, standard deviation;
Stat., statistical D, standard deviation.

TABLE 12

Mean (±SD) Urine PK Parameters for KAR5417
in Healthy Volunteers Following a Single Oral Dose
of KAR5585 (Pharmacokinetic Evaluable Population)

| Dose (mg) | Stat. Param. | Amount Excreted($A_e$) (μg) | Total Excreted (%) | Plasma $AUC_{0-96}$ (ng · hr/mL) | $CL_R$ (mL/hr) |
|---|---|---|---|---|---|
| 100 | N | 9 | 9 | 8 | 8 |

TABLE 12-continued

Mean (±SD) Urine PK Parameters for KAR5417 in Healthy Volunteers Following a Single Oral Dose of KAR5585 (Pharmacokinetic Evaluable Population)

| Dose (mg) | Stat. Param. | Amount Excreted($A_e$) (µg) | Total Excreted (%) | Plasma $AUC_{0-96}$ (ng · hr/mL) | $CL_R$ (mL/hr) |
|---|---|---|---|---|---|
|  | Mean | 233 | 0.245 | 889 | 296 |
|  | SD | 123 | 0.129 | 293 | 86.1 |
|  | CV % | 52.7 | 52.7 | 33.0 | 29.1 |
| 200 | N | 9 | 9 | 9 | 9 |
|  | Mean | 211 | 0.111 | 1240 | 160 |
|  | SD | 169 | 0.0885 | 838 | 66.8 |
|  | CV % | 80.0 | 80.0 | 67.8 | 41.8 |
| 400 (fasted) | N | 9 | 9 | 9 | 9 |
|  | Mean | 769 | 0.202 | 3630 | 217 |
|  | SD | 376 | 0.0986 | 1450 | 57.2 |
|  | CV % | 48.8 | 48.8 | 39.9 | 26.4 |
| 400 (fed) | N | 9 | 9 | 9 | 9 |
|  | Mean | 1260 | 0.331 | 6590 | 191 |
|  | SD | 259 | 0.0679 | 1020 | 28.9 |
|  | CV % | 20.5 | 20.5 | 15.4 | 15.1 |
| 700 | N | 9 | 9 | 9 | 9 |
|  | Mean | 998 | 0.150 | 5990 | 191 |
|  | SD | 515 | 0.0773 | 4360 | 50.8 |
|  | CV % | 51.6 | 51.6 | 72.8 | 26.5 |
| 1200 | N | 9 | 9 | 9 | 9 |
|  | Mean | 1170 | 0.102 | 7910 | 157 |
|  | SD | 463 | 0.0405 | 4010 | 32.8 |
|  | CV % | 39.6 | 39.6 | 50.6 | 20.9 |
| 2000 | N | 9 | 9 | 9 | 9 |
|  | Mean | 2130 | 0.112 | 10700 | 206 |
|  | SD | 967 | 0.0508 | 3480 | 67.9 |
|  | CV % | 45.5 | 45.5 | 32.6 | 32.9 |

Abbreviations:
CV, coefficient of variation;
N, number;
PK, pharmacokinetic;
Param., parameter;
SD, standard deviation;
Stat., statistical.

Discussion of Pharmacokinetics Results

KAR5585 is a prodrug for the active TPH1 inhibitor KAR5417. Following KAR5585 administration, KAR5585 was rapidly absorbed the median $t_{max}$ ranged between 1.5 and 3 hours postdose. Following administration of KAR5585, KAR5417 appeared rapidly in plasma, an observation consistent with rapid absorption of KAR5585 and efficient conversion to KAR5417; the median $t_{max}$ was comparable across all fasting Cohorts and ranged between 3 and 6 hours postdose. Following single oral doses of 100 mg to 2000 mg KAR5588 in healthy subjects, the total extent of exposures ($AUC_{0-tau}$ and $AUC_{0-inf}$) and peak of exposure to KAR5855 and KAR5417 appeared to increase in a proportional manner from 100-700 mg, and in a less than dose proportional manner from 700 mg to 2000 mg.

The mean extent of systemic exposure to the prodrug, KAR5585, as measured by mean $AUC_{0-tau}$ and $AUC_{0-inf}$ appeared to increase in a dose proportional manner between the 100 and 700 mg dose levels, with a 8.7-fold and 8.8-fold increase in mean $AUC_{0-24}$ and mean $AUC_{0-inf}$ estimates, respectively, for a 7-fold increase in dose between the 100 mg dose (Cohort 1) and the 700 mg dose (Cohort 4). At dose greater than 700 mg, there was a less than dose-proportional increase in $AUC_{0-24}$ and $AUC_{0-inf}$ values, with a 1.86-fold and 1.78-fold increase over the 2.86-fold increase in dose between 700 mg (Cohort 4) and 2000 mg (Cohort 6).

The mean extent of systemic exposure to the active TPH1 inhibitor, KAR5417, as measured by mean $AUC_{0-24}$ and $AUC_{0-inf}$ appeared to increase in a dose proportional manner between the 100 and 700 mg dose levels, with a 6.3-fold and 6.8-fold increase in mean $AUC_{0-24}$ and mean $AUC_{0-inf}$ estimates, respectively, for a 7-fold increase in dose between the 100 mg dose (Cohort 1) and the 700 mg dose (Cohort 4). At dose greater than 700 mg, there was a less than dose-proportional increase in $AUC_{0-24}$ and $AUC_{0-inf}$ values, with a 1.7-fold and 1.81-fold increase over the 2.86-fold increase in dose between 700 mg (Cohort 4) and 2000 mg (Cohort 6).

The mean apparent elimination half-life of KAR5585 increased with increasing dose levels studied, and ranged between 1.89 and 4.84 hours after oral administration of KAR5585. The mean apparent elimination half-life of KAR5417 increased with increasing dose levels studied, and ranged between 4.67 (100 mg dose) and 22.6 hours (2000 mg dose) after oral administration of KAR5585.

Mean CL/F estimates of KAR5585 ranged from 1480 to 3850 L/h with the higher CL/F values noted for the 1200 mg (Cohort 5) and 2000 mg (Cohort 6) dose levels and is associated with non-linear PK related to decreased absorption of KAR5585 at the higher dose levels. The $V_z/F$ increased with increasing dose levels and ranged between 5680 to 25100 L, the higher $V_z/F$ values noted for the 1200 mg (Cohort 5) and 2000 mg (Cohort 6) dose levels was attributed to decreased absorption of KAR5585 at the higher dose levels.

Administration of the KAR5585 under fed conditions increased the extent and peak exposure of KAR5585 with mean AUCs ($AUC_{0-inf}$) increasing 3-fold from 302 ng·hr/mL to 915 ng·hr/mL and $C_{max}$ increasing 3.2-fold from 52.8 ng/mL to 169 ng/mL, under fasting and fed conditions, respectively. In a similar manner, fed conditions increased the extent and peak of exposure of KAR5417 with mean AUCs ($AUC_{0-inf}$) increasing 1.8-fold from 3650 ng·hr/mL to 6710 ng·hr/mL and $C_{max}$ increasing 1.8-fold from 485 ng/mL to 860 ng/mL, under fasting and fed conditions, respectively. This was considered to be a clinically relevant change in exposure.

Urinary excretion of KAR5585 and KAR5417 was a minor mechanism of elimination. KAR5585 was not quantifiable in urine in almost all subjects. KAR5417 could be quantified in urine samples and the amount excreted (Ae) in urine ranged from 0.102 to 0.331% of the administered dose of KAR5585.

Pharmacokinetics Conclusions

KAR5585 is a prodrug for the active TPH1 inhibitor KAR5417. Following KAR5585 administration, KAR5585 was rapidly absorbed the median $t_{max}$ ranged between 1.5 and 3 hours postdose. Following administration of KAR5585, KAR5417 appeared rapidly in plasma, an observation consistent with rapid absorption of KAR5585 and efficient conversion to KAR5417.

The mean extent of systemic exposure to the active TPH1 inhibitor, KAR5417, as measured by mean $AUC_{0-24}$ and $AUC_{0-inf}$ appeared to increase in a dose proportional manner between the 100 and 700 mg dose levels, with a 6.3-fold and 6.8-fold increase in mean $AUC_{0-24}$ and mean $AUC_{0-inf}$ estimates, respectively, for a 7-fold increase in dose between the 100 mg dose and the 700 mg dose. At dose greater than 700 mg, there was a slightly less than dose-proportional increase in $AUC_{0-24}$ and $AUC_{0-inf}$ values, with a 1.7-fold and 1.81-fold increase over the 2.86-fold increase in dose between 700 mg and 2000 mg. The mean apparent elimination half-life of KAR5417 increased with increasing dose levels studied, and ranged between 4.7 hours (100 mg dose) and 22.6 hours (2000 mg dose) after oral administration of KAR5585.

Administration of the KAR5585 under fed conditions, increased the extent and peak of exposure of both KAR5585 and KAR5417, with KAR5417 mean AUCs ($AUC_{0\text{-}inf}$) increasing 1.8-fold from 3650 ng·hr/mL to 6710 ng·hr/mL and $C_{max}$ increasing 1.8-fold from 485 ng/mL to 860 ng/mL, under fasting and fed conditions, respectively. This was considered to be a clinically relevant change in exposure.

Part 2: Multiple Ascending Dose

Figure 9A:
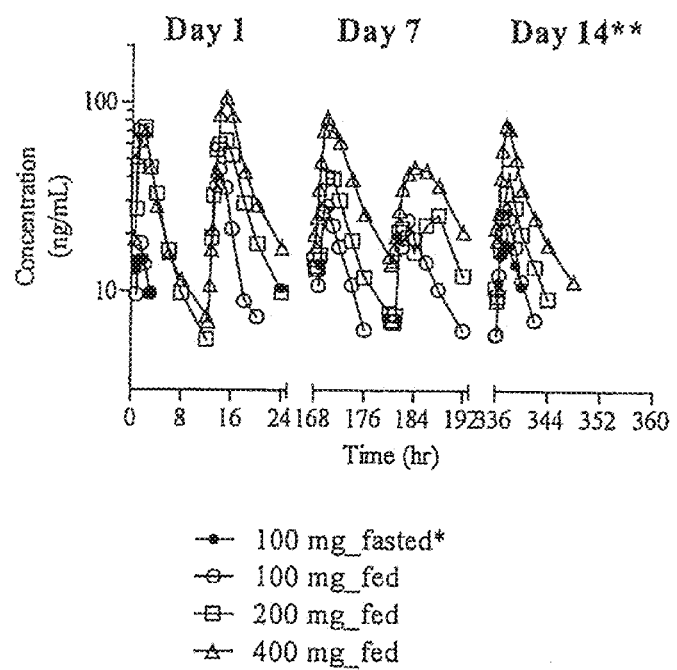
FIG. 9a is a plot of mean concentration vs. time profiles of KAR5585 in fasted and fed healthy volunteers following BID oral administration of KAR5585 for 14 days (semi-log scale)
Figure 9B:
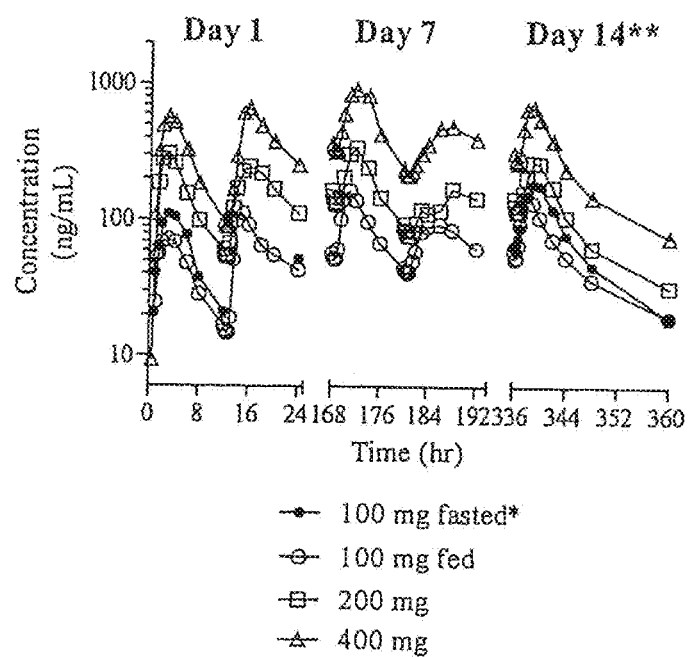
FIG. 9b is a plot of mean concentration vs. time profiles of KAR5417 in fasted and fed healthy volunteers following BID oral administration of KAR5585 for 14 days (semi-log scale)
Figure 10:
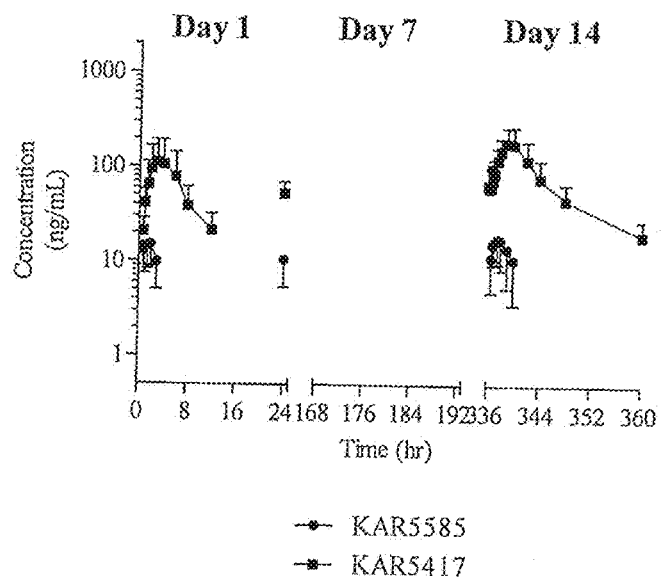
FIG. 10 is a plot of mean (±SD) concentration vs. time profiles of KAR5585 and KAR5417 in fasted healthy volunteers following BID oral administration of 100 mg KAR5585 for 14 days.
Figure 11:
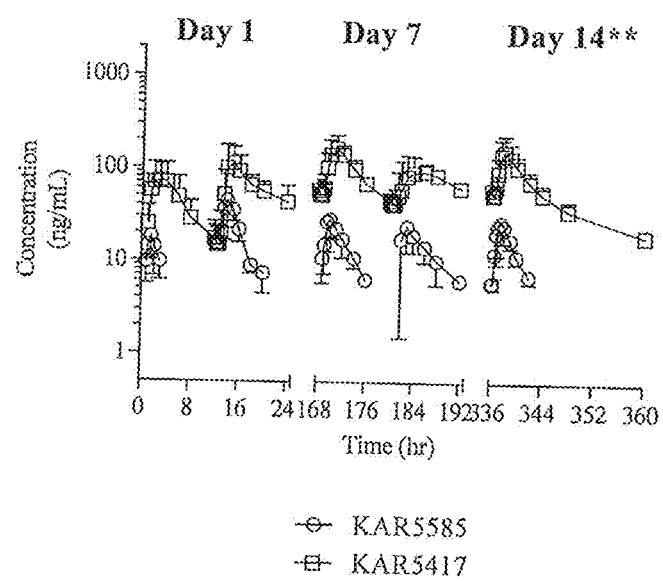
FIG. 11 is a plot of mean (±SD) concentration vs. time profiles of KAR5585 and KAR5417 in fed healthy volunteers following BID oral administration of 100 mg KAR5585 for 14 days.
Figure 12:
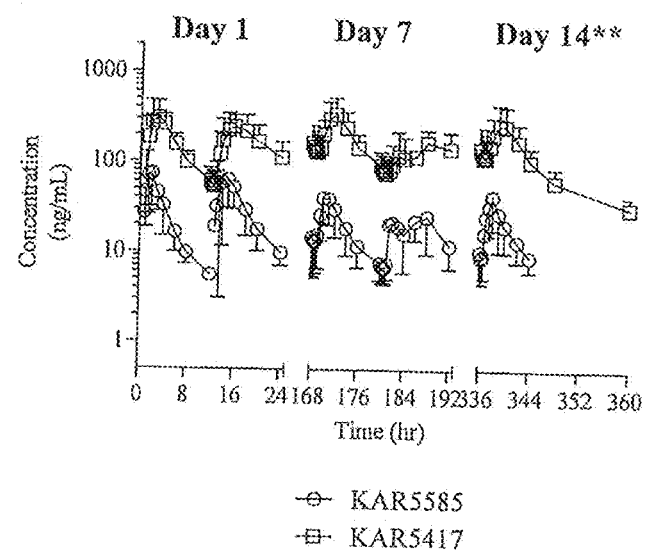
FIG. 12 is a plot of mean (±SD) concentration vs. time profiles of KAR5585 and KAR5417 in fed healthy volunteers following BID oral administration of 200 mg KAR5585 for 14 days.
Figure 13:
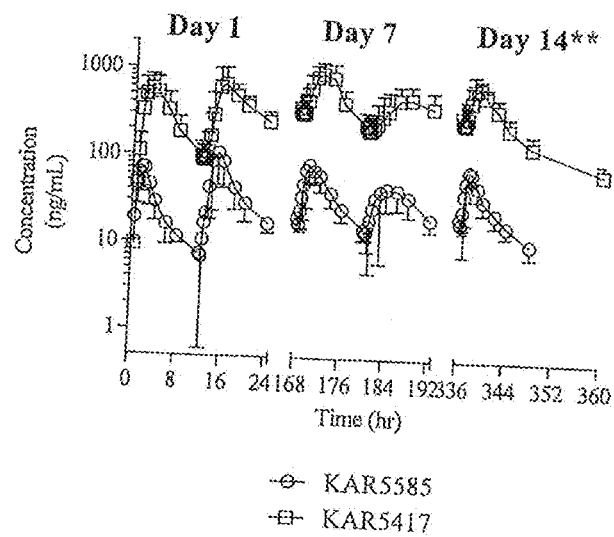
FIG. 13 is a plot of mean (±SD) concentration vs. time profiles of KAR5585 and KAR5417 in fed healthy volunteers following BID oral administration of 400 mg KAR5585 for 14 days.
Figure 14A:
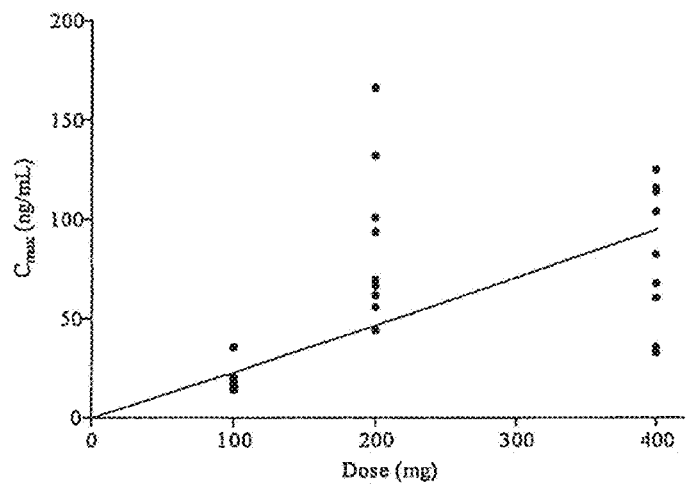
FIG. 14a is a plot of dose vs. $C_{max}$ for KAR5585 in fed healthy volunteers following BID oral administration of KAR5585 for 14 days.
Figure 14B:
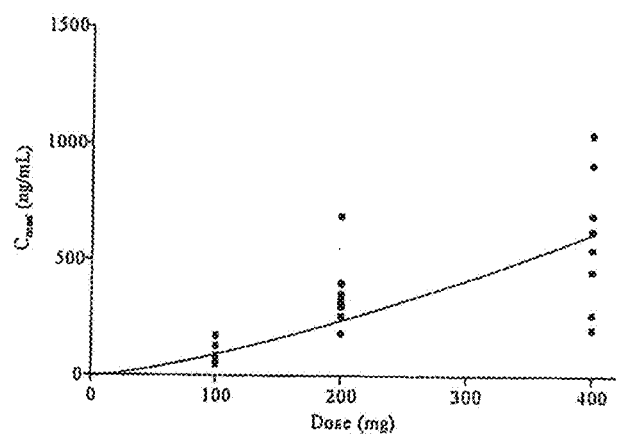
FIG. 14b is a plot of dose vs. $C_{max}$ for KAR5417 in fed healthy volunteers following BID oral administration of KAR5585 for 14 days.
Figure 15A:
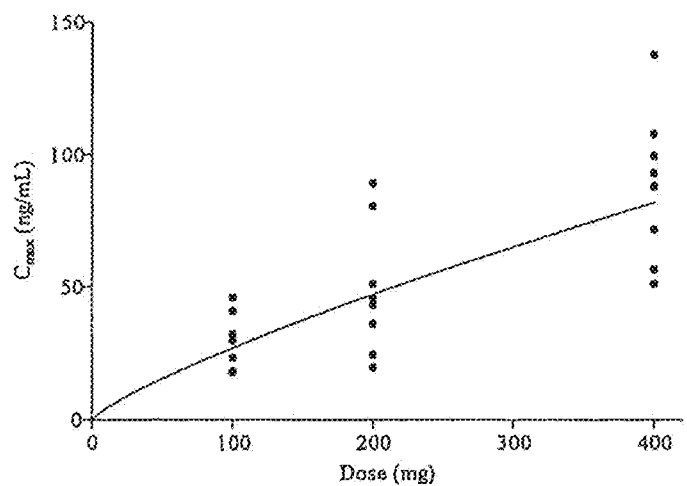
FIG. 15a is a plot of dose vs. $C_{max}$ for KAR5585 in fed healthy volunteers following BID oral administration of KAR5585 for 14 days.
Figure 15B:
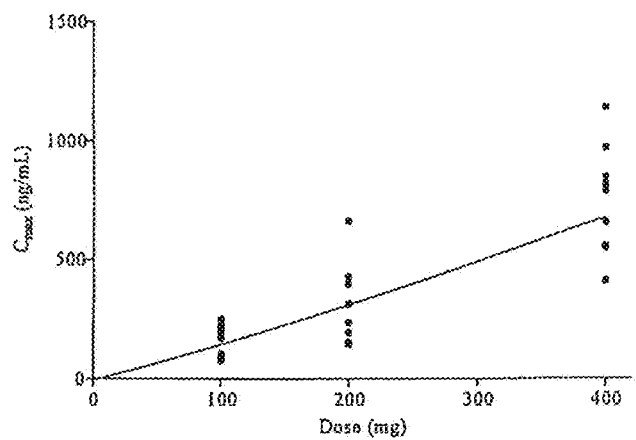
FIG. 15b is a plot of dose vs. $C_{max}$ for KAR5417 in fed healthy volunteers following BID oral administration of KAR5585 for 14 days.
Figure 16A:
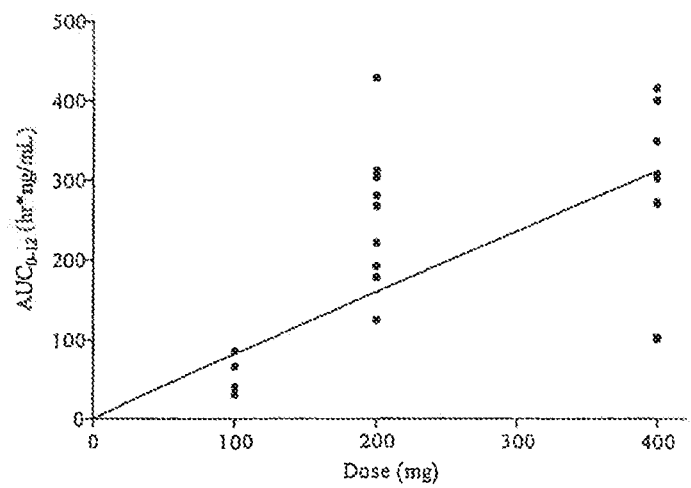
FIG. 16a is a plot of dose vs. $AUC_{0-12}$ for KAR5585 in fed healthy volunteers following BID oral administration of KAR5585 for 14 days.
Figure 16B:
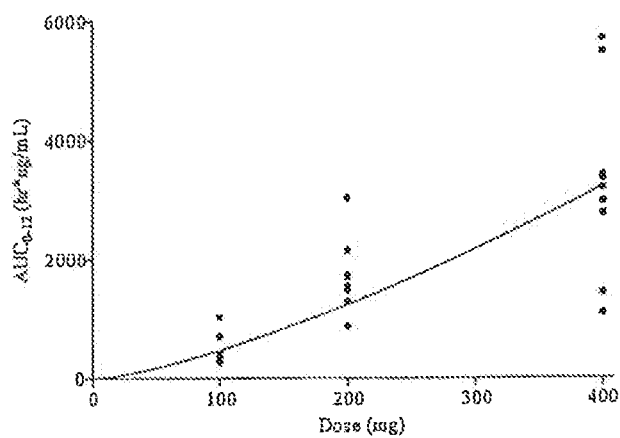
FIG. 16b is a plot of dose vs. $AUC_{0-12}$ for KAR5417 in fed healthy volunteers following BID oral administration of KAR5585 for 14 days.
Figure 17A:
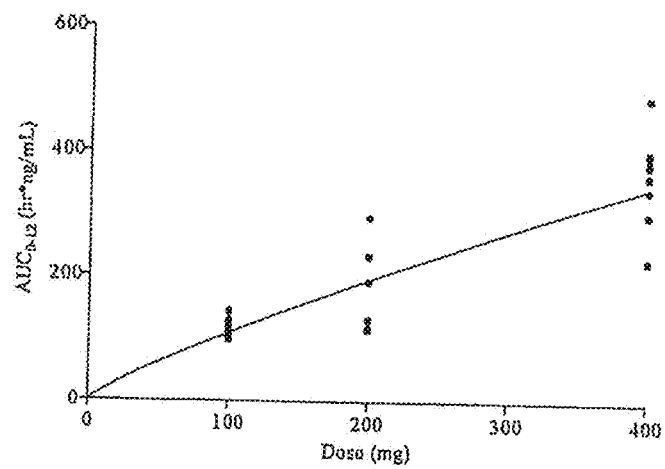
FIG. 17a is a plot of dose vs. $AUC_{0-12}$ for KAR5585 in fed healthy volunteers following BID oral administration of KAR5585 for 14 days.
Figure 17B:
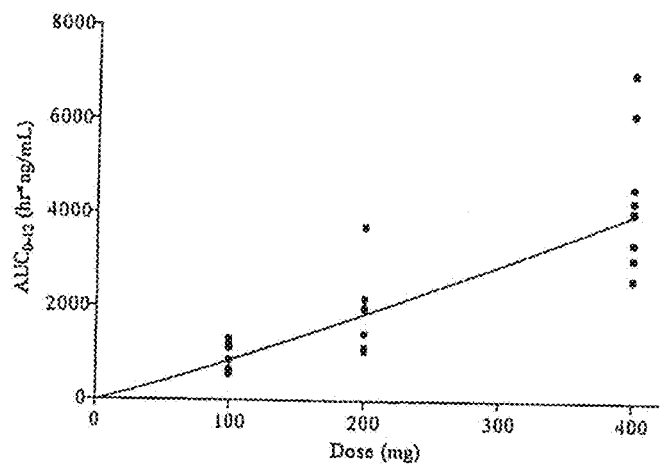
FIG. 17b is a plot of dose vs. $AUC_{0-12}$ for KAR5417 in fed healthy volunteers following BID oral administration of KAR5585 for 14 days.
Figure 18A:
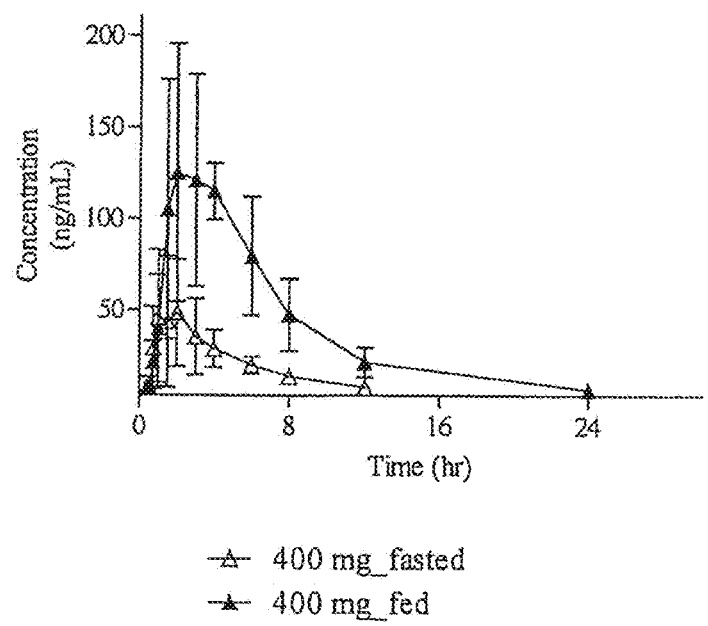
FIG. 18a is a plot of mean (±SD) plasma concentration-time profiles of KAR5585 following administration of 400 mg of KAR5585 under fed and fasting conditions—Cohorts 3A and 3B (linear scale).
Figure 18B:
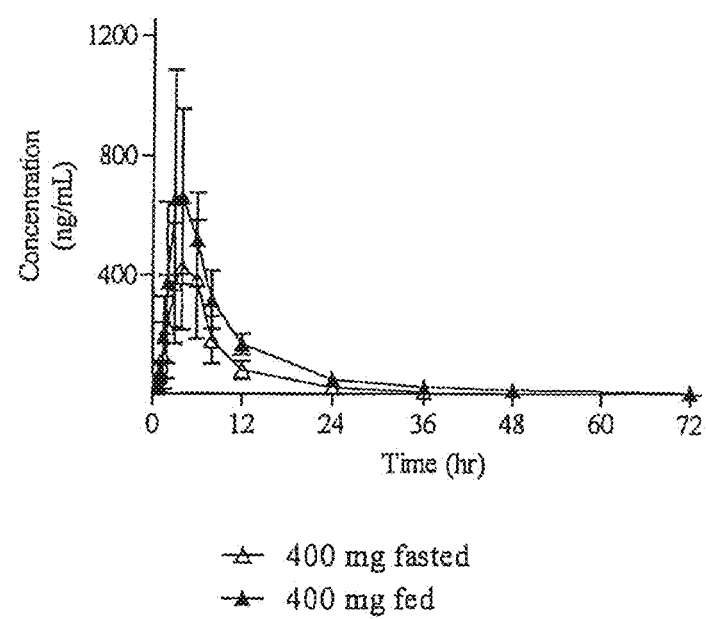
FIG. 18b is a plot of mean (±SD) plasma concentration-time profiles of KAR5417 following administration of 400 mg of KAR5585 under fed and fasting conditions—Cohorts 3A and 3B (linear scale).

Plasma Concentrations:

Mean plasma concentration-time profiles of KAR5585 and KAR5417 following administration of 100 mg KAR5585 under fasting conditions (Part 2, Cohort 1) and 100, 200 and 400 mg KAR5585 under fed conditions (Part 2, Cohorts 2-4) in healthy adult subjects twice daily for 14-days (semi-log scale) are presented in FIGS. 9a and 9b.

Mean (±SD) plasma concentration-time profiles of KAR5585 and KAR5417 following administration of 100 mg KAR5585 under fasting conditions (Part 2, Cohort 1) and 100, 200 and 400 mg KAR5585 under fed conditions (Part 2, Cohorts 2-4) twice-daily for 14-days in healthy adult subjects (semi-log scale) are presented in FIGS. 10 to 13, respectively.

For Part 2, Cohort 1 (fasted state), samples for KAR5585 and KAR5417 PK analysis were collected on Day 1 and Day 14 following the morning dose of KAR5585. For Part 2, Cohorts 2-4 (fed state), samples for PK analysis were collected on Day 1 and Day 7 following the morning and evening doses and following the single morning dose of KAR5585 that was administered on Day 14.

KAR5585 Plasma Concentrations:

In general, KAR5585 was detectable in circulation at each dose level, and concentrations generally increased with escalating dose. In addition, the length of time with measurable KAR5585 concentrations increased at higher dose levels.

The peak plasma KAR5585 concentrations were reached between 0.75-2.0 and 0.75 and 3.0 hours on Day 1 and Day 14 following oral twice-daily administration of 100 mg of KAR5585, Part 2, Cohort 1 (fasted state). The peak mean concentrations of KAR5585 were 16.7 and 21.3 ng/mL on Day 1 and Day 14, respectively.

For doses of 100, 200 and 400 mg of KAR5585, Part 2, Cohorts 2-4 (fed state), the time to median peak plasma concentrations of KAR5585 ranged from 0.75-4 hours, 1.5 to 6 hours, and 1.5 to 6 hours, respectively, on all dosing days and times. There was some evidence for delayed absorption of KAR5585 on Day 7 for the evening dose, where the $t_{max}$ of KAR5585 were 4 hours, 6 hours, and 6 hours, for the 100, 200 and 400 mg doses, respectively. The Day 7 PM $t_{max}$ values were on the upper end of the $t_{max}$ values determined in Day 1, Day 7 and Day 14.

The peak mean concentrations of KAR5585 for doses of 100, 200 and 400 mg KAR5585, Part 2, Cohorts 2-4 (fed state), increased with dose. For doses of 100, 200 and 400 mg KAR5585, Part 2, Cohorts 2-4 (fed state), the mean $C_{max}$ plasma concentrations of KAR5585 ranged from 18.4-44.1 ng/mL, 42.6-90.9 ng/mL, and 69.0-124 ng/mL, respectively, on all dosing days.

There was some evidence for delayed absorption of KAR5585 on Day 7 for the evening dose, where the mean $C_{max}$ concentrations of KAR5585 for the 100, 200 and 400 mg doses were 28.4 ng/mL, 42.6 ng/mL, and 69 ng/mL, respectively. The Day 7 PM $C_{max}$ values were lower than Day 7 AM $C_{max}$, and at the lower end of the $C_{max}$ values determined for all doses on Day 1, Day 7 and Day 14.

Following administration of 100 mg KAR5585, peak mean plasma KAR5585 concentrations were observed at similar times under fed relative to fasting conditions. Median $t_{max}$ values were 0.75 and 1.5 hour postdose, for fed and fasted states on Day 1, and were 1.8 and 1.0 hour postdose, for fed and fasted states on Day 14, respectively.

The peak mean concentrations of KAR5585 were comparable under fed conditions (Day 1 $C_{max}$=18.4 ng/mL; Day 14 $C_{max}$=30 ng/mL,) relative to fasting conditions (Day 1 $C_{max}$=16.7 ng/mL; Day 14 $C_{max}$=21.3 ng/mL). This observation is in contrast to the food effect comparison in Part 1, Cohort 3A and 3B (400 mg KAR5585). In Part 1, a high-fat, high calorie meal resulted in peak mean peak concentrations of KAR5585 that were approximately 320% higher following drug administration under fed conditions ($C_{max}$=169 ng/mL) relative to fasting conditions ($C_{max}$=52.8 ng/mL). It should be noted that in Part 1, the food effect was evaluated in a cross-over fashion within the same subjects while the food effect was assessed in parallel (different subjects fed versus fasted) in Part 2.

KAR5417 Plasma Concentrations:

In general, circulating concentrations of KAR5417 were notably higher than those for KAR5585 on all days and at all dose levels. In addition, KAR5417 concentrations generally increased with increasing doses of KAR5585.

The peak plasma KAR5417 concentrations were reached between 2.0-6.0 and 2.0 and 4.0 hours on Day 1 and Day 14 following oral twice-daily administration of 100 mg of KAR5585, Part 2, Cohort 1 (fasted state). The mean peak concentrations of KAR5417 were 121 and 194 ng/mL on Day 1 and Day 14, respectively. These values were approximately 7.25-fold and 9.1-fold greater than the corresponding peak mean concentrations of KAR5585.

For doses of 100, 200 and 400 mg of KAR5585, Part 2, Cohorts 2-4 (fed state), the time to median peak plasma concentrations of KAR5417 ranged from 2 to 6 hours, 3 to 8 hours, and 3 to 6 hours, respectively, on all dosing days and times. There was some evidence for a delayed $t_{max}$ for KAR5417 on Day 7 for the evening dose, where the median time to peak plasma concentrations of KAR5417 was 6 hours, 8 hours, and 6 hours, for the 100, 200 and 400 mg doses, respectively. The Day 7 PM median $t_{max}$ values for KAR5417 were on the upper end of the median $t_{max}$ values determined on Day 1, Day 7 and Day 14.

The peak mean concentrations of KAR5417 for doses of 100, 200 and 400 mg KAR5585, Part 2, Cohorts 2-4 (fed state), increased with dose. For doses of 100, 200 and 400 mg KAR5585, Part 2, Cohorts 2-4 (fed state), the mean $C_{max}$ plasma concentrations of KAR5417 ranged from 85.9-168 ng/mL, 222-359 ng/mL, and 595-1000 ng/mL, respectively, on all dosing days. There was some evidence for delayed absorption of KAR5585 and a corresponding lowered KAR5417 $C_{max}$ on Day 7 for the evening dose, where the mean $C_{max}$ concentrations of KAR5417 for the 100, 200 and 400 mg doses were 112 ng/mL, 222 ng/mL, and 608 ng/mL, respectively. The Day 7 PM $C_{max}$ values were lower than Day 7 AM $C_{max}$, and on the lower end of the mean $C_{max}$ values determined for all doses on Day 1, Day 7 and Day 14.

Following administration of 100 mg KAR5585, peak mean plasma KAR5417 concentrations were observed at similar times under fed relative to fasting conditions. Median $t_{max}$ values were 2.0 and 3.0 hour postdose, for fed and fasted states on Day 1, and were 3.0 and 3.0 hour postdose, for fed and fasted states on Day 14 respectively). The peak mean concentrations of KAR5417 were comparable under fed conditions (Day 1 $C_{max}$=85.9 ng/mL; Day 14 $C_{max}$=168 ng/mL,) relative to fasting conditions (Day 1 $C_{max}$=121 ng/mL; Day 14 $C_{max}$=194 ng/mL). This observation is in contrast to the food effect comparison in Part 1, Cohort 3A and 3B (400 mg KAR5585. In Part 1, a high fat, high calorie meal resulted in peak mean concentrations of KAR5417 that were approximately 177% higher following KAR5585 administration under fed conditions ($C_{max}$ 860 ng/mL) relative to fasting conditions ($C_{max}$=485 ng/mL). Again, it should be noted that the food effect was evaluated in a cross-over fashion in Part 1 while the food effect was assessed in parallel (different subjects fed versus fasted) in Part 2.

Pharmacokinetics Parameters:

The summary of plasma KAR5585 and KAR5417 PK parameters following a repeat-dose oral administration of 100, 200 and 400 mg KAR5585 administered in healthy adult subjects are presented in 15 and Table 16, respectively. Accumulation ratios for KAR5417 and KAR5585 in healthy volunteers following BID oral administration of KAR5585 for 14 days are presented in Table 17.

Pharmacokinetics of KAR5585:

In general, mean peak plasma KAR5585 concentrations, as measured by mean $C_{max}$, appeared to increase in a dose proportional manner from 100-400 mg (Part 2, Cohort 2-4, fed state). Mean $C_{max}$ values increased 4.4-fold over the 4-fold increase in dose between the 100 mg dose (Cohort 2) and the 400 mg dose (Cohort 4) on Day 1. Mean $C_{max}$ values increased ~3.0-fold over the 4-fold increase in dose between the 100 mg dose (Part 2, Cohort 2) and the 400 mg dose (Part 2, Cohort 4) on Day 14.

Overall, the mean extent of systemic exposure to KAR5585, as measured by mean $AUC_{012}$ and $AUC_{0-24}$, appeared to increase in a dose proportional manner between the 100 and 400 mg dose levels, with a 5.1-fold and 3.6-fold increase in mean $AUC_{0-12}$ and mean $AUC_{0-24}$ estimates, respectively, for a 4-fold increase in dose between the 100 mg dose (Part 2, Cohort 2) and the 400 mg dose (Part 2, Cohort 4) on Day 1. Mean $AUC_{0-12}$ and mean $AUC_{0-24}$ estimates, increased 3.1-fold and 3.6-fold respectively, for a 4-fold increase in dose between the 100 mg dose (Part 2, Cohort 2) and the 400 mg dose (Part 2, Cohort 4) on Day 14.

Overall, the mean extent of systemic exposure to KAR5585, as measured by mean $AUC_{0-12}$ and $AUC_{0-24}$, appeared to be comparable under fasted conditions (Part 2, Cohort 1; Day 1 $AUC_{0-12}$=62.8 hr*ng/mL; Day 14 $AUC_{0-24}$=99.8 hr*ng/mL,) relative to fed conditions (Part 2, Cohort 2; Day 1 AM $AUC_{0-12}$=55.5 hr*ng/mL; Day 14 $AUC_{0-24}$=122 hr*ng/mL,). This observation was in contrast to the food effect comparison in Part 1, Cohort 3A and 3B (400 mg KAR5585). In Part 1, a high fat, high calorie meal resulted in $AUC_{0-inf}$ of KAR5585 that were approximately 3.0-fold higher following drug administration of KAR5585 400 mg under fed conditions ($AUC_{0-inf}$=915 ng·hr/mL) relative to fasting conditions ($AUC_{0-inf}$=302 ng·hr/mL). Again, the food effect was evaluated in a cross-over fashion in Part 1 while the food effect was assessed in parallel (different subjects fed versus fasted) in Part 2.

The mean apparent elimination half-life of KAR5585 increased with increasing dose levels, and the mean values were 2.73, 4.08 and 6.45 hrs on Day 14 after oral administration of repeat dose twice-daily administration of 100, 200 and 400 mg of KAR5585 (Part 2, Cohort 2-4, fed state), respectively. The half-life of KAR5585 was 2.49 hrs on Day 14 after oral administration of repeat dose administration of 100 mg in the fasted state, and was comparable to the half-life in the fed state (2.73 hrs) for the 100 mg dose.

Mean CL/F estimates of KAR5585 were 2100, 830 and 1730 L/h for the 100, 200 and 400 mg (Part 2, Cohort 2-4, fed state) doses on Day 1, respectively. Mean steady-state CL/F estimates of KAR5585, in the fed state, were 880, 1200 and 1140 L/h for the 100, 200 and 400 mg (Part 2, Cohort 2-4, fed state) doses on Day 14, respectively. Ranges (mean±SD) were generally overlapping on both days and across the dose range studied here.

There was a slight trend for increasing $V_z/F$ increased with increasing dose levels on Day 1, noting that the ranges (mean±SD) were generally overlapping. Mean $V_z/F$ was 4100, 3220 and 6800 L for the 100, 200 and 400 mg (Part 2, Cohort 2-4, fed state) doses, respectively. On Day 14, the $V_z/F$ increased with increasing dose levels on Day 14 and were 3520, 7010 and 10300 L for the 100, 200 and 400 mg doses, respectively. The highest mean $V_z/F$ values were noted for the 400 mg dose (Cohort 4) and is attributed to better characterization of the elimination half-life of KAR5585 at higher doses.

KAR5585 plasma levels achieved steady-state exposure by Day 7 as assessed by comparison of Day 7 and Day 14 $AUC_{0-12}$ and concentration, obtained 12 hours after an administered dose ($C_{12hr}$) values following twice daily administration of KAR5585 for 14-days. Accumulation ratios for KAR5585 comparing accumulation ratio for $C_{max}$ ($R_{Cmax}$) and accumulation ratio for $AUC_{0-12}$ ($R_{AUC0-12}$) for Day 7/1 and Day 14/Day 1 are presented in Table 17. The $R_{AUC0-12}$ values for KAR5585 ranged from 2.75-3.32, 0.76-0.93 and 1.6-2.01 for the 100, 200 and 400 mg doses of KAR5585 suggesting that the PK of KAR5417 was independent of time and steady-state was achieved on Day 7 following repeated twice-daily administration for 14-days.

Pharmacokinetics of KAR5417

KAR5417 is the active metabolite of the prodrug, KAR5585. Following administration of KAR5585, KAR5417 appeared in plasma, an observation consistent with rapid absorption of KAR5585 and efficient conversion to KAR5417. In general, mean peak plasma KAR5417 concentrations, as measured by mean $C_{max}$, appeared to increase in a greater that dose proportional manner from 100-400 mg (Part 2, Cohort 2-4, fed state). Mean $C_{max}$ values increased 6.9-fold over the 4-fold increase in dose between the 100 mg dose (Cohort 2) and the 400 mg dose (Cohort 4) on Day 1. Day 14 mean $C_{max}$ values increased in an approximately dose proportional manner with an ~4.5-fold increase in $C_{max}$ over the 4-fold increase in dose between the 100 mg dose (Part 2, Cohort 2) and the 400 mg dose (Part 2, Cohort 4).

Overall, the mean extent of systemic exposure to KAR5417, as measured by mean $AUC_{0-12}$ and $AUC_{0-24}$, appeared to increase in a greater than dose-proportional manner between the 100 and 400 mg dose levels, with a 7.0-fold and 6.45-fold increase in mean $AUC_{0-12}$ and mean $AUC_{0-24}$ estimates, respectively, for 4-fold increase in dose between the 100 mg dose (Part 2, Cohort 2) and the 400 mg dose (Part 2, Cohort 4) on Day 1. Mean $AUC_{0-12}$ and mean $AUC_{0-24}$ estimates, increased 4.6-fold and 4.45-fold respectively, for a 4-fold increase in dose between the 100 mg dose (Part 1, Cohort 2) and the 400 mg dose (Part 2, Cohort 4) on Day 14.

Overall, the mean extent of systemic exposure to KAR5417, as measured by mean $AUC_{0-12}$ and $AUC_{0-24}$, appeared to comparable under fasted conditions (Part 2, Cohort 1; Day 1 $AUC_{0-12}$=741 hr*ng/mL; Day 14 $AUC_{0-24}$=1650 hr*ng/mL,) relative to fed conditions (Part 2, Cohort 2; Day 1 $AUC_{0-12}$=470 hr*ng/mL; Day 14 $AUC_{0-24}$=1220 hr*ng/mL,). This observation is in contrast to the food effect comparison in Part 1, Cohort 3A and 3B (400 mg KAR5585). In Part 1, a high fat, high calorie meal resulted in $AUC_{0-inf}$ of KAR5417 that was approximately 1.8-fold higher following drug administration of KAR5585 400 mg under fed conditions ($AUC_{0-inf}$=6710 ng·hr/mL) relative to fasting conditions ($AUC_{0-inf}$=3650 ng·hr/mL). As noted above, the food effect was evaluated in a cross-over fashion in Part 1 while the food effect was assessed in parallel (different subjects fed versus fasted) in Part 2.

The mean apparent elimination half-life of KAR5417 increased with increasing dose levels studied, and mean values were 19.6, 25.0 and 30.6 hrs on Day 14 after oral administration of repeat dose twice-daily administration of 100, 200 and 400 mg of KAR5585 (Part 2, Cohort 2-4, fed state), respectively, determined from a single AM dose on Day 14. The half-life of KAR5417 was 18.8 hrs on Day 14 after oral administration of repeat dose twice-daily administration of 100 mg in the fasted state, and was comparable to the half-life in the fed state (19.6 hrs) for the 100 mg dose. The elimination half-life (30.6 hrs) of KAR5417 on repeat dose administration of 400 mg KAR5585, was similar to the elimination half-life of KAR5417 (20.5 hrs) following single dose administration of 400 mg KAR5585 (Part 1 Cohort 3B).

KAR5417 plasma levels achieved steady-state exposure by Day 7 as assessed by comparison of Day 7 and Day 14 $AUC_{0-12}$ and $C_{12hr}$ values following twice daily administration of KAR5585 for 14-days. Accumulation ratios for KAR5417 comparing $R_{Cmax}$ and $R_{AUC0-12}$ for Day 7/Day 1 and Day 14/Day 1 are presented in Table 17. The $R_{AUC0-12}$ values for KAR5417 ranged from 2.19-2.57, 1.09-1.34 and 1.65-2.38 for the 100, 200 and 400 mg doses of KAR5585 suggesting that the PK of KAR5417 was independent of time and steady-state was achieved on Day 7 following repeated twice-daily administration for 14-days.

TABLE 13

Mean PK Parameters for KAR5585 in Healthy Volunteers Following BID Oral Administration of KAR5585 for 14 Days (Pharmacokinetic Evaluable Population)

| Dose (mg/dose) | Day/ Period | Stat. Param. | $t_{1/2}$ (hr) | $t_{max}^a$ (hr) | $C_{max}$ (ng/mL) | $C_{max}$/D [(ng/mL)/ mg] | $C_{12}$ (ng/mL) | $C_{24}$ (ng/mL) | $C_{max}$/ $C_{12}$ |
|---|---|---|---|---|---|---|---|---|---|
| 100/Fasted Cohort 1 | 1/ $AM^c$ | N | 4 | 7 | 7 | 7 | 0 | | 0 |
| | | Mean | 2.23 | 1.5 | 16.7 | 0.167 | BLQ | | ND |
| | | SD | 2.07 | 0.75, 2.0 | 5.87 | 0.0587 | NR | | ND |
| | | CV % | 92.8 | NA | 35.0 | 35.0 | NR | | ND |
| | | Geo. Mean | 1.73 | NA | 15.8 | 0.158 | BLQ | | ND |
| | | Geo. CV % | 88.0 | NA | 40.2 | 40.2 | NR | | ND |
| | 14 | N | 7 | 9 | 9 | 9 | 1 | 0 | 1 |
| | | Mean | 2.49 | 1.0 | 21.3 | 0.213 | NR | BLQ | 4.61 |
| | | SD | 0.900 | 0.75, 3.0 | 7.98 | 0.0798 | NR | NR | NR |
| | | CV % | 36.2 | NA | 37.5 | 37.5 | NR | NR | NR |
| | | Geo. Mean | 2.36 | NA | 20.1 | 0.201 | NR | BLQ | 4.61 |
| | | Geo. CV % | 35.8 | NA | 34.8 | 34.8 | NR | NR | NR |
| 100/Fed Cohort 2 | 1/ AM | N | 4 | 9 | 9 | 9 | 0 | | 0 |
| | | Mean | 1.42 | 0.75 | 18.4 | 0.184 | BLQ | | ND |
| | | SD | 0.455 | 0.75, 3.0 | 6.72 | 0.0672 | NR | | ND |
| | | CV % | 32.1 | NA | 36.4 | 36.4 | NR | | ND |
| | | Geo. Mean | 1.37 | NA | 17.7 | 0.177 | BLQ | | ND |
| | | Geo. CV % | 29.3 | NA | 29.7 | 29.7 | NR | | ND |
| | 1/ $PM^c$ | N | 7 | 9 | 9 | 9 | 1 | | 1 |
| | | Mean | 1.87 | 2.0 | 44.1 | 0.441 | NR | | 1.80 |
| | | SD | 0.422 | 1.5, 8.0 | 20.4 | 0.204 | NR | | NR |
| | | CV % | 22.6 | NA | 46.2 | 46.2 | NR | | NR |
| | | Geo. Mean | 1.82 | NA | 39.8 | 0.398 | NR | | 1.80 |
| | | Geo. CV % | 25.4 | NA | 53.9 | 53.9 | NR | | NR |
| | 7/ AM | N | 8 | 9 | 9 | 9 | 0 | | 0 |
| | | Mean | 2.86 | 2.0 | 31.3 | 0.313 | BLQ | | ND |
| | | SD | 0.544 | 1.5, 4.0 | 11.3 | 0.113 | NR | | ND |
| | | CV % | 19.0 | NA | 35.9 | 35.9 | NR | | ND |
| | | Geo. Mean | 2.82 | NA | 29.8 | 0.298 | BLQ | | ND |
| | | Geo. CV % | 17.8 | NA | 34.4 | 34.4 | NR | | ND |
| | 7/ PM | N | 5 | 9 | 9 | 9 | 5 | | 5 |
| | | Mean | 3.80 | 4.0 | 28.4 | 0.284 | 6.29 | | 5.37 |
| | | SD | 1.62 | 1.5, 6.0 | 15.1 | 0.151 | 0.633 | | 3.59 |
| | | CV % | 42.6 | NA | 53.0 | 53.0 | 10.0 | | 66.9 |
| | | Geo. Mean | 3.52 | NA | 25.8 | 0.258 | 6.27 | | 4.66 |
| | | Geo. CV % | 46.2 | NA | 47.2 | 47.2 | 10.0 | | 61.2 |
| | 14 | N | 7 | 8 | 8 | 8 | 0 | 0 | 0 |
| | | Mean | 2.73 | 1.8 | 30.0 | 0.300 | BLQ | BLQ | ND |

TABLE 13-continued

Mean PK Parameters for KAR5585 in Healthy Volunteers Following BID Oral Administration of KAR5585 for 14 Days (Pharmacokinetic Evaluable Population)

| | | | | | | | | | |
|---|---|---|---|---|---|---|---|---|---|
| | | SD | 0.759 | 0.75, 3.0 | 10.0 | 0.100 | NR | NR | ND |
| | | CV % | 27.8 | NA | 33.5 | 33.5 | NR | NR | ND |
| | | Geo. Mean | 2.64 | NA | 28.5 | 0.285 | BLQ | BLQ | ND |
| | | Geo. CV % | 28.1 | NA | 35.3 | 35.3 | NR | NR | ND |
| 200/Fed Cohort 3 | 1/ AM[c] | N | 9 | 9 | 9 | 9 | 6 | | 6 |
| | | Mean | 2.91 | 1.5 | 87.8 | 0.439 | 5.61 | | 18.7 |
| | | SD | 0.806 | 0.75, 4.0 | 39.8 | 0.199 | 0.268 | | 6.66 |
| | | CV % | 27.7 | NA | 45.3 | 45.3 | 4.8 | | 35.6 |
| | | Geo. Mean | 2.81 | NA | 80.7 | 0.403 | 5.60 | | 17.7 |
| | | Geo. CV % | 30.9 | NA | 45.0 | 45.0 | 4.8 | | 37.4 |
| 400/Fed Cohort 4 | 1/ AM[c] | N | 9 | 9 | 9 | 9 | 6 | | 6 |
| | | Mean | 3.14 | 2.0 | 81.8 | 0.205 | 7.49 | | 12.8 |
| | | SD | 0.913 | 1.0, 2.0 | 34.9 | 0.0872 | 0.927 | | 4.03 |
| | | CV % | 29.1 | NA | 42.6 | 42.6 | 12.4 | | 31.5 |
| | | Geo. Mean | 3.00 | NA | 74.0 | 0.185 | 7.44 | | 12.2 |
| | | Geo. CV % | 33.7 | NA | 54.0 | 54.0 | 13.0 | | 36.9 |
| | 1/ PM[c] | N | 9 | 9 | 9 | 9 | 9 | | 9 |
| | | Mean | 4.33 | 3.0 | 124 | 0.310 | 17.1 | | 7.56 |
| | | SD | 1.23 | 2.0, 4.1 | 56.1 | 0.140 | 3.77 | | 3.25 |
| | | CV % | 28.4 | NA | 45.2 | 45.2 | 22.1 | | 43.0 |
| | | Geo. Mean | 4.18 | NA | 1100 | 0.276 | 16.6 | | 6.64 |
| | | Geo. CV % | 29.6 | NA | 61.0 | 61.0 | 25.4 | | 67.9 |
| | 7/ AM[c] | N | 9 | 9 | 9 | 9 | 9 | | 9 |
| | | Mean | 4.90 | 2.0 | 95.9 | 0.240 | 15.5 | | 6.27 |
| | | SD | 1.85 | 1.5, 4.0 | 30.7 | 0.0769 | 3.86 | | 1.76 |
| | | CV % | 37.7 | NA | 32.1 | 32.1 | 24.8 | | 28.0 |
| | | Geo. Mean | 4.65 | NA | 91.3 | 0.228 | 15.1 | | 6.04 |
| | | Geo. CV % | 33.6 | NA | 34.7 | 34.7 | 24.6 | | 30.5 |
| | 7/ PM[c] | N | 4 | 9 | 9 | 9 | 9 | | 9 |
| | | Mean | 0.93 | 6.0 | 69.0 | 0.172 | 20.8 | | 3.90 |
| | | SD | 3.35 | 2.0, 8.0 | 30.8 | 0.0769 | 5.76 | | 2.92 |
| | | CV % | 7.17 | NA | 44.6 | 44.6 | 27.6 | | 74.7 |
| | | Geo. Mean | 4.92 | NA | 63.4 | 0.158 | 20.1 | | 3.15 |
| | | Geo. GV % | 7.22 | NA | 45.8 | 45.8 | 29.9 | | 75.7 |
| | 1/ PM | N | 8 | 9 | 9 | 9 | 9 | | 9 |
| | | Mean | 4.34 | 3.0 | 90.9 | 0.455 | 9.92 | | 9.98 |
| | | SD | 1.03 | 1.5, 6.0 | 29.6 | 0.148 | 2.81 | | 4.65 |
| | | CV % | 23.7 | NA | 32.6 | 32.6 | 28.4 | | 46.5 |
| | | Geo. Mean | 4.24 | NA | 85.4 | 0.427 | 0.37 | | 8.93 |
| | | Geo. CV % | 24.2 | NA | 41.8 | 41.8 | 29.4 | | 56.2 |
| | 7/ AM[c] | N | 9 | 9 | 9 | 9 | 8 | | 8 |
| | | Mean | 4.30 | 3.0 | 48.8 | 0.244 | 7.71 | | 6.69 |
| | | SD | 0.938 | 2.0, 4.0 | 18.9 | 0.0943 | 2.78 | | 2.02 |
| | | CV % | 21.8 | NA | 38.7 | 38.7 | 36.1 | | 30.2 |
| | | Geo. Mean | 4.21 | NA | 45.6 | 0.228 | 7.36 | | 6.43 |
| | | Geo. CV % | 22.1 | Na | 40.7 | 40.7 | 31.7 | | 31.3 |
| | 7/ PM[c] | N | 2 | 8 | 8 | 8 | 8 | | 8 |
| | | Mean | 6.20 | 6.0 | 42.6 | 0.213 | 12.2 | | 4.20 |
| | | SD | NR | 2.0, 8.0 | 19.5 | 0.0976 | 5.46 | | 3.14 |
| | | CV % | NR | NA | 45.8 | 45.8 | 44.6 | | 74.7 |
| | | Geo. Mean | 5.58 | NA | 39.1 | 0.195 | 11.3 | | 3.46 |
| | | Geo. CV % | NR | NA | 46.4 | 46.4 | 43.6 | | 68.5 |
| | 14 | N | 7 | 8 | 8 | 8 | 3 | 0 | 3 |
| | | Mean | 4.98 | 2.0 | 48.8 | 0.244 | NR | BLQ | 11.2 |
| | | SD | 1.06 | 1.0, 6.0 | 24.8 | 0.124 | NR | NR | 4.75 |
| | | CV % | 25.9 | NA | 50.8 | 50.8 | NR | NR | 42.3 |
| | | Geo. Meas | 3.94 | NA | 43.5 | 0.217 | NR | BLQ | 10.5 |
| | | Geo. | 31.0 | NA | 56.0 | 56.0 | NR | NR | 48.9 |

TABLE 13-continued

Mean PK Parameters for KAR5585 in Healthy Volunteers Following BID Oral Administration of KAR5585 for 14 Days (Pharmacokinetic Evaluable Population)

|  |  | CV % |  |  |  |  |  |  |  |
|---|---|---|---|---|---|---|---|---|---|
|  | 14 | N | 9 | 9 | 9 | 9 | 9 | 3 | 9 |
|  |  | Mean | 6.45 | 1.5 | 89.0 | 0.222 | 11.4 | NR | 8.17 |
|  |  | SD | 2.48 | 1.0, 2.0 | 26.6 | 0.0664 | 3.37 | NR | 3.00 |
|  |  | CV % | 38.4 | NA | 29.8 | 29.8 | 29.6 | NR | 36.7 |
|  |  | Geo. Mean | 6.08 | NA | 85.3 | 0.213 | 11.0 | NR | 7.76 |
|  |  | Geo. cv % | 36.1 | NA | 32.0 | 32.0 | 28.4 | NR | 33.7 |

| Dose (mg/dose) | Day/ Period | Stat. Param. | $AUC^b_{0-12}$ (hr*ng/mL) | $AUC_{0-24}$ (hr*ng/mL) | $AUC_{0-24}/D$ [(hr*ng/mL)/mg] | $AUC_{0-\infty}$ (hr*ng/mL) | $V_z/F$ (L) | CL/F (L/hr) |
|---|---|---|---|---|---|---|---|---|
| 100/Fasted Cohort 1 | 1/ $AM^c$ | N | 4 |  |  | 4 | 4 | 4 |
|  |  | Mean | 62.8 |  |  | 71.1 | 4900 | 2380 |
|  |  | SD | 45.6 |  |  | 60.8 | 1980 | 1820 |
|  |  | CV % | 72.7 |  |  | 85.5 | 40.4 | 76.3 |
|  |  | Geo. Mean | 50.8 |  |  | 54.1 | 4620 | 1850 |
|  |  | Geo. CV % | 89.7 |  |  | 105 | 40.7 | 105 |
|  | 14 | N | 8 | 8 | 8 | 7 | 7 | 8 |
|  |  | Mean | 92.4 | 99.8 | 0.998 | 105 | 4420 | 1450 |
|  |  | SD | 64.5 | 76.3 | 0.763 | 82.7 | 1370 | 713 |
|  |  | CV % | 69.9 | 76.4 | 76.4 | 78.6 | 30.9 | 49.0 |
|  |  | Geo. Mean | 78.2 | 82.3 | 0.823 | 85 | 4230 | 1280 |
|  |  | Geo. CV % | 63.6 | 68.9 | 68.9 | 75.8 | 34.5 | 63.6 |
| 100/Fed Cohort 2 | 1/ AM | N | 4 |  |  | 4 | 4 | 4 |
|  |  | Mean | 55.5 |  |  | 55.9 | 4100 | 2100 |
|  |  | SD | 24.9 |  |  | 24.9 | 1510 | 945 |
|  |  | CV % | 44.9 |  |  | 44.6 | 36.7 | 45.1 |
|  |  | Geo. Mean | 51.2 |  |  | 51.7 | 3830 | 1940 |
|  |  | Geo. CV % | 49.2 |  |  | 49.2 | 49.2 | 49.2 |
|  | 1/ $PM^c$ | N | 8 | 3 | 3 | 7 | 7 | 7 |
|  |  | Mean | 143 | 226 | 1.13 | 156 | 1820 | 675 |
|  |  | SD | 48.8 | 90.2 | 0.451 | 42.9 | 588 | 154 |
|  |  | CV % | 34.0 | 40.0 | 40.0 | 27.4 | 32.3 | 22.9 |
|  |  | Geo. Mean | 136 | 214 | 1.07 | 152 | 1730 | 658 |
|  |  | Geo. CV % | 35.9 | 41.3 | 41.3 | 25.4 | 35.7 | 25.4 |
|  | 7/ AM | N | 8 |  |  | 8 | 8 | 8 |
|  |  | Mean | 129 |  |  | 139 | 3360 | 800 |
|  |  | SD | 25.2 |  |  | 23.4 | 1110 | 142 |
|  |  | CV % | 19.5 |  |  | 16.9 | 32.9 | 17.7 |
|  |  | Geo. Mean | 127 |  |  | 137 | 3210 | 788 |
|  |  | Geo. CV % | 18.7 |  |  | 16.4 | 34.1 | 18.7 |
|  | 7/ PM | N | 7 | 6 | 6 | 5 | 5 | 5 |
|  |  | Mean | 145 | 282 | 1.41 | 173 | 3910 | 717 |
|  |  | SD | 37.6 | 55.0 | 0.275 | 48.5 | 1850 | 165 |
|  |  | CV % | 25.9 | 19.5 | 19.5 | 28.0 | 47.2 | 23.0 |
|  |  | Geo. Mean | 142 | 278 | 1.39 | 168 | 3550 | 699 |
|  |  | Geo. CV % | 22.8 | 18.5 | 18.5 | 28.6 | 53.7 | 27.1 |
|  | 14 | N | 7 | 7 | 7 | 7 | 7 | 7 |
|  |  | Mean | 115 | 122 | 1.22 | 122 | 3520 | 880 |
|  |  | SD | 16.0 | 15.5 | 0.155 | 14.5 | 1290 | 115 |
|  |  | CV % | 13.9 | 12.7 | 12.7 | 11.9 | 36.7 | 13.0 |
|  |  | Geo. Mean | 114 | 121 | 1.21 | 121 | 3330 | 874 |
|  |  | Geo. CV % | 13.5 | 12.3 | 12.3 | 11.7 | 37.7 | 13.5 |
| 200/Fed Cohort 3 | 1/ $AM^c$ | N | 9 |  |  | 9 | 9 | 9 |
|  |  | Mean | 257 |  |  | 275 | 3220 | 830 |
|  |  | SD | 89.8 |  |  | 98.3 | 750 | 350 |
|  |  | CV % | 34.9 |  |  | 35.7 | 23.3 | 42.1 |
|  |  | Geo. Mean | 243 |  |  | 258 | 3130 | 774 |
|  |  | Geo. | 37.8 |  |  | 40.1 | 26.0 | 40.1 |

TABLE 13-continued

Mean PK Parameters for KAR5585 in Healthy Volunteers Following BID Oral Administration of KAR5585 for 14 Days (Pharmacokinetic Evaluable Population)

| | | | | | | | | |
|---|---|---|---|---|---|---|---|---|
| 400/Fed Cohort 4 | 1/ AM[c] | N | 9 | | | 0 | 9 | 9 |
| | | Mean | 2.81 | | | 305 | 6800 | 1730 |
| | | SD | 113 | | | 127 | 2760 | 1200 |
| | | CV % | 40.2 | | | 41.5 | 40.5 | 69.2 |
| | | Geo. Means | 25.3 | | | 272 | 6360 | 1470 |
| | | Geo. CV % | 57.3 | | | 61.2 | 39.6 | 61.2 |
| | 1/ PM[c] | N | 9 | 9 | 9 | 7 | 7 | 7 |
| | | Meant | 528 | 808 | 1.01 | 657 | 4030 | 662 |
| | | SD | 169 | 264 | 0.330 | 182 | 1400 | 241 |
| | | CV % | 32.0 | 32.7 | 32.7 | 27.7 | 34.6 | 36.4 |
| | | Geo. Mean | 501 | 760 | 0.950 | 633 | 3820 | 632 |
| | | Geo. CV % | 36.1 | 41.3 | 41.3 | 32.1 | 38.0 | 32.1 |
| | 7/ AM[c] | N | 9 | | | 9 | 9 | 9 |
| | | Mean | 483 | | | 588 | 6220 | 865 |
| | | SD | 102 | | | 124 | 3230 | 198 |
| | | CV % | 21.1 | | | 21.1 | 51.9 | 22.9 |
| | | Geo. Meaa | 473 | | | 577 | 5680 | 846 |
| | | Geo. CV % | 22.4 | | | 21.9 | 45.0 | 22.4 |
| | 7/ PM[c] | N | 9 | 9 | 9 | 4 | 4 | 4 |
| | | Mean | 404 | 887 | 1.11 | 538 | 6950 | 969 |
| | | SD | 96.3 | 185 | 0.231 | 77.1 | 1800 | 196 |
| | | CV % | 23.8 | 20.9 | 20.39 | 14.3 | 25.9 | 20.3 |
| | | Geo. Mean | 394 | 870 | 1.09 | 534 | 6770 | 954 |
| | | Geo. GV % | 23.9 | 21.6 | 21.6 | 14.3 | 27.5 | 21.0 |
| | 7/ PM | N | 9 | 9 | 9 | 8 | 8 | 8 |
| | | Mean | 344 | 601 | 1.5 | 417 | 3120 | 507 |
| | | SD | 90.8 | 156 | 0.389 | 102 | 785 | 129 |
| | | CV % | 26.4 | 25.9 | 25.9 | 24.4 | 25.2 | 25.6 |
| | | Geo. Mean | 333 | 583 | 1.46 | 406 | 3010 | 493 |
| | | Geo. CV % | 27.5 | 26.5 | 26.5 | 25.5 | 30.2 | 25.5 |
| | 7/ AM[c] | N | 9 | | | 0 | 9 | 9 |
| | | Mean | 230 | | | 273 | 5960 | 978 |
| | | SD | 83.9 | | | 101 | 2150 | 342 |
| | | CV % | 36.5 | | | 36.9 | 36.0 | 35.0 |
| | | Geo. Mean | 217 | | | 256 | 5610 | 924 |
| | | Geo. CV % | 37.4 | | | 39.1 | 38.4 | 37.4 |
| | 7/ PM[c] | N | 8 | 8 | 8 | 2 | 2 | 2 |
| | | Mean | 207 | 431 | 1.08 | 290 | 8710 | 890 |
| | | SD | 53.9 | 133 | 0.332 | NR | NR | NR |
| | | CV % | 26.1 | 30.8 | 30.8 | NR | NR | NR |
| | | Geo. Mean | 201 | 414 | 1.03 | 289 | 7000 | 869 |
| | | Geo. CV % | 25.7 | 30.8 | 30.8 | NR | NR | NR |
| | 14 | N | 7 | 7 | 7 | 7 | 7 | 7 |
| | | Mean | 188 | 212 | 1.06 | 216 | 7010 | 1200 |
| | | SD | 69.9 | 81.7 | 0.409 | 83.9 | 3070 | 447 |
| | | CV % | 37.2 | 38.6 | 38.6 | 38.9 | 43.8 | 37.2 |
| | | Geo. Meas | 177 | 199 | 0.993 | 202 | 6430 | 1130 |
| | | Geo. CV % | 39.6 | 40.9 | 46.9 | 41.3 | 48.2 | 39.6 |
| | 14 | N | 9 | 9 | 9 | 9 | 9 | 9 |
| | | Mean | 366 | 444 | 1.11 | 482 | 10300 | 1140 |
| | | SD | 72.6 | 103 | 0.257 | 138 | 3420 | 270 |
| | | CV % | 19.8 | 23.2 | 23.2 | 28.6 | 33.4 | 23.7 |
| | | Geo. Mean | 359 | 433 | 1.08 | 465 | 9780 | 1110 |
| | | Geo. cv % | 21.7 | 24.4 | 24.4 | 29.2 | 33.6 | 21.7 |

[a]Median and range (Min, Max) presented;
[b]AUC$_{0-t}$ substituted for AUC$_{0-12}$ when WinNonlin did not calculate the latter and tlast was >11.90 hr;
[c]AM refers to a morning dose (8AM) and PM refers to an evening dose (8PM)

TABLE 13-continued

Mean PK Parameters for KAR5585 in Healthy Volunteers Following BID Oral Administration of KAR5585 for 14 Days (Pharmacokinetic Evaluable Population)

Shaded cells without data are where PK sampling regimens relative to time of dose administration did not support calculation of PK parameters (eg, no C24 hr values for BID dosing in Day 1 and Day 7)
Abbreviations: AM, before noon (ante meridiem).
$AUC_{0-12}$, area under the concentration versus time curve from time 0 to 12 hours after dosing, using the trapezoidal rule;
$AUC_{0-24}$, area under the concentration versus time curve from time 0 to 24 hours after dosing, using the trapezoidal rule;
$AUC_{0-t}$, area under the concentration-time curve from time 0 to time of last quantifiable concentration;
BLQ, below the limit of quantitation;
CL/F, apparent oral clearance;
NA, not applicable;
ND, not determined;
NR, not reported;
Param., parameter;
PK, pharmacokinetic;
PM, after noon (post meridiem),
SD, standard deviation;
Stat., statistical;
t½, apparent terminal half-life after oral administration;
$T_{max}$, time of maximum observed concentration;
Vz/F, volume of distribution during the terminal phase

TABLE 14

(Mean PK Parameters for KAR5417 in Healthy Volunteers Following BID Oral Administration of KAR5585 for 14 Days (Pharmacokinetic Evaluable Population))

| Cohort | Day | Period | Stat. Param. | $t_{1/2}$ (hr) | $t_{max}{}^a$ (hr) | $C_{max}$ (ng/mL) | $C_{max}$/D (ng/mL)/mg | $C_{12}$ (ng/mL) | C24 (ng/mL) | $C_{max}$/$C_{12}$ |
|---|---|---|---|---|---|---|---|---|---|---|
| 100 (fasted) Cohort 1 | 1 | $AM^C$ | N | 7 | 9 | 9 | 9 | 8 | | 8 |
| | | | Mean | 3.43 | 3.0 | 121 | 1.21 | 21.3 | | 6.08 |
| | | | SD | 0.751 | 2.0, 6.0 | 83.3 | 0.833 | 10.6 | | 1.32 |
| | | | CV % | 21.9 | NA | 68.9 | 68.9 | 49.5 | | 21.7 |
| | | | Geo. Mean | 3.37 | NA | 101 | 1.01 | 19.5 | | 5.93 |
| | | | Geo. CV % | 21.3 | NA | 70.4 | 70.4 | 45.4 | | 24.8 |
| | 14 | — | N | 9 | 9 | 9 | 9 | 9 | 9 | 9 |
| | | | Mean | 18.8 | 3.0 | 194 | 1.94 | 46.3 | 19.7 | 4.25 |
| | | | SD | 6.67 | 2.0, 4.0 | 87.7 | 0.877 | 21.0 | 8.40 | 0.539 |
| | | | CV % | 35.5 | NA | 45.2 | 45.2 | 45.3 | 42.5 | 12.7 |
| | | | Geo. Mean | 17.6 | NA | 177 | 1.77 | 42.0 | 18.1 | 4.21 |
| | | | Geo. CV % | 42.0 | NA | 49.0 | 49.0 | 51.5 | 47.5 | 14.2 |
| 100 (fed) Cohort 2 | 1 | $AM^c$ | N | 9 | 9 | 9 | 9 | 9 | | 9 |
| | | | Mean | 4.18 | 2.0 | 85.9 | 0.859 | 17.2 | | 5.26 |
| | | | SD | 0.516 | 1.5, 4.0 | 40.4 | 0.404 | 9.54 | | 1.24 |
| | | | CV % | 12.3 | NA | 47.0 | 47.0 | 55.4 | | 23.6 |
| | | | Geo. Mean | 4.16 | NA | 79.2 | 0.792 | 15.4 | | 5.14 |
| | | | Geo. CV % | 12.2 | NA | 42.6 | 42.6 | 49.9 | | 23.3 |
| | | $PM^c$ | N | 7 | 9 | 9 | 9 | 9 | | 9 |
| | | | Mean | 7.00 | 3.0 | 130 | 1.3 | 43.1 | | 3.31 |
| | | | SD | 0.837 | 2.0, 12 | 59.8 | 0.598 | 21.6 | | 1.36 |
| | | | CV % | 12.0 | NA | 46.0 | 46.0 | 50.0 | | 41.0 |
| | | | Geo. Mean | 6.95 | NA | 119 | 1.19 | 39.5 | | 3.01 |
| | | | Geo. CV % | 13.1 | NA | 45.9 | 45.9 | 44.0 | | 53.2 |
| | 7 | $AM^c$ | N | 9 | 9 | 9 | 9 | 9 | | 9 |
| | | | Mean | 5.31 | 3.0 | 168 | 1.68 | 45.1 | | 3.69 |
| | | | SD | 0.975 | 2.0, 4.0 | 60.9 | 0.609 | 9.46 | | 0.837 |
| | | | CV % | 18.4 | NA | 36.2 | 36.2 | 21.0 | | 22.7 |
| | | | Geo. Mean | 5.24 | NA | 160 | 1.60 | 44.3 | | 3.61 |
| | | | Geo. CV % | 18.2 | NA | 33.8 | 33.8 | 20.5 | | 21.4 |
| | | $PM^c$ | N | 4 | 9 | 9 | 9 | 9 | | 9 |
| | | | Mean | 8.10 | 6.0 | 112 | 1.12 | 62.3 | | 1.8 |
| | | | SD | 2.11 | 2.0, 8.0 | 46.4 | 0.464 | 11.5 | | 0.629 |
| | | | CV % | 26.0 | NA | 41.3 | 41.3 | 18.4 | | 34.9 |
| | | | Geo. Mean | 7.91 | NA | 106 | 1.06 | 61.4 | | 1.73 |
| | | | Geo. CV % | 25.6 | NA | 36.0 | 36.0 | 19.0 | | 30.8 |

TABLE 14-continued (Mean PK Parameters for KAR5417 in Healthy Volunteers Following BID Oral Administration of KAR5585 for 14 Days (Pharmacokinetic Evaluable Population))

| Dose/Cohort | Day | Time | Stat | C1 | C2 | C3 | C4 | C5 | C6 | C7 |
|---|---|---|---|---|---|---|---|---|---|---|
| | 14 | AM[c] | N | 8 | 8 | 8 | 8 | 8 | 8 | 8 |
| | | | Mean | 19.6 | 2.0 | 168 | 1.68 | 36.4 | 19.6 | 4.56 |
| | | | SD | 5.30 | 1.5, 4.0 | 67.2 | 0.672 | 9.46 | 4.11 | 1.43 |
| | | | CV % | 27.0 | NA | 40.0 | 40.0 | 26.0 | 20.9 | 31.5 |
| | | | Geo. Mean | 19.0 | NA | 155 | 1.55 | 35.4 | 19.3 | 4.37 |
| | | | Geo. CV % | 29.0 | NA | 47.7 | 47.7 | 25.7 | 21.0 | 31.6 |
| 200 (fed) Cohort 3 | 1 | AM[c] | N | 9 | 9 | 9 | 9 | 9 | | 9 |
| | | | Mean | 4.49 | 3.0 | 357 | 1.79 | 60.7 | | 6.07 |
| | | | SD | 0.977 | 2.0, 4.0 | 142 | 0.709 | 25.1 | | 1.36 |
| | | | CV % | 21.8 | NA | 39.7 | 39.7 | 41.4 | | 22.5 |
| | | | Geo. Mean | 4.41 | NA | 336 | 1.68 | 56.6 | | 5.94 |
| | | | Geo. CV % | 20.1 | NA | 37.4 | 37.4 | 41.0 | | 21.9 |
| | | PM[c] | N | 6 | 9 | 9 | 9 | 9 | | 9 |
| | | | Mean | 6.03 | 4.0 | 322 | 1.61 | 112 | | 3.24 |
| | | | SD | 1.09 | 2.0, 6.0 | 103 | 0.513 | 56.0 | | 1.28 |
| | | | CV % | 18.1 | NA | 31.9 | 31.9 | 50.2 | | 39.4 |
| | | | Geo. Mean | 5.95 | NA | 307 | 1.54 | 102 | | 3.00 |
| | | | Geo. CV % | 18.5 | NA | 33.8 | 33.8 | 43.6 | | 44.6 |
| | 7 | AM[c] | N | 8 | 9 | 9 | 9 | 9 | | 9 |
| | | | Mean | 4.61 | 4.0 | 359 | 1.80 | 93.1 | | 3.83 |
| | | | SD | 0.643 | 2.0, 6.0 | 176 | 0.879 | 38.8 | | 0.393 |
| | | | CV % | 13.9 | NA | 49.0 | 49.0 | 41.7 | | 10.3 |
| | | | Geo. Mean | 4.57 | NA | 332 | 1.66 | 87.2 | | 3.81 |
| | | | Geo. CV % | 14.3 | NA | 40.6 | 40.6 | 38.6 | | 10.6 |
| | | PM[c] | N | 2 | 8 | 8 | 8 | 8 | | 8 |
| | | | Mean | 6.64 | 8.0 | 222 | 1.11 | 145 | | 1.90 |
| | | | SD | NR | 3.0, 12 | 71.3 | 0.356 | 74.3 | | 1.31 |
| | | | CV % | NR | NA | 32.1 | 32.1 | 51.1 | | 68.9 |
| | | | Geo. Mean | 6.48 | NA | 212 | 1.06 | 131 | | 1.62 |
| | | | Geo. CV % | NR | NA | 33.6 | 33.6 | 51.3 | | 61.1 |
| | 14 | AM[c] | N | 8 | 8 | 8 | 8 | 8 | 8 | 8 |
| | | | Mean | 25.0 | 3.0 | 319 | 1.59 | 63.5 | 32.6 | 4.81 |
| | | | SD | 7.06 | 2.0, 6.0 | 175 | 0.877 | 24.9 | 10.7 | 0.991 |
| | | | CV % | 28.3 | NA | 55.1 | 55.1 | 39.3 | 33.0 | 20.6 |
| | | | Geo. Mean | 24.1 | NA | 281 | 1.40 | 59.6 | 31.2 | 4.72 |
| | | | Geo. CV % | 30.2 | NA | 57.2 | 57.2 | 38.9 | 32.0 | 22.5 |
| 400 (fed) Cohort 4 | 1 | AM[c] | N | 9 | 9 | 9 | 9 | 9 | | 9 |
| | | | Mean | 3.80 | 3.0 | 595 | 1.49 | 99.3 | | 5.97 |
| | | | SD | 0.883 | 2.0, 4.0 | 273 | 0.682 | 43.6 | | 0.981 |
| | | | CV % | 23.2 | NA | 45.8 | 45.8 | 44.0 | | 16.4 |
| | | | Geo. Mean | 3.71 | NA | 532 | 1.33 | 90.2 | | 5.90 |
| | | | Geo. CV % | 24.8 | NA | 57.8 | 57.8 | 51.3 | | 16.9 |
| | | PM[c] | N | 5 | 9 | 9 | 9 | 9 | | 9 |
| | | | Mean | 5.31 | 4.0 | 739 | 1.85 | 252 | | 3.05 |
| | | | SD | 0.456 | 3.0, 8.0 | 343 | 0.859 | 76.7 | | 1.29 |
| | | | CV % | 8.6 | NA | 46.4 | 46.4 | 30.4 | | 42.2 |
| | | | Geo. Mean | 5.3 | NA | 670 | 1.68 | 242 | | 2.77 |
| | | | Geo. CV % | 8.6 | NA | 50.6 | 50.6 | 31.8 | | 52.9 |
| | 7 | AM[c] | N | 6 | 9 | 9 | 9 | 9 | | 9 |
| | | | Mean | 3.94 | 4.0 | 1000 | 2.51 | 240 | | 4.36 |
| | | | SD | 0.798 | 3.0, 6.0 | 315 | 0.788 | 103 | | 0.654 |
| | | | CV % | 20.2 | NA | 31.4 | 31.4 | 43.0 | | 15.0 |
| | | | Geo. Mean | 3.89 | NA | 960 | 2.40 | 222 | | 4.32 |
| | | | Geo. CV % | 18.1 | NA | 31.9 | 31.9 | 41.6 | | 15.6 |
| | | PM[c] | N | 2 | 9 | 9 | 9 | 9 | | 9 |
| | | | Mean | 5.10 | 6.0 | 608 | 1.52 | 396 | | 1.80 |
| | | | SD | NR | 3.0, 12 | 201 | 0.503 | 198 | | 0.961 |
| | | | CV % | NR | NA | 33.1 | 33.1 | 50.0 | | 53.4 |
| | | | Geo. | 5.08 | NA | 574 | 1.44 | 356 | | 1.61 |

TABLE 14-continued (Mean PK Parameters for KAR5417 in Healthy Volunteers Following BID Oral Administration of KAR5585 for 14 Days (Pharmacokinetic Evaluable Population))

|  |  |  |  |  |  |  |  |  |  |
|---|---|---|---|---|---|---|---|---|---|
|  |  | Mean Geo. CV % | NR | NA | 38.5 | 38.5 | 51.3 |  | 50.1 |
|  | 14 | AM[c] | N | 9 | 9 | 9 | 9 | 9 | 9 | 9 |
|  |  |  | Mean | 30.6 | 3.0 | 749 | 1.87 | 149 | 76.6 | 5.20 |
|  |  |  | SD | 3.84 | 2.0, 3.0 | 230 | 0.574 | 56.8 | 25.5 | 1.08 |
|  |  |  | CV % | 12.5 | NA | 30.6 | 30.6 | 38.1 | 33.3 | 20.8 |
|  |  |  | Geo. Mean | 30.4 | NA | 717 | 1.79 | 140 | 73.3 | 5.11 |
|  |  |  | Geo. CV % | 12.5 | NA | 32.8 | 32.8 | 37.4 | 31.6 | 20.5 |

| Cohort | Day | Period | Stat. Param. | AUC$_{0-12}$[b] (hr*ng/mL) | AUC$_{0-24}$ (hr*ng/mL) | AU$_{0-24}$/D (hr*ng/mL)/mg | AUC$_{0-\infty}$ (hr*ng/mL) | R$_{Cmax}$[d] | R$_{AUC0-12}$[d] |
|---|---|---|---|---|---|---|---|---|---|
| 100 (fasted) Cohort 1 | 1 | AM[C] | N | 8 |  |  | 7 |  |  |
|  |  |  | Mean | 741 |  |  | 876 |  |  |
|  |  |  | SD | 491 |  |  | 545 |  |  |
|  |  |  | CV % | 66.3 |  |  | 62.2 |  |  |
|  |  |  | Geo. Mean | 643 |  |  | 769 |  |  |
|  |  |  | Geo. CV % | 56.8 |  |  | 55.9 |  |  |
|  | 14 | — | N | 9 | 9 | 9 | 9 | 9 | 8 |
|  |  |  | Mean | 1280 | 1650 | 16.5 | 2220 | 2.56 | 1.83 |
|  |  |  | SD | 620 | 782 | 7.82 | 1130 | 2.96 | 0.940 |
|  |  |  | CV % | 48.4 | 47.3 | 47.3 | 50.9 | 116 | 51.4 |
|  |  |  | Geo. Mean | 1150 | 1490 | 14.9 | 1960 | 1.75 | 1.64 |
|  |  |  | Geo. CV % | 53.0 | 52.1 | 52.1 | 59.2 | 101 | 52.5 |
| 100 (fed) Cohort 2 | 1 | AM[c] | N | 9 |  |  | 9 |  |  |
|  |  |  | Mean | 470 |  |  | 564 |  |  |
|  |  |  | SD | 247 |  |  | 288 |  |  |
|  |  |  | CV % | 52.5 |  |  | 51.0 |  |  |
|  |  |  | Geo. Mean | 428 |  |  | 516 |  |  |
|  |  |  | Geo. CV % | 45.1 |  |  | 44.0 |  |  |
|  |  | PM[c] | N | 9 | 9 | 9 | 7 |  |  |
|  |  |  | Mean | 748 | 1220 | 6.09 | 1140 |  |  |
|  |  |  | SD | 251 | 454 | 2.27 | 394 |  |  |
|  |  |  | CV % | 33.5 | 37.3 | 37.3 | 34.5 |  |  |
|  |  |  | Geo. Mean | 714 | 1160 | 5.78 | 1090 |  |  |
|  |  |  | Geo. CV % | 32.6 | 33.8 | 33.8 | 35.7 |  |  |
|  | 7 | AM[c] | N | 9 |  |  | 9 | 9 | 9 |
|  |  |  | Mean | 1080 |  |  | 1410 | 2.07 | 2.57 |
|  |  |  | SD | 296 |  |  | 300 | 0.502 | 0.8 |
|  |  |  | CV % | 27.4 |  |  | 21.3 | 24.2 | 31.2 |
|  |  |  | Geo. Mean | 1050 |  |  | 1380 | 2.02 | 2.45 |
|  |  |  | Geo. CV % | 26.9 |  |  | 20.5 | 24.6 | 34.0 |
|  |  | PM[c] | N | 9 | 9 | 9 | 4 | 9 | 9 |
|  |  |  | Mean | 902 | 1990 | 9.93 | 1730 | 1.43 | 2.19 |
|  |  |  | SD | 254 | 533 | 2.67 | 337 | 0.552 | 0.806 |
|  |  |  | CV % | 28.2 | 26.8 | 26.8 | 19.5 | 38.6 | 36.8 |
|  |  |  | Geo. Mean | 875 | 1930 | 9.64 | 1700 | 1.34 | 2.04 |
|  |  |  | Geo. CV % | 25.9 | 25.8 | 25.8 | 19.2 | 41.8 | 43.0 |
|  | 14 | AM[c] | N | 8 | 8 |  | 8 | 8 | 8 |
|  |  |  | Mean | 943 | 1270 |  | 1830 | 1.98 | 2.23 |
|  |  |  | SD | 296 | 366 |  | 455 | 0.650 | 0.818 |
|  |  |  | CV % | 31.4 | 28.8 |  | 24.9 | 32.8 | 36.7 |
|  |  |  | Geo. Mean | 900 | 1220 |  | 1780 | 1.90 | 2.09 |
|  |  |  | Geo. CV % | 34.4 | 30.9 |  | 25.7 | 31.1 | 40.2 |
| 200 (fed) Cohort 3 | 1 | AM[c] | N | 9 |  |  | 9 |  |  |
|  |  |  | Mean | 1700 |  |  | 2090 |  |  |
|  |  |  | SD | 605 |  |  | 785 |  |  |
|  |  |  | CV % | 35.5 |  |  | 37.5 |  |  |
|  |  |  | Geo. | 1620 |  |  | 1980 |  |  |

TABLE 14-continued (Mean PK Parameters for KAR5417 in Healthy Volunteers Following BID Oral Administration of KAR5585 for 14 Days (Pharmacokinetic Evaluable Population))

| Dose (fed/fasted) Cohort | Day | AM/PM[c] | Statistic | | | | | | |
|---|---|---|---|---|---|---|---|---|---|
| | | | Geo. Mean | 35.0 | | | 36.3 | | |
| | | | CV % | | | | | | |
| | | PM[c] | N | 9 | 9 | 9 | 6 | | |
| | | | Mean | 2000 | 3700 | 9.26 | 2720 | | |
| | | | SD | 680 | 1260 | 3.16 | 775 | | |
| | | | CV % | 34.0 | 34.1 | 34.1 | 28.5 | | |
| | | | Geo. Mean | 1910 | 3540 | 8.85 | 2640 | | |
| | | | Geo. CV % | 31.5 | 31.9 | 31.9 | 27.9 | | |
| | 7 | AM[c] | N | 9 | | | 8 | 9 | 9 |
| | | | Mean | 2300 | | | 2800 | 1.00 | 1.34 |
| | | | SD | 1010 | | | 1280 | 0.176 | 0.198 |
| | | | CV % | 44.0 | | | 45.8 | 17.5 | 14.8 |
| | | | Geo. Mean | 2150 | | | 2610 | 0.989 | 1.33 |
| | | | Geo. CV % | 38.5 | | | 39.4 | 18.5 | 14.6 |
| | | PM[c] | N | 8 | 8 | 8 | 2 | 8 | 8 |
| | | | Mean | 1540 | 3810 | 9.52 | 2280 | 0.711 | 0.984 |
| | | | SD | 413 | 1440 | 3.60 | NR | 0.376 | 0.276 |
| | | | CV % | 26.9 | 37.8 | 37.8 | NR | 52.9 | 28.0 |
| | | | Geo. Mean | 1490 | 3620 | 9.05 | 2270 | 0.645 | 0.955 |
| | | | Geo. CV % | 25.8 | 33.5 | 33.5 | NR | 46.5 | 26.1 |
| | 14 | AM[c] | N | 8 | 8 | | 8 | 8 | 8 |
| | | | Mean | 1820 | 2380 | | 3480 | 0.901 | 1.09 |
| | | | SD | 887 | 1090 | | 1430 | 0.304 | 0.235 |
| | | | CV % | 48.7 | 45.7 | | 41.1 | 33.7 | 21.5 |
| | | | Geo. Mean | 1670 | 2200 | | 3250 | 0.854 | 1.07 |
| | | | Geo. CV % | 45.7 | 43.1 | | 41.1 | 36.8 | 24.0 |
| 400 (fed) Cohort 4 | 1 | AM[c] | N | 9 | | | 9 | | |
| | | | Mean | 3280 | | | 3780 | | |
| | | | SD | 1550 | | | 1690 | | |
| | | | CV % | 47.4 | | | 44.8 | | |
| | | | Geo. Mean | 2920 | | | 3400 | | |
| | | | Geo. CV % | 58.5 | | | 54.6 | | |
| | | PM[c] | N | 9 | 9 | 9 | 5 | | |
| | | | Mean | 4590 | 7870 | 9.83 | 7090 | | |
| | | | SD | 1550 | 2830 | 3.53 | 1970 | | |
| | | | CV % | 33.7 | 35.9 | 35.9 | 27.8 | | |
| | | | Geo. Mean | 4340 | 7430 | 9.28 | 6860 | | |
| | | | Geo. CV % | 37.1 | 37.3 | 37.3 | 30.0 | | |
| | 7 | AM[c] | N | 9 | | | 6 | 9 | 9 |
| | | | Mean | 6600 | | | 7840 | 2.00 | 2.38 |
| | | | SD | 2340 | | | 2650 | 0.991 | 1.17 |
| | | | CV % | 35.4 | | | 33.9 | 49.5 | 49.1 |
| | | | Geo. Mean | 6250 | | | 7480 | 1.81 | 2.15 |
| | | | Geo. CV % | 35.7 | | | 34.6 | 49.5 | 51.3 |
| | | PM[c] | N | 9 | 9 | 9 | 2 | 9 | 9 |
| | | | Mean | 4610 | 11200 | 14.0 | 6520 | 1.18 | 1.63 |
| | | | SD | 1590 | 3890 | 4.86 | NR | 0.498 | 0.737 |
| | | | CV % | 34.5 | 34.7 | 34.7 | NR | 42.4 | 45.2 |
| | | | Geo. Mean | 4360 | 10600 | 13.3 | 6450 | 1.08 | 1.50 |
| | | | Geo. CV % | 36.9 | 35.8 | 35.8 | NR | 46.9 | 45.4 |

TABLE 15

(Accumulation Ratios for KAR5417 and KAR5585 in Healthy Volunteers Following BID Oral Administration of KAR5585 for 14 Days (Pharmacokinetic Evaluable Population))

| Dose (mg/feeding status) | Day | Post AM or PM Dose | Stat. Param. | KAR5585 $R_{Cmax}$ | KAR5585 $R_{AUC0-12}$ | KAR5417 $R_{Cmax}$ | KAR5417 $R_{AUC0-12}$ |
|---|---|---|---|---|---|---|---|
| 100/Fasted Cohort 1 | 14 | AM | N | 7 | 4 | 9 | 8 |
| | | | Mean | 1.30 | 1.85 | 2.56 | 1.83 |
| | | | SD | 0.592 | 0.870 | 2.96 | 0.940 |
| | | | CV % | 45.5 | 47.0 | 116 | 51.4 |
| | | | Geo. Mean | 1.20 | 1.70 | 1.75 | 1.64 |
| | | | Geo. CV % | 43.0 | 52.1 | 101 | 52.5 |
| 100/Fed Cohort 2 | 7 | AM | N | 9 | 3 | 9 | 9 |
| | | | Mean | 1.74 | 3.32 | 2.07 | 2.57 |
| | | | SD | 0.469 | 1.10 | 0.502 | 0.8 |
| | | | CV % | 26.9 | 33.2 | 24.2 | 31.2 |
| | | | Geo. Mean | 1.69 | 3.18 | 2.02 | 2.45 |
| | | | Geo. CV % | 28.7 | 38.0 | 24.6 | 34.0 |
| | 7 | PM | N | 9 | 3 | 9 | 9 |
| | | | Mean | 1.66 | 3.11 | 1.43 | 2.19 |
| | | | SD | 1.03 | 2.18 | 0.552 | 0.806 |
| | | | CV % | 62.1 | 70.1 | 38.6 | 36.8 |
| | | | Geo. Mean | 1.46 | 2.68 | 1.34 | 2.04 |
| | | | Geo. CV % | 54.5 | 71.6 | 41.8 | 43.0 |
| | 14 | AM | N | 8 | 3 | 8 | 8 |
| | | | Mean | 1.68 | 2.75 | 1.98 | 2.23 |
| | | | SD | 0.465 | 0.938 | 0.650 | 0.818 |
| | | | CV % | 27.7 | 34.1 | 32.8 | 36.7 |
| | | | Geo. Mean | 1.62 | 2.62 | 1.90 | 2.09 |
| | | | Geo. CV % | 30.2 | 40.8 | 31.1 | 40.2 |
| 200/Fed Cohort 3 | 7 | AM | N | 9 | 9 | 9 | 9 |
| | | | Mean | 0.589 | 0.933 | 1.00 | 1.34 |
| | | | SD | 0.175 | 0.328 | 0.176 | 0.198 |
| | | | CV % | 29.8 | 35.2 | 17.5 | 14.8 |
| | | | Geo. Mean | 0.565 | 0.892 | 0.989 | 1.33 |
| | | | Geo. CV % | 31.1 | 30.6 | 18.5 | 14.6 |
| | 7 | PM | N | 8 | 8 | 8 | 8 |
| | | | Mean | 0.597 | 0.895 | 0.711 | 0.984 |
| | | | SD | 0.379 | 0.304 | 0.376 | 0.276 |
| | | | CV % | 63.4 | 34.0 | 52.9 | 28.0 |
| | | | Geo. Mean | 0.515 | 0.854 | 0.645 | 0.955 |
| | | | Geo. CV % | 59.7 | 33.3 | 46.5 | 26.1 |
| | 14 | AM | N | 8 | 7 | 8 | 8 |
| | | | Mean | 0.643 | 0.761 | 0.901 | 1.09 |
| | | | SD | 0.323 | 0.230 | 0.304 | 0.235 |
| | | | CV % | 50.2 | 30.2 | 33.7 | 21.5 |
| | | | Geo. Mean | 0.573 | 0.730 | 0.854 | 1.07 |
| | | | Geo. CV % | 56.1 | 32.6 | 36.8 | 24.0 |
| 400/Fed Cohort 4 | 7 | AM | N | 9 | 9 | 9 | 9 |
| | | | Mean | 1.32 | 2.01 | 2.00 | 2.38 |
| | | | SD | 0.627 | 0.872 | 0.991 | 1.17 |
| | | | CV % | 47.4 | 43.3 | 49.5 | 49.1 |
| | | | Geo. Mean | 1.23 | 1.87 | 1.81 | 2.15 |
| | | | Geo. CV % | 37.1 | 40.8 | 49.5 | 51.3 |
| | 7 | PM | N | 9 | 9 | 9 | 9 |
| | | | Mean | 0.971 | 1.71 | 1.18 | 1.63 |
| | | | SD | 0.444 | 0.810 | 0.498 | 0.737 |
| | | | CV % | 45.7 | 47.3 | 42.4 | 45.2 |
| | | | Geo. Mean | 0.857 | 1.56 | 1.08 | 1.50 |
| | | | Geo. CV % | 63.6 | 48.1 | 46.9 | 45.4 |
| | 14 | AM | N | 9 | 9 | 9 | 9 |
| | | | Mean | 1.28 | 1.60 | 1.54 | 1.65 |
| | | | SD | 0.647 | 0.938 | 0.967 | 1.06 |
| | | | CV % | 50.4 | 58.7 | 63.0 | 63.9 |
| | | | Geo. Mean | 1.15 | 1.42 | 1.35 | 1.43 |
| | | | Geo. CV % | 52.5 | 52.2 | 54.0 | 59.6 |

Abbreviations:
AM, before noon (ante meridiem);
BID, twice daily;
Geo., geometric;
hr, hour;
N, number;
PM, after noon (post meridiem);
$R_{AUC0-12}$, accumulation ratio for $AUC_{0-12}$;
$R_{Cmax}$, accumulation ratio for $C_{max}$;
SD, standard deviation;

TABLE 15-continued (Accumulation Ratios for KAR5417 and KAR5585 in Healthy Volunteers Following BID Oral Administration of KAR5585 for 14 Days (Pharmacokinetic Evaluable Population))

| Dose (mg/feeding status) | Post AM or PM Day | Stat. Dose | Param. | KAR5585 $R_{Cmax}$ | $R_{AUC0-12}$ | KAR5417 $R_{Cmax}$ | $R_{AUC0-12}$ |
|---|---|---|---|---|---|---|---|

$t_{1/2}$, apparent terminal half-life after oral administration.

Dose Proportionality Assessment of KAR5585 and KAR5417:

Scatter plots of individual plasma KAR5585 and KAR5417 Day 1 and Day 14 $C_{max}$ KAR5585 dose are presented in FIGS. 14a and 14b and FIGS. 15a and 15b, respectively. Scatter plots of individual plasma KAR5585 and KAR5417 Day 1 and Day 14 $AUC_{0-12}$ KAR5585 dose are presented in FIGS. 16a and 16b and FIGS. 17a and 17b. The dose proportionality assessment of plasma KAR5585 and KAR5417 PK parameters are summarized in Table 16. Dose proportionality was assessed for KAR5585 and KAR5417 after repeat-dose, twice-daily administration of KAR5585 using the power model. From plots of exposure (i.e., $C_{max}$, $AUC_{0-12}$ and/or $AUC_{0-inf}$) versus dose, increases in exposure were deemed dose proportional if the 95% confidence intervals (CIs) for the slope (13 included unity (e.g., 1.0). The CIs presented in Table 16 indicate that $C_{max}$, $AUC_{0-12}$ and/or $AUC_{0-inf}$ for both KAR5585 and KAR5417 increase in dose proportional manner from 100-400 mg of KAR5585 (Part 2, Cohorts 2-4) in the fed state.

TABLE 16

(Summary of Dose Proportionality Analysis of Plasma KAR5417 and KAR5585 Pharmacokinetic Parameters $AUC_{0-12}$, $AUC_{0-inf}$, and $C_{max}$ Following 100 to 400 mg of KAR5585 Administered as Repeat Oral Doses under Fed Conditions (Pharmacokinetic Evaluable Population))

| Parameter | PK Day (AM) | Analyte | Effect | Estimate | Degrees of Freedom | Standard Error | 95% Confidence Interval |
|---|---|---|---|---|---|---|---|
| $AUC_{0-12}$ | 1 | KAR5417 | Intercept | 0.828 | 25 | NC | NC |
| | | | Slope (β) | 1.38 | 25 | 0.161 | 1.05-1.71 |
| | | KAR5585 | Intercept | 0.969 | 20 | NC | NC |
| | | | Slope (β) | 0.964 | 20 | 0.245 | 0.453-1.47 |
| | 7 | KAR5417 | Intercept | 2.63 | 25 | NC | NC |
| | | | Slope (β) | 1.29 | 25 | 0.114 | 1.05-1.52 |
| | | KAR5585 | Intercept | 1.51 | 24 | NC | NC |
| | | | Slope (β) | 0.952 | 24 | 0.0950 | 0.756-1.15 |
| | 14 | KAR5417 | Intercept | 5.18 | 23 | NC | NC |
| | | | Slope (β) | 1.11 | 23 | 0.127 | 0.846-1.37 |
| | | KAR5585 | Intercept | 2.37 | 21 | NC | NC |
| | | | Slope (β) | 0.832 | 21 | 0.0951 | 0.634-1.03 |
| $AUC_{0-inf}$ | 1 | KAR5417 | Intercept | 1.12 | 25 | NC | NC |
| | | | Slope (β) | 1.36 | 25 | 0.159 | 1.03-1.69 |
| | | KAR5585 | Intercept | 0.817 | 20 | NC | NC |
| | | | Slope (β) | 1.01 | 20 | 0.255 | 0.474-1.54 |
| $C_{max}$ | 1 | KAR5417 | Intercept | 0.167 | 25 | NC | NC |
| | | | Slope (β) | 1.37 | 25 | 0.169 | 1.03-1.72 |
| | | KAR5585 | Intercept | 0.198 | 25 | NC | NC |
| | | | Slope (β) | 1.03 | 25 | 0.193 | 0.636-1.43 |
| | 7 | KAR5417 | Intercept | 0.393 | 25 | NC | NC |
| | | | Slope (β) | 1.29 | 25 | 0.118 | 1.05-1.54 |
| | | KAR5585 | Intercept | 0.688 | 25 | NC | NC |
| | | | Slope β) | 0.809 | 25 | 0.121 | 0.561-1.06 |
| | 14 | KAR5417 | Intercept | 0.877 | 23 | NC | NC |
| | | | Slope (β) | 1.11 | 23 | 0.153 | 0.794-1.43 |
| | | KAR5585 | Intercept | 0.705 | 23 | NC | NC |
| | | | Slope (β) | 0.794 | 23 | 0.139 | 0.508-1.08 |

Abbreviations:
AM, before noon (ante meridiem);
$AUC_{0-12}$, area under the concentration versus time curve from time 0 to 12 hours after dosing, using the trapezoidal rule;
$AUC_{0-24}$, area under the concentration versus time curve from time 0 to 24 hours after dosing, using the trapezoidal rule;
$AUC_{0-inf}$, area under the concentration versus time curve from time 0 extrapolated to infinity;
NC, not calculated;
PK, pharmacokinetic.

Discussion of Pharmacokinetics Results

Following KAR5585 administration, KAR5585 was rapidly absorbed. For doses of 100, 200 and 400 mg KAR5585, Part 2, Cohorts 2-4 (fed state), the median time to peak plasma concentrations of KAR5585 ranged from 0.75-4 hours, 1.5 to 6 hours, and 1.5 to 6 hours, respectively, on all dosing days and times. There was some evidence for delayed absorption of KAR5585 on Day 7 for the evening dose, where the median time to peak plasma concentrations of KAR5585 were 4 hours, 6 hours, and 6 hours, for the 100, 200 and 400 mg doses, respectively. The Day 7 PM $t_{max}$ values were on the upper end of the $t_{max}$ values determined in Day 1, Day 7 and Day 14. This was not observed on Day 1.

Peak plasma KAR5585 concentrations, as measured by mean $C_{max}$, increased in a dose proportional manner from 100-400 mg (Part 2, Cohort 2-4, fed state). Mean $C_{max}$ values increased 4.4-fold over the 4-fold increase in dose between the 100 mg dose (Cohort 2) and the 400 mg dose (Cohort 4) on Day 1. Mean $C_{max}$ values increased 3.0-fold over the 4-fold increase in dose between the 100 mg dose (Part 2, Cohort 2) and the 400 mg dose (Part 2, Cohort 4) on Day 14.

Systemic exposure to KAR5585, as measured by mean $AUC_{0-12}$ and $AUC_{0-24}$, appeared to increase in a dose-proportional manner between the 100 and 400 mg dose levels, with a 5.1-fold and 3.6-fold increase in mean $AUC_{0-12}$ and mean $AUC_{0-24}$ estimates, respectively, for a 4-fold increase in dose between the 100 mg dose (Part 2, Cohort 2) and the 400 mg dose (Part 2, Cohort 4) on Day 1. Mean $AUC_{0-12}$ and mean $AUC_{0-24}$ estimates, increased 3.1-fold and 3.63-fold respectively, for a 4-fold increase in dose between the 100 mg dose (Part 2, Cohort 2) and the 400 mg dose (Part 2, Cohort 4) on Day 14.

The mean apparent elimination half-life of KAR5585 increased with increasing dose levels studied, and the mean values were 2.73, 4.08 and 6.45 hrs on Day 14 after oral administration of repeat dose twice-daily administration of 100, 200 and 400 mg of KAR5585 (Part 2, Cohort 2-4, fed state), respectively. The half-life of KAR5585 was 2.49 hrs on Day 14 after oral administration of repeat dose twice-daily administration of 100 mg in the fasted state, and was comparable to the half-life in the fed state (2.73 hrs) for the 100 mg dose.

Peak plasma KAR5417 concentrations, as measured by mean $C_{max}$, appeared to increase in a greater that dose proportional manner from 100-400 mg (Part 2, Cohort 2-4, fed state). Mean $C_{max}$ values increased 6.9-fold over the 4-fold increase in dose between the 100 mg dose (Cohort 2) and the 400 mg dose (Cohort 4) on Day 1. Day 14 mean $C_{max}$ values increased in an approximately dose proportional manner with an ~4.5-fold increase in $C_{max}$ over the 4-fold increase in dose between the 100 mg dose (Part 2, Cohort 2) and the 400 mg dose (Part 2, Cohort 4).

Mean extent of systemic exposure to KAR5417, as measured by mean $AUC_{0-12}$ and $AUC_{0-24}$, appeared to increase in a greater than dose-proportional manner between the 100 and 400 mg dose levels, with a 7.0-fold and 6.45-fold increase in mean $AUC_{0-12}$ and mean $AUC_{0-24}$ estimates, respectively, for a 4-fold increase in dose between the 100 mg dose (Part 2, Cohort 2) and the 400 mg dose (Part 2, Cohort 4) on Day 1. Day 14 mean $AUC_{0-12}$ and mean $AUC_{0-24}$ estimates, increased 4.6-fold and 4.45-fold respectively, for a 4-fold increase in dose between the 100 mg dose (Part 1, Cohort 2) and the 400 mg dose (Part 2, Cohort 4).

Overall, the mean extent of systemic exposure to KAR5417, as measured by mean $AUC_{0-12}$ and $AUC_{0-24}$, appeared to be comparable under fasted conditions (Part 2, Cohort 1; Day 1 $AUC_{0-12}$=741 hr*ng/mL; Day 14 $AUC_{0-24}$=1650 hr*ng/mL,) relative to fed conditions (Part 2, Cohort 2; Day 1 $AUC_{0-12}$=470 hr*ng/mL; Day 14 $AUC_{0-24}$=1220 hr*ng/mL,). This observation is in contrast to the food effect comparison in Part 1, Cohort 3A and 3B (400 mg KAR5585). In Part 1, a high fat, high calorie meal resulted in $AUC_{0-inf}$ of KAR5417 that was approximately 1.8-fold higher following drug administration of KAR5585 400 mg under fed conditions ($AUC_{0-inf}$=6710 ng·hr/mL) relative to fasting conditions ($AUC_{0-inf}$=3650 ng·hr/mL).

Steady-state plasma levels of KAR5417 were achieved by Day 7 as assessed by comparison of Day 7 and Day 14 $AUC_{0-12}$ and $C_{12hr}$ values following twice daily oral administration of KAR5585 for 14-days. Accumulation ratios for KAR5417 compared $R_{Cmax}$ and $R_{AUC0-12}$ for Day 7/Day 1 and Day 14/Day 1, and verified that steady-state was achieved by Day 7. The $R_{AUC0-12}$ values for KAR5417 ranged from 2.19-2.57, 1.09-1.34 and 1.65-2.38 for the 100, 200 and 400 mg doses of KAR5585, respectively, suggesting that the PK of KAR5417 was independent of time, and steady-state was achieved on Day 7 following repeated twice-daily administration for 14-days.

Pharmacokinetics Conclusions

KAR5585 is a prodrug for the active TPH1 inhibitor KAR5417. Following KAR5585 administration, KAR5585 was rapidly absorbed and converted to KAR5417.

Peak plasma KAR5417 concentrations, as measured by mean $C_{max}$, appeared to increase in a greater that dose proportional manner from 100-400 mg (Part 2, Cohort 2-4, fed state). Mean $C_{max}$ values increased 6.9-fold over the 4-fold increase in dose between the 100 mg dose (Cohort 2) and the 400 mg dose (Cohort 4) on Day 1. On Day 14, mean $C_{max}$ values increased in an approximately dose proportional manner with an ~4.5-fold increase in $C_{max}$ over the 4-fold increase in dose between the 100 mg dose (Part 2, Cohort 2) and the 400 mg dose (Part 2, Cohort 4). For doses of 100, 200 and 400 mg KAR5585, Part 2, Cohorts 2-4 (fed state), the median time to peak plasma concentrations of KAR5417 ranged from 2 to 6 hours, 3 to 8 hours, and 3 to 6 hrs.

Mean extent of systemic exposure to KAR5417, as measured by mean $AUC_{0-12}$ and $AUC_{0-24}$, appeared to increase in a greater than dose-proportional manner between the 100 and 400 mg dose levels, with a 7.0-fold and 6.45-fold increase in mean $AUC_{0-12}$ and mean $AUC_{0-24}$ estimates, respectively, for a 4-fold increase in dose between the 100 mg dose (Part 2, Cohort 2) and the 400 mg dose (Part 2, Cohort 4) on Day 1. Day 14, mean $AUC_{0-12}$ and mean $AUC_{0-24}$ estimates, increased 4.6-fold and 4.45-fold respectively, for a 4-fold increase in dose between the 100 mg dose (Part 1, Cohort 2) and the 400 mg dose (Part 2, Cohort 4).

Overall, the mean extent of systemic exposure to KAR5417, as measured by mean $AUC_{0-12}$ and $AUC_{0-24}$, appeared comparable under fasted conditions (Part 2, Cohort 1; Day 1 $AUC_{0-12}$=741 hr*ng/mL; Day 14 $AUC_{0-24}$=1650 hr*ng/mL,) relative to fed conditions (Part 2, Cohort 2; Day 1 $AUC_{0-12}$=470 hr*ng/mL; Day 14 $AUC_{0-24}$=1220 hr*ng/mL,). This observation is in contrast to the food effect comparison in Part 1, Cohort 3A and 3B (400 mg KAR5585). In Part 1, a high fat, high calorie meal resulted in $AUC_{0-inf}$ of KAR5417 that was approximately 2-fold higher following drug administration of KAR5585 400 mg under fed conditions ($AUC_{0-inf}$=6710 ng·hr/mL) relative to fasting conditions ($AUC_{0-inf}$=3650 ng·hr/mL).

The mean apparent elimination half-life of KAR5417 was 19.6, 25.0 and 30.6 hrs on Day 14 after oral administration of repeat dose twice-daily administration of 100, 200 and 400 mg of KAR5585 (Part 2, Cohort 2-4, fed state). The elimination half-life (30.6 hrs) of KAR5417 on repeat dose administration of 400 mg doses of KAR5585, was similar to the elimination half-life of KAR5417 (20.5 hrs) following single-dose administration of 400 mg KAR5585 (Part 1 Cohort 3B).

KAR5417 plasma levels achieved steady-state exposure by Day 7 as assessed by comparison of Day 7 and Day 14 $AUC_{0-12}$ and $C_{12hr}$ values following twice daily administration of KAR5585 for 14-days. Accumulation ratios for KAR5417 compared $R_{Cmax}$ and $R_{AUC0-12}$ for Day 7/Day 1 and Day 14/Day 1. The $R_{AUC0-12}$ values for KAR5417 ranged from 2.19-2.57, 1.09-1.34 and 1.65-2.38 for the 100, 200 and 400 mg doses of KAR5585 suggesting that the PK of KAR5417 was independent of time and steady-state was achieved on Day 7 following repeated, twice-daily administration for 14-days.

Biomarker Evaluation:

Biomarker evaluations were carried out in subjects dosed with KAR5585 or placebo.

The biomarker portion of the study was conducted in Part 2 MAD using the Biomarker Population. The biomarkers evaluated were serum 5-HT and plasma 5-HIAA, as well as urine 5-HIAA/24 hours (as measured, adjusted, estimated, and per gram creatinine). Urinary 5-HIAA was determined by a validated (21 C.F.R. 58, GLP-compliant) method using liquid chromatographic separation and tandem mass spectrometry detection.

The Biomarker Population consisted of all subjects with evaluable baseline (Day 1 predose) and at least one postdose (Day 7 or Day 14) biomarker measurements.

A total of 48 subjects received study drug according to the protocol (Table 22). Two plasma 5 HIAA values were excluded from analyses because Day 7 assessments were lacking. These were values for Subject 001-M036 in the KAR5585 200 mg fed Cohort and Subject 001-M001 in the KAR5585 100 mg fasting Cohort. Tables and figures missing a Day 7 value for one or both these subjects are marked with an "s". Values excluded were identified based on statistical criteria and clinical sensibility.

Baseline Characteristics:

Baseline characteristics are presented in Table 23. Baseline levels of the biomarkers serum 5-HT, plasma-5HIAA, the 5-HIAA measured in urine during 24 hours, without adjustment for daily variations in creatinine excretion (measured urine 5-HIAA), the 5-HIAA measured in urine during 24 hours, adjusted for the mean 24-hour creatinine excretion on Days 1, 7, and 14 (adjusted urine 5-HIAA), estimated urine 5-HIAA, and urine 5-HIAA were similar among the 5 treatment groups (placebo, KAR5585 100 mg fasting, KAR5585 100 mg fed, KAR5585 200 mg fed, and KAR5585 400 mg fed).

Analysis of Biomarkers: Biomarker Results and Tabulations of Individual Subject Data:

Biomarker data were analyzed for each KAR5585 dose separately, for all KAR5585 doses pooled, and for all placebo subjects pooled.

Biomarker analyses were performed for:

Serum 5-HT

Plasma 5-HIAA

Urine 5-HIAA/24 hours (as measured, adjusted, estimated, and per gram creatinine)

Analyses of biomarker changes and biomarker changes with respect to PK parameters were performed. Linear mixed-effect modeling for combined Day 7 and Day 14 biomarker measurements versus corresponding PK parameters to account for the repeated measures for the same subject had been planned but it was not performed because the relationships between Day 7 and Day 14 versus PK parameters were not consistent with each other.

Primary Biomarker Endpoint: Change in Plasma 5 Hydroxyindoleacetic Acid from Day 1 to Day 14:

Dosing with KAR5585 reduced plasma 5-HIAA concentration. Mean percent change in plasma 5-HIAA was −56.67 from Day 1 to Day 7 and −53.33 from Day 1 to Day 14 in subjects randomized to KAR5575 400 mg under fed conditions. Mean percent change at Day 7 was +19.79 and at Day 14 was +20.12 in subjects randomized to placebo. Mean difference of both absolute and percent changes from Day 1 to Day 14 in plasma 5-HIAA concentration was statistically significant in favor of KAR5585 compared to placebo in each dose group and for all doses combined at Day 14 (Table 17).

TABLE 17

(Differences of Changes from Day 1 Predose between KAR5585 and Placebo of Plasma 5-HIAA (ng/mL) by Cohort - Part 2 MAD Biomarker Population)

| | | Mean Difference of Changes from Day 1 between KAR5585 and Placebo | | | |
|---|---|---|---|---|---|
| | | Absolute Change from Day 1 | | % Change from Day 1 | |
| Dose Level/Time | | Estimate (95% CI) | P Value | Estimate (95% CI) | P Value |
| 100 mg Fasting | Predose Day 7 | 0.33 (−10.74, 11.41) | 0.9531 | 23.67 (−73.11, 120.45) | 0.6330 |
| | Predose Day 14 | −5.92 (−9.42, −2.41) | 0.0015 | −48.83 (−67.43, −30.22) | <.0001 |
| 100 mg Fed | Predose Day 7 | −4.56 (−15.63, 6.52) | 0.4226 | −48.56 (−145.34, 48.21) | 0.3284 |
| | Predose Day 14 | −4.50 (−8.13, −0.87) | 0.0175 | −52.70 (−71.95, −33.45) | <.0001 |
| 200 mg Fed | Predose Day 7 | 1.22 (−9.85, 12.30) | 0.8293 | 12.06 (−84.72, 108.83) | 0.8077 |
| | Predose Day 14 | −5.25 (−8.88, −1.62) | 0.0059 | −52.46 (−71.71, −33.20) | <.0001 |
| 400 mg Fed | Predose Day 7 | −11.44 (−22.52, −0.37) | 0.0463 | −76.47 (−173.24, 20.31) | 0.1255 |
| | Predose Day 14 | −10.69 (−14.20, −7.19) | <.0001 | −73.45 (−92.05, −54.85) | <.0001 |
| All Doses | Predose Day 7 | −3.61 | 0.4005 | −22.33 | 0.5515 |

TABLE 17-continued (Differences of Changes from Day 1 Predose between KAR5585 and Placebo of Plasma 5-HIAA (ng/mL) by Cohort - Part 2 MAD Biomarker Population)

| | Mean Difference of Changes from Day 1 between KAR5585 and Placebo | | | |
|---|---|---|---|---|
| | Absolute Change from Day 1 | | % Change from Day 1 | |
| Dose Level/Time | Estimate (95% CI) | P Value | Estimate (95% CI) | P Value |
| Predose Day 14 | (−11.98, 4.76) −6.69 (−9.36, −4.02) | <.0001 | (−95.48, 50.83) −57.11 (−71.27, −42.95) | <.0001 |

Abbreviations:
5-HIAA, 5-hydroxyindoleacetic acid;
CI, confidence interval;
MAD, multiple ascending dose.

Biomarker: Measured Urine 5-Hydroxyindoleacetic Acid:

Urine 5 HIAA/24 hour was analyzed in 4 different manners: as measured in the 24-hour collection and (in order to correct for any collection errors) adjusted for creatinine excretion, estimated by the expected creatinine excretion for the subject (as defined in and expressed per gram creatinine. Results were similar for each of the 4 manners and are presented in this report for measured urine. Tables and figures for adjusted, estimated, and per-gram creatinine results are presented in Section 14.

Dosing with KAR5585 reduced measured urine 5-HIAA concentration. Mean percent change in measured urine 5-HIAA was −39.97 from Day 1 to Day 7 and −50.85 from Day 1 to Day 14 in subjects randomized to KAR5575 400 mg under fed conditions. Mean percent change at Day 7 was +9.44 and at Day 14 was +3.97 in subjects randomized to placebo.

Difference of absolute and relative changes from Day 1 in measured urine 5-HIAA on Days 7 and 14 were statistically significant in favor of KAR5585 in all dose groups except one: the relative change on Day 14 for the KAR5585 100 mg fasting dose group (Table 18).

TABLE 18

(Differences of Changes from Day 1 Predose between KAR5585 and Placebo of Measured[a] Urine 5-Hydroxyindoleacetic Acid (mg/24 hours), by Cohort (Biomarker Population))

| | | Mean Difference of Changes from Day 1 between KAR5585 and Placebo | | | |
|---|---|---|---|---|---|
| | | Absolute Change from Day 1 | | % Change from Day 1 | |
| Dose Level/Time | | Estimate (95% CI) | P Value | Estimate (95% CI) | P Value |
| 100 mg Fasting | Predose Day 7 | −0.92 (−1.68, −0.16) | .0208 | −31.97 (−49.29, −14.64) | .0005 |
| | Predose Day 14 | −0.91 (−1.41, −0.40) | .0007 | −17.65 (−39.12, 3.82) | .1113 |
| 100 mg Fed | Predose Day 7 | −2.09 (−2.86, −1.33) | <.0001 | −50.34 (−67.66, −33.01) | <.0001 |
| | Predose Day 14 | −1.65 (−2.18, −1.13) | <.0001 | −36.03 (−58.26, −13.81) | .0022 |
| 200 mg Fed | Predose Day 7 | −0.92 (−1.71, −0.13) | .0248 | −26.95 (−44.89, −9.02) | .0043 |
| | Predose Day 14 | −1.58 (−2.10, −1.06) | <.0001 | −37.11 (−59.33, −14.89) | .0016 |
| 400 mg Fed | Predose Day 7 | −1.68 (−2.44, −0.92) | <.0001 | −49.41 (−66.73, −32.08) | <.0001 |
| | Predose Day 14 | −2.04 (−2.55, −1.54) | <.0001 | −54.82 (−76.29, −33.35) | <.0001 |
| All Doses | Predose Day 7 | −1.42 (−2.00, −0.84) | <.0001 | −40.03 (−53.17, −26.89) | <.0001 |
| | Predose Day 14 | −1.54 (−1.93, −1.16) | <.0001 | −36.39 (−52.74, −20.05) | <.0001 |

[a]Measured is as measured in 24-hour 5HIAA excretion without adjustment for variations in daily creatinine excretion.
Abbreviations:
5-HIAA, 5-hydroxyindoleacetic acid,
CI, confidence interval.

Both absolute and percent changes from Day 1 in creatinine-normalized urine 5-HIAA on Days 7 and 14 were statistically significant in favor of KAR5585 versus placebo in all dose groups.

Serum 5-Hydroxytryptamine:

Mean difference of both absolute and relative changes from Day 1 to Day 14 in serum 5-HT concentration was statistically significant in favor of KAR5585 compared to placebo for the 400 mg fed and all KAR5585 doses pooled (Table 19).

Mean difference of percent changes from Day 1 in serum 5-HT concentration was statistically significant compared to placebo on Day 7 in favor of the 200 mg fed dose group.

While there were no significant correlations on Day 7 between absolute or relative change from baseline in serum 5-HT concentration and $AUC_{0-24}$, $C_{max}$, $C_{12}$, or $AUC_{0-12}$ for KAR5417, both absolute and relative changes on Day 14 were correlated (P<0.0010).

While there were no significant correlations between absolute or relative change from baseline in measured urine 5-HIAA and KAR5417 $AUC_{0-24}$, $C_{max}$, $C_{12}$, or $AUC_{0-12}$ on

TABLE 19

Differences of Changes from Day 1 Predose between KAR5585 and Placebo of (Serum 5-HT (ng/mL) by Cohort - Part 2 MAD Biomarker Population)

| | | Mean Difference of Changes from Day 1 between KAR5585 and Placebo | | | |
|---|---|---|---|---|---|
| | | Absolute Change from Day 1 | | % Change from Day 1 | |
| Dose Level/Time | | Estimate (95% CI) | P Value | Estimate (95% CI) | P Value |
| 100 mg Fasting | Predose Day 7 | −12.97 (−47.53, 21.59) | .4642 | −10.97 (−29.80, 7.85) | .2567 |
| | Predose Day 14 | −17.39 (−52.04, 17.26) | .3285 | −15.92 (−37.90, 6.06) | .1598 |
| 100 mg Fed | Predose Day 7 | −15.75 (−50.31, 18.81) | .3745 | −11.02 (−29.84, 7.81) | .2549 |
| | Predose Day 14 | 5.08 (−30.79, 40.95) | .7820 | −0.47 (−23.22, 22.28) | .9678 |
| 200 mg Fed | Predose Day 7 | −28.53 (−63.09, 6.03) | .1097 | −21.64 (−40.47, −2.82) | .0270 |
| | Predose Day 14 | −5.79 (−41.66, 30.08) | .7525 | −11.43 (−34.18, 11.32) | .3279 |
| 400 mg Fed | Predose Day 7 | 16.47 (−18.09, 51.03) | .3531 | 2.09 (−16.73, 20.91) | .8282 |
| | Predose Day 14 | −84.50 (−119.15, −49.85) | <.0001 | −50.02 (−72.00, −28.04) | <.0001 |
| All Doses | Predose Day 7 | −10.19 (−36.32, 15.93) | .4467 | −10.39 (−24.61, 3.84) | .1566 |
| | Predose Day 14 | −27.14 (−53.52, −0.75) | .0475 | −20.26 (−36.99, −3.52) | .0203 |

Analysis of Biomarkers in Relation to Pharmacokinetic Parameters:

All subjects were dosed with KAR5585 or placebo. Following dosing, KAR5585 was rapidly absorbed and the active moiety KAR5417 appeared rapidly in plasma.

Only those subjects with all biomarker results and results for the PK parameters $AUC_{0-24}$, $C_{min}$, concentration, obtained 12 hr after an administered dose ($C_{12}$ hr), and $AUC_{0-12}$ were included in the PK-Biomarker analyses. The PK parameters $AUC_{0-24}$, $C_{min}$, $C_{12hr}$, and $AUC_{0-12}$ were adjusted from those stated in the protocol ($AUC_{0-24}$, $C_{min}$, and $C_{max}$) to account for the double daily dosing.

All subjects in Part 2 (MAD) were eligible for biomarker analyses. Only the subset of the Biomarker Population randomized to active drug were included in PK-Biomarker analyses.

Pharmacokinetic Parameters and Plasma 5-Hydroxyindoleacetic Acid, the Primary Biomarker Endpoint:

On Day 14, the absolute and relative changes from baseline in plasma 5-HIAA were significantly correlated with KAR5417 $AUC_{0-24}$, $C_{max}$, $C_{12}$, and $AUC_{0-12}$ (P≤0.0010).

Greater values for the PK parameters were associated with greater decreases in plasma 5-HIAA concentrations, as illustrated in FIG. 23, which shows the relationship between relative changes from baseline in plasma 5-HIAA and KAR5417 $AUC_{0-24}$.

FIG. 23 discloses absolute and relative changes at day 14 of Plasma 5-HIAA from Day 1 Predose vs. $AUC_{[0-24]}$ in subjects who received KAR5585—Part 2 MAD Biomarker Population.

Day 7, both absolute and relative changes were significantly correlated for Day 14 (P≤0.0067). Greater values for the PK parameters were associated with greater decreases in measured urine 5-HIAA concentrations, which shows the relationship between relative change in measured urine 5-HIAA (mg/24 hours) from Day 1 to Day 14 and KAR5417 $AUC_{0-24}$.

The relationships between adjusted and estimated urine 5-HIAA and KAR5417 PK parameters were similar to those for measured urine 5-HIAA: though there were no significant correlations on Day 7 between absolute or relative change from baseline in urine 5-HIAA and KAR5417 PK parameters, the correlations were significant on Day 14 for both absolute and relative changes in urine 5-HIAA and KAR5417 PK parameters (adjusted urine 5-HIAA, P≤0.0007; estimated urine 5-HIAA, P≤0.0110).

Discussion of Biomarker Results

There was a strong association between plasma 5-HIAA (pre-established as the primary biomarker endpoint) and both KAR5585 dose and the duration of dosing. The mean reduction from Day 1 to Day 14 in plasma 5-HIAA was greater for the highest dose (−53.33%, 400 mg fed) than for the lowest dose (−28.71%, 100 mg fasting; −32.58%, 100 mg fed). The mean percent difference of change from Day 1 between KAR5585 and placebo was significant (P<0.0001) for each dose group and all doses pooled at Day 14 but not significant at Day 7 for any dose group.

There was also a strong association between urine 5-HIAA/24 hours and KAR5585 dose. At the highest KAR5585 dose, 400 mg, mean percent change in measured urine 5-HIAA was ⍰ 50.85 from Day 1 to Day 14, whereas mean percent change in subjects randomized to placebo was +3.97. Mean differences of absolute and relative changes from Day 1 to Day 14 were statistically significant in favor of KAR5585 in all dose groups except one (the relative change on Day 14 for the KAR5585 100 mg fasting dose group). Results were comparable in urine 5-HIAA/24 hours as adjusted, estimated, and per gram creatinine.

Serum 5-HT did not reveal the strong association between the biomarker of serotonin and KAR5585 dose or duration of dosing. The differences of changes from Day 1 between KAR5585 and placebo were statistically significant for the highest dose group (400 mg fed) and for all KAR5585 doses pooled.

A strong relationship was seen between KAR5417 exposure and 5-HIAA reductions. A strong relationship between both plasma and urine 5-HIAA is supported by the observation that higher exposure to KAR5417, as measured by the PK parameters $AUC_{0-24}$, $C_{max}$, $C_{12}$, and $AUC_{0-12}$, was associated with greater reduction in 5-HIAA.

Biomarker Conclusions

Dose- and time-dependent reductions were observed in 5-HIAA (a PD marker of 5-HT synthesis) in both plasma and urine.

At the highest KAR5585 dose, 400 mg, mean percent change in plasma 5-HIAA concentration was −53.33 from Day 1 to Day 14, whereas mean percent change in subjects randomized to placebo was +20.12.

At the highest KAR5585 dose, 400 mg, mean percent change in measured urine 5-HIAA was −50.85 from Day 1 to Day 14, whereas mean percent change in subjects randomized to placebo was +3.97. Results were comparable in urine 5-HIAA/24 hours as adjusted, estimated, and per gram creatinine.

A strong relationship was seen between KAR5417 exposure and 5-HIAA reductions.

OVERALL CONCLUSIONS

The study was divided into 2 parts: SAD (Part 1) and MAD (Part 2). Part 1 (SAD) was further divided into Period 1 (fasting administration) and Period 2 (fed administration, food effect). The KAR5585 doses administered were the following:

In Part 1 (SAD) Period 1 (fasting): 100 mg, 200 mg, 400 mg, 700 mg, 1200 mg, or 2000 mg in Cohorts 1 through 6, respectively In Part 1 (SAD) Period 2 (fed, high-fat food effect): 400 mg in Cohort 3 only In Part 2 (MAD): 100 mg (fasting), 100 mg (fed), 200 mg (fed), and 400 mg (fed) or matching placebo administered BID (approximately every 12 hours) for 27 doses in Cohorts 1 through 4, respectively.

Pharmacokinetics: Following administration of KAR5585 (prodrug), KAR5417 (active TPH1 inhibitor) appeared rapidly in plasma, an observation consistent with rapid absorption of KAR5585 and efficient conversion to KAR5417.

Administration of the KAR5585 under fed conditions in Part 1, Period 2, increased the extent and peak of exposure of both KAR5585 and KAR5417. This was considered to be a clinically-relevant change in exposure. In Part 2, the mean extent of systemic exposure to KAR5417, as measured by mean $AUC_{0-12}$ and $AUC_{0-24}$, appeared comparable under fasted conditions. This observation is in contrast to the food-effect comparison in Part 1.

Biomarkers: Dose- and time-dependent reductions were observed in 5-HIAA (a PD marker of 5-HT synthesis) in both plasma and urine.

At the highest KAR5585 dose, 400 mg, mean percent change in plasma 5-HIAA concentration was −53.33 from Day 1 to Day 14, whereas mean percent change in subjects randomized to placebo was +20.12.

At the highest KAR5585 dose, 400 mg, mean percent change in measured urine 5-HIAA was −50.85 from Day 1 to Day 14, whereas mean percent change in subjects randomized to placebo was +3.97. Results were comparable in urine 5-HIAA/24 hours as adjusted, estimated, and per gram creatinine.

A strong relationship was seen between KAR5417 exposure and 5-HIAA reductions.

Following administration of KAR5585 (prodrug), KAR5417 (active TPH1 inhibitor) appeared rapidly in plasma, an observation consistent with rapid absorption of KAR5585 and efficient conversion to KAR5417. A strong relationship was seen between KAR5417 exposure and 5-HIAA reductions. Neither the prodrug (KAR5585) nor the active drug (KAR5417) showed any tendency to increase QTcF in a dose-dependent manner.

It should be understood that the foregoing description is only illustrative of the present disclosure. Various alternatives and modifications can be devised by those skilled in the art without departing from the present disclosure. Accordingly, the present disclosure is intended to embrace all such alternatives, modifications and variances which fall within the scope of the appended claims.

What is claimed is:

1. A daily dosage regimen for treating pulmonary arterial hypertension in a human patient, comprising two discrete dosage forms, wherein the dosage forms each include an amount of about 600 mg to about 800 mg of crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate, wherein the crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by XRPD peaks at 8.78±0.20, 14.87±0.20, 15.39±0.20, 15.61±0.20, 18.45±0.20, and 19.05±0.20° 2θ.

2. The daily dosage regimen of claim 1, wherein the dosage forms each include RVT-1201, wherein the (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by an XRPD pattern substantially as depicted in FIG. 1.

3. The daily dosage regimen of claim 1, wherein the dosage forms are oral dosage forms.

4. The daily dosage regimen of claim 1, wherein each of the dosage forms further include an amount of a pharmaceutically acceptable excipient.

5. A daily dosage regimen for treating pulmonary arterial hypertension in a human patient, comprising an amount of 1200 mg to 1600 mg of crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate, wherein the crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by XRPD peaks at 8.78±0.20, 14.87±0.20, 15.39±0.20, 15.61±0.20, 18.45±0.20, and 19.05±0.20° 2θ.

6. The daily dosage regimen of claim 5, wherein the (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by an XRPD pattern substantially as depicted in FIG. 1.

7. The daily dosage regimen of claim 6, wherein the amount further includes a pharmaceutically acceptable excipient.

8. A method for treating pulmonary arterial hypertension, comprising administering to a human patient in need thereof an amount of 1200 mg to 1600 mg of crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate per day,
wherein the crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by an XRPD peak at 19.05±0.20° 2θ.

9. The method of claim 8, wherein the (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by an XRPD pattern substantially as depicted in FIG. 1.

10. The method of claim 8, wherein the amount is administered orally.

11. The method of claim 8, wherein the amount is administered at 600 mg to 800 mg BID.

12. A method for reducing the level of serotonin biosynthesis by at least 50% within 14 days after commencement of treatment, comprising administering to a human patient in need thereof an amount of about 800 mg to about 1600 mg of crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate per day,
wherein the crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by an XRPD peak at 19.05±0.20° 2θ.

13. The method of claim 12, wherein the (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by an XRPD pattern substantially as depicted in FIG. 1.

14. The method of claim 12, wherein the amount is administered orally.

15. The method of claim 12, wherein the amount is administered is about 400 mg to about 800 mg BID.

16. The method of claim 12, wherein the amount is administered at dosages selected from the group consisting of about 400 mg BID, 600 mg BID, and 800 mg BID.

17. A method for achieving an $AUC_{0-tau}$ of ≥2530 ng·hr/mL of (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid within 14 days after administration, comprising administering daily to a human patient an effective amount of crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate,
wherein the crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by an XRPD peak at 19.05±0.20° 2θ.

18. The method of claim 17, wherein the amount administered is about 800 mg to about 1600 mg per day.

19. The method of claim 18, wherein the amount is administered is about 400 mg to about 800 mg BID.

20. A method of achieving a >50% reduction in urinary 5-HIAA within 14 days after administration, comprising administering daily to a human patient an effective amount of crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate,
wherein the crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by XRPD peaks at 8.78±0.20, 14.87±0.20, 15.39±0.20, 15.61±0.20, 18.45±0.20, and 19.05±0.20° 2θ.

21. The method of claim 19, wherein the amount administered is about 800 mg to about 1600 mg per day.

22. The method of claim 20, wherein the amount is administered is about 400 mg to about 800 mg BID.

23. A method for treating pulmonary arterial hypertension, comprising administering daily to a human patient in need thereof an amount of crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate sufficient to achieve an $AUC_{0-tau}$ of ≥2530 ng·hr/mL of (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid within 14 days after commencement of administration,
wherein the crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by XRPD peaks at 8.78±0.20, 14.87±0.20, 15.39±0.20, 15.61±0.20, 18.45±0.20, and 19.05±0.20° 2θ.

24. A method for treating pulmonary arterial hypertension, comprising administering daily to a human patient in need thereof an amount of crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate effective to achieve a >50% reduction in urinary 5-HIAA within 14 days after commencement of administration,
wherein the crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by XRPD peaks at 8.78±0.20, 14.87±0.20, 15.39±0.20, 15.61±0.20, 18.45±0.20, and 19.05±0.20° 2θ.

25. The method of claim 8, wherein the (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate is characterized by XRPD peaks at 8.78±0.20, 14.87±0.20, 15.39±0.20, 15.61±0.20, 18.45±0.20, and 19.05±0.20° 2θ.

26. The method of claim 8, wherein the amount is administered at 600 mg to 800 mg BID for up to 14 days.

27. The method of claim 8, wherein the amount is administered subcutaneously, topically, parenterally, rectally, or by inhalation spray.

28. The method of claim 12, wherein the (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3- carboxylate is characterized by XRPD peaks at 8.78±0.20, 14.87±0.20, 15.39±0.20, 15.61±0.20, 18.45±0.20, and 19.05±0.20° 2θ.

\* \* \* \* \*